US011395851B2

(12) United States Patent
Weiner et al.

(10) Patent No.: US 11,395,851 B2
(45) Date of Patent: Jul. 26, 2022

(54) EPSTEIN-BARR VIRUS NUCLEIC ACID CONSTRUCTS AND VACCINES MADE THEREFROM, AND METHODS OF USING SAME

(71) Applicant: THE WISTAR INSTITUTE OF ANATOMY AND BIOLOGY, Philadelphia, PA (US)

(72) Inventors: David Weiner, Merion, PA (US); Alfredo Perales Puchalt, Philadelphia, PA (US)

(73) Assignee: THE WISTAR INSTITUTE OF ANATOMY AND BIOLOGY, Philadelphia, PA (US)

( * ) Notice: Subject to any disclaimer, the term of this patent is extended or adjusted under 35 U.S.C. 154(b) by 0 days.

(21) Appl. No.: 16/970,084

(22) PCT Filed: Feb. 15, 2019

(86) PCT No.: PCT/US2019/018159
§ 371 (c)(1),
(2) Date: Aug. 14, 2020

(87) PCT Pub. No.: WO2019/161163
PCT Pub. Date: Aug. 22, 2019

(65) Prior Publication Data
US 2021/0038711 A1 Feb. 11, 2021

Related U.S. Application Data

(60) Provisional application No. 62/710,396, filed on Feb. 16, 2018.

(51) Int. Cl.
| | | |
|---|---|---|
| *A61K 39/245* | (2006.01) | |
| *A61P 31/22* | (2006.01) | |
| *C07K 14/05* | (2006.01) | |
| *C12N 15/79* | (2006.01) | |
| *A61K 39/00* | (2006.01) | |

(52) U.S. Cl.
CPC .......... *A61K 39/245* (2013.01); *A61P 31/22* (2018.01); *C07K 14/05* (2013.01); *C12N 15/79* (2013.01); *A61K 2039/53* (2013.01)

(58) Field of Classification Search
CPC .. A61K 39/245; A61K 2039/53; A61K 39/12; A61P 31/22; C07K 14/05; C12N 15/79
See application file for complete search history.

(56) References Cited

U.S. PATENT DOCUMENTS

| | | | |
|---|---|---|---|
| 2006/0233770 A1 | 10/2006 | Ambinder | |
| 2007/0196389 A1 | 8/2007 | Caligiuri | |
| 2016/0130308 A1 | 5/2016 | Weiner | |
| 2016/0303224 A1* | 10/2016 | Kanekiyo | A61K 39/12 |
| 2018/0028645 A1 | 2/2018 | Ciaramella | |
| 2020/0282047 A1* | 9/2020 | Ciaramella | C12N 7/00 |

FOREIGN PATENT DOCUMENTS

WO    2015054639    4/2015

OTHER PUBLICATIONS

Kanda T, Yajima M, Ikuta K. Epstein-Barr virus strain variation and cancer. Cancer Sci. Apr. 2019;110(4):1132-1139. Epub Feb. 21, 2019.; Tzellos S, Farrell PJ. Epstein-barrvirussequence variation-biology and disease. Pathogens. Nov. 8, 2012;1(2):156-74. (Year: 2019).*
Tzellos S, Farrell PJ. Epstein-barr virus sequence variation-biology and disease. Pathogens. Nov. 8, 2012;1(2):156-74. (Year: 2012).*
Bowie JU, Reidhaar-Olson JF, Lim WA, Sauer RT. Deciphering the message in protein sequences: tolerance to amino acid substitutions. Science. Mar. 16, 1990;247(4948):1306-10. (Year: 1990).*
Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 1, 20005;165(8):4505-14. (Year: 2000).*
Kussie PH, Parhami-Seren B, Wysocki LJ, Margolies MN. A single engineered amino acid substitution changes antibody fine specificity. J Immunol. Jan. 1, 1994;152(1):146-52. (Year: 1994).*
Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. NatCommun. Mar. 30, 2015;6:6714. (Year :2015).*
Sela-Culang I, Kunik V, Ofran Y. The structural basis of antibody-antigen recognition. Front Immunol. Oct. 8, 2013;4:302. (Year: 2013).*
Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2015).*
Tsuchiya Y, Mizuguchi K. The diversity of H3 loops determines the antigen-binding tendencies of antibody CDR loops. Protein Sci. Apr. 2016;25(4):815-25. Epub Jan. 20, 2016. (Year: 2016).*
Collis AV, Brouwer AP, Martin AC. Analysis of the antigen combining site: correlations between length and sequence composition of the hypervariable loops and the nature of the antigen. J Mol Biol. Jan. 10, 2003;325(2):337-54. (Year: 2003).*
Dondelinger M, Filée P, Sauvage E, Quinting B, Muyldermans S, Galleni M, Vandevenne MS. Understanding the Significance and Implications of Antibody Numbering and Antigen-Binding Surface/Residue Definition. Front Immunol. Oct. 16, 2018;9:2278. (Year: 2018).*

(Continued)

*Primary Examiner* — Rachel B Gill
(74) *Attorney, Agent, or Firm* — Riverside Law LLP

(57) ABSTRACT

Nucleic acid molecules and compositions comprising one or more nucleotide sequences that encode a consensus Epstein-Barr virus (EBV) antigen. Immunomodulatory methods and methods of inducing an immune response against EBV are disclosed. Method of treating infection by EBV and methods of treating or preventing a disease or disorder associated with EBV are disclosed. Modified consensus EBV antigens are disclosed.

18 Claims, 37 Drawing Sheets

Specification includes a Sequence Listing.

(56) References Cited

OTHER PUBLICATIONS

Santpere G, Darre F, Blanco S, Alcami A, Villoslada P, Mar Albà M, Navarro A. Genome-wide analysis of wild-type Epstein-Barr virus genomes derived from healthy individuals of the 1,000 Genomes Project. Genome Biol Evol. Apr. 2014;6(4):846-60. (Year: 2014).*

Perez EM, Foley J, Tison T, Silva R, Ogembo JG. Novel Epstein-Barr virus-like particles incorporating gH/gL-EBNA1 or GB-LMP2 induce high neutralizing antibody titers and EBV-specific T-cell responses in immunized mice. Oncotarget. Mar. 21, 2017;8(12):19255-19273. (Year: 2017).*

Lei H, et al. Human herpesvirus 4strain K4123-MiEBV, partial genome. GenBank: KC440852.1, Pub. Dec. 1, 2013. (Year: 2013).*

Cahir McFarland ED, Izumi KM, Mosialos G. Epstein-barr virus transformation: involvement of latent membrane protein 1-mediated activation of NF-kappaB. Oncogene. Nov. 22, 1999;18(49):6959-64. (Year: 1999).*

* cited by examiner

| Tumor | Subtype | Typical latent period | EBV association (%) | EBV antigen expression | Latency |
|---|---|---|---|---|---|
| Burkitt's lymphoma | Endemic | 3–8 y post-EBV | 100 | EBNA1 | I |
| | Sporadic | 3–8 y post-EBV | 15–85 | | |
| | AIDS-associated | 3–8 y post-HIV⁺¹ | 30–40 | | |
| Gastric carcinoma | UCNT | >30 y post-EBV | 100 | | |
| | Adenocarcinoma | >30 y post-EBV | 5–15 | EBNA1, LMP2 | II |
| Nasopharyngeal carcinoma | Nonkeratinizing | >30 y post-EBV | 100 | | |
| | Keratinizing | >30 y post-EBV | 30–100 | EBNA1,(LMP1), LMP2 | II |
| T-cell lymphoma | VAHS-associated | 1–2 y post-EBV | 100 | | |
| | Nasal NK & T-cell | >30 y post-EBV | 100 | EBNA1,(LMP1), LMP2 | II |

Fig. 1

| | | | | |
|---|---|---|---|---|
| Hodgkin's disease | Mixed cell, lymphocyte deplete | >10 y post-EBV | 60~80 | |
| | Nodular sclerosing | >10 y post-EBV | 20~40 | EBNA1, LMP1, LMP2 II |
| PPTLD-like lymphoma | Immunodeficiency | <3 mo post-EBV | 100 | |
| | Posttransplantation | <1 y posttransplantation | >90 | EBNA1,2,3A,3B,3C, -LP, LMP1, LMP2 III |
| | AIDS-associated | <8 y post-HIV | >90 | |
| Leiomyo-sarcoma | Immunodeficiency | ?<3 y post-EBV | ?100 | ? ? |
| | Posttransplantation | ?<3 y posttransplantation | ?100 | |
| | AIDS-associated | ?<3 y post-EBV | ?100 | |

Fig. 1 (cont.)

| Protein | Cell type and latency type | | | | |
|---|---|---|---|---|---|
| | BL | NPC | | CLL | LCL |
| | Type I | Type IIa | | Type IIb | Type III |
| EBNA1 | + | + | | + | + |
| EBNA2 | − | − | | + | + |
| LMP1 | − | +/− | | − | + |
| LMP2A | − | + | | + | + |
| BARF1 | − | + | | − | − |

Fig. 2

| Tumour | Subtype | % EBV positive | EBV proteins expressed |
|---|---|---|---|
| Burkitt Lymphoma | Endemic | 100 | EBNA1[a] |
| | AIDS-related | 30–40 | |
| T/NK Lymphoma | Extranodal | 100 | EBNA1, LMP2B[b] |
| Diffuse large B-cell lymphoma | Late PT-DLBCL | >50 | EBNA1, LMP1, LMP2[c] |
| | Elderly DLBCL | >50 | |
| | AIDS-related | ~50 | |
| Hodgkin lymphoma | Classical | 30 | EBNA1, LMP1, LMP2 |
| | AIDS-related | 100 | |
| Lympho-proliferative disease | Post-transplant, AIDS-related | 100 | EBNA1, EBNA2, EBNA3A, EBNA3B, EBNA3C, EBNA-LP, LMP1, LMP2 |
| Nasopharyngeal carcinoma | Undifferentiated | 100 | EBNA1, LMP1, LMP2[d] |
| Gastric carcinoma | | 5–15 | EBNA1, LMP2[d] |

Fig. 3

SEQUENCE LISTING

```
<160> NUMBER OF SEQ ID NOS: 43

<210> SEQ ID NO 1
<211> LENGTH: 2661
<212> TYPE: DNA
<213> ORGANISM: Artificial Sequence
<220> FEATURE:
<223> OTHER INFORMATION: Chemically synthesized, gp350

<400> SEQUENCE: 1
gaggaccctg gattttcaa tgtcgagatt cccgagttcc ccttttaccc tacatgcaac      60
gtgtgcaccg ccgacgtgaa cgtgaccatc aatttcgatg tgggcggcaa gaagcaccag     120
ctggacctgg attttggcca gctgacccca cacacaaagg ccgtgtatca gccacgcggc     180
gccttcggcg gctccgagaa cgccaccaat ctgtttctgc tggagctgct gggagcagga     240
gagctggccc tgaccatgag gtctaagaag ctgcctatca acgtgaccac aggcgaggag     300
cagcaggtgt ctctggagag cgtggacgtg tacttccagg acgtgttcgg caccatgtgg     360
tgccaccacg ccgagatgca gaatccagtg tacctgatcc ctgagacagt gccatatatc     420
aagtgggaca actgtaatag caccaacatc acagcagtgg tgcgggcaca gggcctggac     480
gtgaccctgc ccctgtctct gcctacaagc gcccaggatt ccaacttctc tgtgaagacc     540
cagatgctgg gcaatgagat cgacatcgag tgcatcatgg aggatggcga gatctcccag     600
gtgctgccag gcgataacaa gtttaatatc acctgttccg gatacgagtc tcacgtgcca     660
agcggcggca tcctgaccag cacatcccct gtggccacac ctatcccagg caccggctac     720
gcatatagcc tgaggctgac ccccaggccc gtgagcaggt tcctgggcaa caattctatc     780
ctgtacgtgt tttatagcgg aaacggacct aaggcatccg gcggcgacta ttgcatccag     840
tctaatatcg tgttcagcga cgagatccca gccagccagg atatgcctac caacaccaca     900
```

```
gacatcacat acgtgggcga taatgccacc tattccgtgc caatggtgac atccgaggac    960
gccaactctc ccaatgtgac cgtgacagcc ttctgggcct ggcctaacaa taccgagaca   1020
gacttcaagt gtaagtggac cctgacatcc ggcaccccat ctggctgtga acatcagc    1080
ggcgccttcg cctccaatag aacatttgac atcaccgtgt ccggcctggg aacagcaccc   1140
aagaccctga tcatcacccg gacagccacc aacgccacta caaccacaca caaagtgatc   1200
ttcagcaagg cccccgagag caccacaacc tcccctaccc tgaacacaac cggctttgcc   1260
gcccctaata caaccacagg cctgcctagc tccaccacg tgccaaccaa cctgacagca    1320
cctgcatcca ccggaccaac agtgtctacc gcagatgtga caagcccaac ccagcagga    1380
accacaagcg gagcatcccc agtgacccct ctccaagcc caggacaa tggcacagag    1440
tccaaggccc ccgatatgac atctcctacc agcgccgtga ccacacctac ccaaacgcc    1500
acatccccaa cccctgcagt gaccacacca acacccaatg ccacatctcc taccccagcc   1560
gtgaccacac ccaccctaa cgccacaagc ccaaccctgg gcaagacatc ccccaccct    1620
gccgtgacca caccaacccc taacgccaca tctcctaccc tgggcaagac aagcccaacc   1680
tccgccgtca ctaccccaac cccaaacgcc acaagcccca ccctgggcaa gatatctcct   1740
accagcgccg taaccacacc cacccctaat gccacatctc caaccgtggg agagacaagc   1800
ccccaggcaa acgcaacaaa tcacaccctg ggcggcacat ccccaacccc agtggtgacc   1860
tctccccta gaacgccac aagcgccgtg accacaggcc agcacaatat cacatctagc    1920
tccacctcta gcatgagcct gaggccctcc tctatccccg agacactgtc ccctctacc    1980
agcgacaatt ccacatctca catgcctctg ctgaccagcg cccacccaac aggcggcgag   2040
aacatcacac aggtgacccc tgccagcaca tccacccacc acgtgtccac cagctcccct   2100
gccccacggc ccggcaccac atcccaggcc tctggcccctg caactctag cacaagcacc   2160
aagccaggcg aggtgaacgt gacaaagggc accccaccca agaatgccac ctctccacag   2220
gcaccaagcg gacagaagac agcagtgcca acagtgacct ccacaggcgg caaggccaac   2280
tctaccacag gcggcaagca caccacagga cacggagcac gcaccagcac agagccaacc   2340
acagattacg gcggcgattc caccacacct cggccacgct acaatgccac cacatatctg   2400
cctccatcta cctcctctaa gctgaggccc agatggacct tcacaagccc tccgtgacc    2460
acagcacagg caaccgtgcc cgtgccaccc acatcccagc ctaggtttag caacctgtcc   2520
atgctggtgc tgcagtgggc atctctggcc gtgctgaccc tgctgctgct gctggtcatg   2580
gccgattgtg ccttcaggag aaacctgagc acaagccata catacaccac cccaccatac   2640
gacgacgcag aaacatacgt g                                             2661
```

<210> SEQ ID NO 2
<211> LENGTH: 887
<212> TYPE: PRT
<213> ORGANISM: Artificial Sequence
<220> FEATURE:
<223> OTHER INFORMATION: Chemically synthesized, gp350

<400> SEQUENCE: 2

```
Glu Asp Pro Gly Phe Phe Asn Val Glu Ile Pro Glu Phe Pro Phe Tyr
1               5                   10                  15

Pro Thr Cys Asn Val Cys Thr Ala Asp Val Asn Val Thr Ile Asn Phe
            20                  25                  30

Asp Val Gly Gly Lys Lys His Gln Leu Asp Leu Asp Phe Gly Gln Leu
        35                  40                  45
```

Thr Pro His Thr Lys Ala Val Tyr Gln Pro Arg Gly Ala Phe Gly Gly
    50                  55                  60

Ser Glu Asn Ala Thr Asn Leu Phe Leu Leu Glu Leu Leu Gly Ala Gly
65                  70                  75                  80

Glu Leu Ala Leu Thr Met Arg Ser Lys Lys Leu Pro Ile Asn Val Thr
                    85                  90                  95

Thr Gly Glu Glu Gln Gln Val Ser Leu Glu Ser Val Asp Val Tyr Phe
                100                 105                 110

Gln Asp Val Phe Gly Thr Met Trp Cys His His Ala Glu Met Gln Asn
            115                 120                 125

Pro Val Tyr Leu Ile Pro Glu Thr Val Pro Tyr Ile Lys Trp Asp Asn
        130                 135                 140

Cys Asn Ser Thr Asn Ile Thr Ala Val Arg Ala Gln Gly Leu Asp
145                 150                 155                 160

Val Thr Leu Pro Leu Ser Leu Pro Thr Ser Ala Gln Asp Ser Asn Phe
                165                 170                 175

Ser Val Lys Thr Gln Met Leu Gly Asn Glu Ile Asp Ile Glu Cys Ile
            180                 185                 190

Met Glu Asp Gly Glu Ile Ser Gln Val Leu Pro Gly Asp Asn Lys Phe
        195                 200                 205

Asn Ile Thr Cys Ser Gly Tyr Glu Ser His Val Pro Ser Gly Gly Ile
210                 215                 220

Leu Thr Ser Thr Ser Pro Val Ala Thr Pro Ile Pro Gly Thr Gly Tyr
225                 230                 235                 240

Ala Tyr Ser Leu Arg Leu Thr Pro Arg Pro Val Ser Arg Phe Leu Gly
                245                 250                 255

Asn Asn Ser Ile Leu Tyr Val Phe Tyr Ser Gly Asn Gly Pro Lys Ala
            260                 265                 270

Ser Gly Gly Asp Tyr Cys Ile Gln Ser Asn Ile Val Phe Ser Asp Glu
        275                 280                 285

Ile Pro Ala Ser Gln Asp Met Pro Thr Asn Thr Thr Asp Ile Thr Tyr
290                 295                 300

Val Gly Asp Asn Ala Thr Tyr Ser Val Pro Met Val Thr Ser Glu Asp
305                 310                 315                 320

Ala Asn Ser Pro Asn Val Thr Val Thr Ala Phe Trp Ala Trp Pro Asn
                325                 330                 335

Asn Thr Glu Thr Asp Phe Lys Cys Lys Trp Thr Leu Thr Ser Gly Thr
            340                 345                 350

Pro Ser Gly Cys Glu Asn Ile Ser Gly Ala Phe Ala Ser Asn Arg Thr
        355                 360                 365

Phe Asp Ile Thr Val Ser Gly Leu Gly Thr Ala Pro Lys Thr Leu Ile
    370                 375                 380

Ile Thr Arg Thr Ala Thr Asn Ala Thr Thr Thr His Lys Val Ile
385                 390                 395                 400

Phe Ser Lys Ala Pro Glu Ser Thr Thr Thr Ser Pro Thr Leu Asn Thr
                405                 410                 415

Thr Gly Phe Ala Ala Pro Asn Thr Thr Thr Gly Leu Pro Ser Ser Thr
            420                 425                 430

His Val Pro Thr Asn Leu Thr Ala Pro Ala Ser Thr Gly Pro Thr Val
        435                 440                 445

Ser Thr Ala Asp Val Thr Ser Pro Thr Pro Ala Gly Thr Thr Ser Gly
    450                 455                 460

```
Ala Ser Pro Val Thr Pro Ser Pro Ser Pro Arg Asp Asn Gly Thr Glu
465                 470                 475                 480

Ser Lys Ala Pro Asp Met Thr Ser Pro Thr Ser Ala Val Thr Thr Pro
            485                 490                 495

Thr Pro Asn Ala Thr Ser Pro Thr Pro Ala Val Thr Thr Pro Thr Pro
            500                 505                 510

Asn Ala Thr Ser Pro Thr Pro Ala Val Thr Thr Pro Thr Pro Asn Ala
            515                 520                 525

Thr Ser Pro Thr Leu Gly Lys Thr Ser Pro Thr Ser Ala Val Thr Thr
    530                 535                 540

Pro Thr Pro Asn Ala Thr Ser Pro Thr Leu Gly Lys Thr Ser Pro Thr
545                 550                 555                 560

Ser Ala Val Thr Thr Pro Thr Pro Asn Ala Thr Ser Pro Thr Leu Gly
                565                 570                 575

Lys Thr Ser Pro Thr Ser Ala Val Thr Thr Pro Thr Pro Asn Ala Thr
            580                 585                 590

Ser Pro Thr Val Gly Glu Thr Ser Pro Gln Ala Asn Ala Thr Asn His
            595                 600                 605

Thr Leu Gly Gly Thr Ser Pro Thr Pro Val Val Thr Ser Pro Pro Lys
610                 615                 620

Asn Ala Thr Ser Ala Val Thr Thr Gly Gln His Asn Ile Thr Ser Ser
625                 630                 635                 640

Ser Thr Ser Ser Met Ser Leu Arg Pro Ser Ile Pro Glu Thr Leu
            645                 650                 655

Ser Pro Ser Thr Ser Asp Asn Ser Thr Ser His Met Pro Leu Leu Thr
            660                 665                 670

Ser Ala His Pro Thr Gly Gly Glu Asn Ile Thr Gln Val Thr Pro Ala
            675                 680                 685

Ser Thr Ser Thr His His Val Ser Thr Ser Ser Pro Ala Pro Arg Pro
            690                 695                 700

Gly Thr Thr Ser Gln Ala Ser Gly Pro Gly Asn Ser Ser Thr Ser Thr
705                 710                 715                 720

Lys Pro Gly Glu Val Asn Val Thr Lys Gly Thr Pro Pro Lys Asn Ala
                725                 730                 735

Thr Ser Pro Gln Ala Pro Ser Gly Gln Lys Thr Ala Val Pro Thr Val
            740                 745                 750

Thr Ser Thr Gly Gly Lys Ala Asn Ser Thr Thr Gly Gly Lys His Thr
    755                 760                 765

Thr Gly His Gly Ala Arg Thr Ser Thr Glu Pro Thr Thr Asp Tyr Gly
    770                 775                 780

Gly Asp Ser Thr Thr Pro Arg Pro Arg Tyr Asn Ala Thr Thr Tyr Leu
785                 790                 795                 800

Pro Pro Ser Thr Ser Ser Lys Leu Arg Pro Arg Trp Thr Phe Thr Ser
            805                 810                 815

Pro Pro Val Thr Thr Ala Gln Ala Thr Val Pro Val Pro Pro Thr Ser
            820                 825                 830

Gln Pro Arg Phe Ser Asn Leu Ser Met Leu Val Leu Gln Trp Ala Ser
            835                 840                 845

Leu Ala Val Leu Thr Leu Leu Leu Leu Val Met Ala Asp Cys Ala
            850                 855                 860

Phe Arg Arg Asn Leu Ser Thr Ser His Thr Tyr Thr Thr Pro Pro Tyr
865                 870                 875                 880

Asp Asp Ala Glu Thr Tyr Val
```

-continued

```
                  885

<210> SEQ ID NO 3
<211> LENGTH: 570
<212> TYPE: DNA
<213> ORGANISM: Artificial Sequence
<220> FEATURE:
<223> OTHER INFORMATION: Chemically synthesized, gp42

<400> SEQUENCE: 3
gggggaaggg tcgcagcagc cgctatcact tgggtgccta agccaaatgt ggaagtgtgg        60
ccagtggacc ctccccctcc cgtgaacttc aataagacag ccgagcagga gtacggcgat       120
aaggaggtga agctgccaca ctggaccccc acactgcaca cattccaggt gcctcagaac       180
tacaccaagg ccaattgcac ctattgtaac acaagggagt acaccttttc ctataagggc       240
tgctgtttct acttcaccaa gaagaagcac acctggaatg gctgcttcca ggcctgtgcc       300
gagctgtatc cttgcacata cttttatggc cccacccctg acatcctgcc agtggtgacc       360
aggaacctga atgccatcga gtctctgtgg gtgggcgtgt atagagtggg cgagggcaac       420
tggacatctc tggatggcgg caccttcaag gtgtaccaga tctttggcag ccactgtaca       480
tatgtgagca agttttccac cgtgcccgtg agccaccacg agtgctcatt cctgaaaccc       540
tgtctgtgcg tctcccagcg aagtaatagc                                        570

<210> SEQ ID NO 4
<211> LENGTH: 190
<212> TYPE: PRT
<213> ORGANISM: Artificial Sequence
<220> FEATURE:
<223> OTHER INFORMATION: gp42

<400> SEQUENCE: 4

Gly Gly Arg Val Ala Ala Ala Ile Thr Trp Val Pro Lys Pro Asn
1               5                   10                  15

Val Glu Val Trp Pro Val Asp Pro Pro Pro Val Asn Phe Asn Lys
                20                  25                  30

Thr Ala Glu Gln Glu Tyr Gly Asp Lys Glu Val Lys Leu Pro His Trp
        35                  40                  45

Thr Pro Thr Leu His Thr Phe Gln Val Pro Gln Asn Tyr Thr Lys Ala
    50                  55                  60

Asn Cys Thr Tyr Cys Asn Thr Arg Glu Tyr Thr Phe Ser Tyr Lys Gly
65                  70                  75                  80

Cys Cys Phe Tyr Phe Thr Lys Lys Lys His Thr Trp Asn Gly Cys Phe
                85                  90                  95

Gln Ala Cys Ala Glu Leu Tyr Pro Cys Thr Tyr Phe Tyr Gly Pro Thr
            100                 105                 110

Pro Asp Ile Leu Pro Val Val Thr Arg Asn Leu Asn Ala Ile Glu Ser
        115                 120                 125

Leu Trp Val Gly Val Tyr Arg Val Gly Glu Gly Asn Trp Thr Ser Leu
    130                 135                 140

Asp Gly Gly Thr Phe Lys Val Tyr Gln Ile Phe Gly Ser His Cys Thr
145                 150                 155                 160

Tyr Val Ser Lys Phe Ser Thr Val Pro Val Ser His His Glu Cys Ser
                165                 170                 175

Phe Leu Lys Pro Cys Leu Cys Val Ser Gln Arg Ser Asn Ser
            180                 185                 190
```

<210> SEQ ID NO 5
<211> LENGTH: 345
<212> TYPE: DNA
<213> ORGANISM: Artificial Sequence
<220> FEATURE:
<223> OTHER INFORMATION: Chemically synthesized, gL

<400> SEQUENCE: 5

```
aactgggctt acccctgttg tcacgtcact cagctgaggg cacagcacct gctggccctg      60
gagaacatct ctgacatcta cctggtgagc aatcagacct gcgatggctt cagcctggcc     120
tccctgaact ctcccaagaa cggctccaat cagctggtca tctctcgctg tgccaacggc     180
ctgaatgtgg tgagcttctt tatctccatc ctgaagagga gctcctctgc cctgaccggc     240
cacctgagag agctgctgac cacactggag acactgtatg gcagcttctc tgtggaggac     300
ctgtttgggg ctaacctgaa tagatacgcc tggcaccgag ggga                      345
```

<210> SEQ ID NO 6
<211> LENGTH: 115
<212> TYPE: PRT
<213> ORGANISM: Artificial Sequence
<220> FEATURE:
<223> OTHER INFORMATION: Chemically synthesized, gL

<400> SEQUENCE: 6

```
Asn Trp Ala Tyr Pro Cys Cys His Val Thr Gln Leu Arg Ala Gln His
1               5                   10                  15

Leu Leu Ala Leu Glu Asn Ile Ser Asp Ile Tyr Leu Val Ser Asn Gln
            20                  25                  30

Thr Cys Asp Gly Phe Ser Leu Ala Ser Leu Asn Ser Pro Lys Asn Gly
        35                  40                  45

Ser Asn Gln Leu Val Ile Ser Arg Cys Ala Asn Gly Leu Asn Val Val
    50                  55                  60

Ser Phe Phe Ile Ser Ile Leu Lys Arg Ser Ser Ser Ala Leu Thr Gly
65                  70                  75                  80

His Leu Arg Glu Leu Leu Thr Thr Leu Glu Thr Leu Tyr Gly Ser Phe
                85                  90                  95

Ser Val Glu Asp Leu Phe Gly Ala Asn Leu Asn Arg Tyr Ala Trp His
            100                 105                 110

Arg Gly Gly
        115
```

<210> SEQ ID NO 7
<211> LENGTH: 2064
<212> TYPE: DNA
<213> ORGANISM: Artificial Sequence
<220> FEATURE:
<223> OTHER INFORMATION: Chemically synthesized, gH

<400> SEQUENCE: 7

```
tccctgtctg aagtcaaact gcatctggat attgagggcc acgccagcca ctacacaatc      60
ccttggaccg agctgatggc aaaggtgcca ggcctgtccc ctgaggccct gtggagggag     120
gccaatgtga ccgaggacct ggcctctatg ctgaacagat acaagctgat ctataagaca     180
agcggcaccc tgggaatcgc cctggcagag ccagtggaca tcccagccgt gtccgagggc     240
tctatgcagg tggatgcctc taaggtgcac ccaggcgtga tctccggcct gaactctcca     300
gcatgcatgc tgagcgcccc tctggagaag cagctgttct actatatcgg cacaatgctg     360
cctaatacca ggccacactc ctacgtgttt tatcagctga gatgtcacct gtcctacgtg     420
```

| | |
|---|---|
| gccctgtcta tcaacggcga caagttccag tatacaggcg ccatgacctc caagtttctg | 480 |
| atgggcacat acaagagggt gaccgagaag ggcgatgagc acgtgctgtc tctggtgttc | 540 |
| ggcaagacaa aggacctgcc cgatctgaga ggccccttta gctacccttc cctgacctct | 600 |
| gcccagagcg cgactattc cctggtcatc gtgaccacat cgtgcacta cgccaacttc | 660 |
| cacaattatt ttgtgcccaa tctgaaggat atgttttcta gggccgtgac aatgaccgcc | 720 |
| gccagctacg ccagatatgt gctgcagaag ctggtgctgc tggagatgaa gggcggctgc | 780 |
| agggagcctg agctggacac agagacactg accacaatgt tcgaggtgag cgtggccttc | 840 |
| tttaaagtgg gacacgcagt gggagagaca ggaaacggct gcgtggacct gagatggctg | 900 |
| gccaagagct tctttgagct gacagtgctg aaggatatca tcggcatctg ttacggcgcc | 960 |
| accgtgaagg gcatgcagtc ctatggcctg agcggctgg cagcaatgct gatggcaacc | 1020 |
| gtgaagatgg aggagctggg ccacctgacc acagagaagc aggagtacgc actgaggctg | 1080 |
| gcaacagtgg gatacccaaa ggccggcgtg tattctggcc tgatcggcgg cgccaccagc | 1140 |
| gtgctgctgt ccgcctataa tcggcaccca ctgttccagc ccctgcacac agtgatgcgc | 1200 |
| gagacactgt tcatcggcag ccacgtggtg ctgagggagc tgagactgaa tgtgaccaca | 1260 |
| cagggcccca acctggccct gtaccagctg ctgagcacag ccctgtgctc cgccctggag | 1320 |
| atcggagagg tgctgagggg cctggccctg ggcaccgagt ctggcctgtt cagcccttgt | 1380 |
| tatctgtccc tgcggtttga cctgacacgc gataagctgc tgtctatggc cccacaggag | 1440 |
| gccaccctgg accaggcagc cgtgagcaat gcagtggatg gcttcctggg ccggctgtcc | 1500 |
| ctggagaggg aggacaggga tgcatggcac ctgccagcct acaagtgcgt ggaccgcctg | 1560 |
| gataaggtgc tgatgatcat ccccctgatc aacgtgacct tcatcatcag ctccgacagg | 1620 |
| gaggtgagag gctctgccct gtacgaggcc agcaccacat atctgtctag ctccctgttt | 1680 |
| ctgagccctg tgatcatgaa taagtgttcc cagggagcag tggcaggaga gcctaggcag | 1740 |
| atcccaaaga tccagaactt cacacgcacc cagaagtcct gcatcttctg tggctttgcc | 1800 |
| ctgctgtctt acgatgagaa ggagggcctg gagacaacaa cctatatcac atcccaggag | 1860 |
| gtgcagaact ctatcctgtc tagcaattac ttcgactttg ataacctgca cgtgcactat | 1920 |
| ctgctgctga caaccaacgg caccgtgatg gagatcgcag gcctgtacga ggagagggca | 1980 |
| cacgtggtgc tggccatcat cctgtatttc atcgcctttg ccctggggat tttcctggtc | 2040 |
| cataagattg tcatgttttt cctg | 2064 |

<210> SEQ ID NO 8
<211> LENGTH: 688
<212> TYPE: PRT
<213> ORGANISM: Artificial Sequence
<220> FEATURE:
<223> OTHER INFORMATION: Chemically synthesized, gH

<400> SEQUENCE: 8

Ser Leu Ser Glu Val Lys Leu His Leu Asp Ile Glu Gly His Ala Ser
1               5                   10                  15

His Tyr Thr Ile Pro Trp Thr Glu Leu Met Ala Lys Val Pro Gly Leu
            20                  25                  30

Ser Pro Glu Ala Leu Trp Arg Glu Ala Asn Val Thr Glu Asp Leu Ala
        35                  40                  45

Ser Met Leu Asn Arg Tyr Lys Leu Ile Tyr Lys Thr Ser Gly Thr Leu
    50                  55                  60

Gly Ile Ala Leu Ala Glu Pro Val Asp Ile Pro Ala Val Ser Glu Gly

```
                65                  70                  75                  80

Ser Met Gln Val Asp Ala Ser Lys Val His Pro Gly Val Ile Ser Gly
                    85                  90                  95

Leu Asn Ser Pro Ala Cys Met Leu Ser Ala Pro Leu Glu Lys Gln Leu
                100                 105                 110

Phe Tyr Tyr Ile Gly Thr Met Leu Pro Asn Thr Arg Pro His Ser Tyr
                115                 120                 125

Val Phe Tyr Gln Leu Arg Cys His Leu Ser Tyr Val Ala Leu Ser Ile
            130                 135                 140

Asn Gly Asp Lys Phe Gln Tyr Thr Gly Ala Met Thr Ser Lys Phe Leu
145                 150                 155                 160

Met Gly Thr Tyr Lys Arg Val Thr Glu Lys Gly Asp Glu His Val Leu
                165                 170                 175

Ser Leu Val Phe Gly Lys Thr Lys Asp Leu Pro Asp Leu Arg Gly Pro
            180                 185                 190

Phe Ser Tyr Pro Ser Leu Thr Ser Ala Gln Ser Gly Asp Tyr Ser Leu
                195                 200                 205

Val Ile Val Thr Thr Phe Val His Tyr Ala Asn Phe His Asn Tyr Phe
            210                 215                 220

Val Pro Asn Leu Lys Asp Met Phe Ser Arg Ala Val Thr Met Thr Ala
225                 230                 235                 240

Ala Ser Tyr Ala Arg Tyr Val Leu Gln Lys Leu Val Leu Leu Glu Met
                245                 250                 255

Lys Gly Gly Cys Arg Glu Pro Glu Leu Asp Thr Glu Thr Leu Thr Thr
                260                 265                 270

Met Phe Glu Val Ser Val Ala Phe Phe Lys Val Gly His Ala Val Gly
            275                 280                 285

Glu Thr Gly Asn Gly Cys Val Asp Leu Arg Trp Leu Ala Lys Ser Phe
            290                 295                 300

Phe Glu Leu Thr Val Leu Lys Asp Ile Ile Gly Ile Cys Tyr Gly Ala
305                 310                 315                 320

Thr Val Lys Gly Met Gln Ser Tyr Gly Leu Glu Arg Leu Ala Ala Met
                325                 330                 335

Leu Met Ala Thr Val Lys Met Glu Glu Leu Gly His Leu Thr Thr Glu
                340                 345                 350

Lys Gln Glu Tyr Ala Leu Arg Leu Ala Thr Val Gly Tyr Pro Lys Ala
            355                 360                 365

Gly Val Tyr Ser Gly Leu Ile Gly Gly Ala Thr Ser Val Leu Leu Ser
            370                 375                 380

Ala Tyr Asn Arg His Pro Leu Phe Gln Pro Leu His Thr Val Met Arg
385                 390                 395                 400

Glu Thr Leu Phe Ile Gly Ser His Val Val Leu Arg Glu Leu Arg Leu
                405                 410                 415

Asn Val Thr Thr Gln Gly Pro Asn Leu Ala Leu Tyr Gln Leu Leu Ser
            420                 425                 430

Thr Ala Leu Cys Ser Ala Leu Glu Ile Gly Glu Val Leu Arg Gly Leu
            435                 440                 445

Ala Leu Gly Thr Glu Ser Gly Leu Phe Ser Pro Cys Tyr Leu Ser Leu
            450                 455                 460

Arg Phe Asp Leu Thr Arg Asp Lys Leu Leu Ser Met Ala Pro Gln Glu
465                 470                 475                 480

Ala Thr Leu Asp Gln Ala Ala Val Ser Asn Ala Val Asp Gly Phe Leu
            485                 490                 495
```

```
Gly Arg Leu Ser Leu Glu Arg Glu Asp Arg Asp Ala Trp His Leu Pro
            500                 505                 510
Ala Tyr Lys Cys Val Asp Arg Leu Asp Lys Val Leu Met Ile Ile Pro
        515                 520                 525
Leu Ile Asn Val Thr Phe Ile Ile Ser Ser Asp Arg Glu Val Arg Gly
    530                 535                 540
Ser Ala Leu Tyr Glu Ala Ser Thr Thr Tyr Leu Ser Ser Ser Leu Phe
545                 550                 555                 560
Leu Ser Pro Val Ile Met Asn Lys Cys Ser Gln Ala Val Ala Gly
                565                 570                 575
Glu Pro Arg Gln Ile Pro Lys Ile Gln Asn Phe Thr Arg Thr Gln Lys
            580                 585                 590
Ser Cys Ile Phe Cys Gly Phe Ala Leu Leu Ser Tyr Asp Glu Lys Glu
        595                 600                 605
Gly Leu Glu Thr Thr Thr Tyr Ile Thr Ser Gln Glu Val Gln Asn Ser
    610                 615                 620
Ile Leu Ser Ser Asn Tyr Phe Asp Phe Asp Asn Leu His Val His Tyr
625                 630                 635                 640
Leu Leu Leu Thr Thr Asn Gly Thr Val Met Glu Ile Ala Gly Leu Tyr
                645                 650                 655
Glu Glu Arg Ala His Val Val Leu Ala Ile Ile Leu Tyr Phe Ile Ala
            660                 665                 670
Phe Ala Leu Gly Ile Phe Leu Val His Lys Ile Val Met Phe Phe Leu
        675                 680                 685

<210> SEQ ID NO 9
<211> LENGTH: 2505
<212> TYPE: DNA
<213> ORGANISM: Artificial Sequence
<220> FEATURE:
<223> OTHER INFORMATION: Chemically synthesized, gB

<400> SEQUENCE: 9
cagacacccg agcagcccgc tcccccagca actacagtgc agcccacagc caccagacag    60
cagacctcct tccctttttcg ggtgtgcgag ctgagctccc acggcgacct gttcagattt   120
tctagcgata tccagtgtcc ttctttcggc acacgggaga accacaccga gggcctgctg   180
atggtgttca aggacaatat catcccatac tcttttaagg tgcgcagcta tacaaagatc   240
gtgaccaaca tcctgatcta caatggctgg tatgccgact ccgtgaccaa caggcacgag   300
gagaagtttt ccgtggattc ttacgagaca gaccagatgg ataccatcta ccagtgctat   360
aatgccgtga agatgacaaa ggacggcctg accagagtgt atgtggaccg ggatggcgtg   420
aacatcacag tgaatctgaa gccaaccggc ggcctggcaa acggcgtgag agatacgcc    480 agccagaccg agctgtatga tgcccccggc tggctgatct ggacataccg caccaggacc   540
acagtgaact gtctgatcac cgacatgatg gccaagtcta atagcccctt cgatttcttt   600
gtgaccacaa ccggccagac agtggagatg agcccttttt atgacggcaa gaacaaggag   660
acattccacg agagagccga ttcctttcac gtgcggacca attacaagat cgtggactat   720
gataatagag aacaaatcc acaggagag aggagggcct tcctggacaa gggcacatac   780
accctgtcct ggaagctgga gaaccggacc gcctattgcc ctctgcagca ctggcagaca   840
tttgactcca ccatcgccac agagacaggc aagtctatcc acttcgtgac agatgagggc   900
acctcctctt ttgtgaccaa cacaaccgtg ggcatcgagc tgcctgacgc cttcaagtgt   960
```

```
atcgaggagc aagtgaataa gaccatgcac gagaagtacg aggccgtgca ggatcgctat    1020
acaaagggcc aggaggccat cacatacttt atcacctccg gcggcctgct gctggcatgg    1080
ctgccactga cccccaggag cctggccaca gtgaagaacc tgaccgagct gacaacccct    1140
acaagcagcc ctccctctag cccaagccca cccgccccct cagcagcaag aggctccacc    1200
tctgccgccg tgctgaggag acggcgcagg gacgccggca acgcaacaac cccagtgccc    1260
cctgcagcac ctggcaagtc tctgggcaca ctgaacaatc cagccaccgt gcagatccag    1320
ttcgcctacg acagcctgag acggcagatc aataggatgc tgggcgatct ggcaagggca    1380
tggtgcctgg agcagaagcg ccagaacatg gtgctgaggg agctgaccaa gatcaatcca    1440
acaaccgtga tgtcctctat ctacggcaag gcagtggcag caaagagact gggcgatgtg    1500
atcagcgtgt cccagtgcgt gcccgtgaac caggccacag tgaccctgcg caagagcatg    1560
agggtgccag gctccgagac aatgtgctac tctcggcccc tggtgtcttt cagctttatc    1620
aacgacacaa agacctatga gggccagctg ggcaccgata atgagatctt cctgacaaag    1680
aagatgaccg aggtgtgcca ggccacaagc cagtactatt tccagtccgg caacgagatc    1740
cacgtgtaca atgactatca ccactttaag accatcgagc tggatggcat cgccacactg    1800
cagaccttca tctccctgaa cacatctctg atcgagaata tcgactttgc ctccctggag    1860
ctgtactcta gagacgagca gcgggcctcc aacgtgttcg atctggaggg catcttccgg    1920
gagtataact ttcaggccca gaatatcgcc ggcctgcgca aggacctgga taatgccgtg    1980
agcaacggca ggaatcagtt tgtggacggc ctgggcgagc tgatggatag cctgggctcc    2040
gtgggccagt ctatcacaaa cctggtgagc accgtgggcg gcctgttcag ctccctggtg    2100
agcggcttta tctccttctt taagaatccc ttcgcggca tgctgatcct ggtgctggtg    2160
gccggcgtgg tcatcctggt catcagcctg acacgcagga cccgccagat gtcccagcag    2220
ccagtgcaga tgctgtaccc aggaatcgac gagctggcac agcagcacgc atctggagag    2280
ggacctggca tcaacccaat cagcaagacc gagctgcagg ccatcatgct ggccctgcac    2340
gagcagaatc aggagcagaa gagggcagca cagagggcag caggaccttc tgtggccagc    2400
agggccctgc aggcagcaag agatcggttc ccaggcctga cggagaag ataccacgac    2460 cccgagaccg ctgctgctct gctgggcgag gctgagaccg agttt          2505
```

<210> SEQ ID NO 10
<211> LENGTH: 835
<212> TYPE: PRT
<213> ORGANISM: Artificial Sequence
<220> FEATURE:
<223> OTHER INFORMATION: Chemically synthesized, gB

<400> SEQUENCE: 10

```
Gln Thr Pro Glu Gln Pro Ala Pro Pro Ala Thr Thr Val Gln Pro Thr
1               5                   10                  15

Ala Thr Arg Gln Gln Thr Ser Phe Pro Phe Arg Val Cys Glu Leu Ser
            20                  25                  30

Ser His Gly Asp Leu Phe Arg Phe Ser Ser Asp Ile Gln Cys Pro Ser
        35                  40                  45

Phe Gly Thr Arg Glu Asn His Thr Glu Gly Leu Leu Met Val Phe Lys
    50                  55                  60

Asp Asn Ile Ile Pro Tyr Ser Phe Lys Val Arg Ser Tyr Thr Lys Ile
65                  70                  75                  80

Val Thr Asn Ile Leu Ile Tyr Asn Gly Trp Tyr Ala Asp Ser Val Thr
                85                  90                  95
```

```
Asn Arg His Glu Glu Lys Phe Ser Val Asp Ser Tyr Glu Thr Asp Gln
            100                 105                 110

Met Asp Thr Ile Tyr Gln Cys Tyr Asn Ala Val Lys Met Thr Lys Asp
            115                 120                 125

Gly Leu Thr Arg Val Tyr Val Asp Arg Asp Gly Val Asn Ile Thr Val
        130                 135                 140

Asn Leu Lys Pro Thr Gly Gly Leu Ala Asn Gly Val Arg Arg Tyr Ala
145                 150                 155                 160

Ser Gln Thr Glu Leu Tyr Asp Ala Pro Gly Trp Leu Ile Trp Thr Tyr
                165                 170                 175

Arg Thr Arg Thr Thr Val Asn Cys Leu Ile Thr Asp Met Met Ala Lys
            180                 185                 190

Ser Asn Ser Pro Phe Asp Phe Val Thr Thr Gly Gln Thr Val
            195                 200                 205

Glu Met Ser Pro Phe Tyr Asp Gly Lys Asn Lys Glu Thr Phe His Glu
        210                 215                 220

Arg Ala Asp Ser Phe His Val Arg Thr Asn Tyr Lys Ile Val Asp Tyr
225                 230                 235                 240

Asp Asn Arg Gly Thr Asn Pro Gln Gly Glu Arg Arg Ala Phe Leu Asp
                245                 250                 255

Lys Gly Thr Tyr Thr Leu Ser Trp Lys Leu Glu Asn Arg Thr Ala Tyr
            260                 265                 270

Cys Pro Leu Gln His Trp Gln Thr Phe Asp Ser Thr Ile Ala Thr Glu
            275                 280                 285

Thr Gly Lys Ser Ile His Phe Val Thr Asp Glu Gly Thr Ser Ser Phe
        290                 295                 300

Val Thr Asn Thr Thr Val Gly Ile Glu Leu Pro Asp Ala Phe Lys Cys
305                 310                 315                 320

Ile Glu Glu Gln Val Asn Lys Thr Met His Glu Lys Tyr Glu Ala Val
                325                 330                 335

Gln Asp Arg Tyr Thr Lys Gly Gln Glu Ala Ile Thr Tyr Phe Ile Thr
            340                 345                 350

Ser Gly Gly Leu Leu Leu Ala Trp Leu Pro Leu Thr Pro Arg Ser Leu
        355                 360                 365

Ala Thr Val Lys Asn Leu Thr Glu Leu Thr Thr Pro Thr Ser Ser Pro
370                 375                 380

Pro Ser Ser Pro Ser Pro Ala Pro Pro Ala Ala Arg Gly Ser Thr
385                 390                 395                 400

Ser Ala Ala Val Leu Arg Arg Arg Arg Asp Ala Gly Asn Ala Thr
                405                 410                 415

Thr Pro Val Pro Pro Ala Ala Pro Gly Lys Ser Leu Gly Thr Leu Asn
            420                 425                 430

Asn Pro Ala Thr Val Gln Ile Gln Phe Ala Tyr Asp Ser Leu Arg Arg
            435                 440                 445

Gln Ile Asn Arg Met Leu Gly Asp Leu Ala Arg Ala Trp Cys Leu Glu
            450                 455                 460

Gln Lys Arg Gln Asn Met Val Leu Arg Glu Leu Thr Lys Ile Asn Pro
465                 470                 475                 480

Thr Thr Val Met Ser Ser Ile Tyr Gly Lys Ala Val Ala Ala Lys Arg
                485                 490                 495

Leu Gly Asp Val Ile Ser Val Ser Gln Cys Val Pro Val Asn Gln Ala
            500                 505                 510
```

```
Thr Val Thr Leu Arg Lys Ser Met Arg Val Pro Gly Ser Glu Thr Met
            515                 520                 525
Cys Tyr Ser Arg Pro Leu Val Ser Phe Ser Phe Ile Asn Asp Thr Lys
        530                 535                 540
Thr Tyr Glu Gly Gln Leu Gly Thr Asp Asn Glu Ile Phe Leu Thr Lys
545                 550                 555                 560
Lys Met Thr Glu Val Cys Gln Ala Thr Ser Gln Tyr Tyr Phe Gln Ser
                565                 570                 575
Gly Asn Glu Ile His Val Tyr Asn Asp Tyr His His Phe Lys Thr Ile
            580                 585                 590
Glu Leu Asp Gly Ile Ala Thr Leu Gln Thr Phe Ile Ser Leu Asn Thr
        595                 600                 605
Ser Leu Ile Glu Asn Ile Asp Phe Ala Ser Leu Glu Leu Tyr Ser Arg
    610                 615                 620
Asp Glu Gln Arg Ala Ser Asn Val Phe Asp Leu Gly Ile Phe Arg
625                 630                 635                 640
Glu Tyr Asn Phe Gln Ala Gln Asn Ile Ala Gly Leu Arg Lys Asp Leu
                645                 650                 655
Asp Asn Ala Val Ser Asn Gly Arg Asn Gln Phe Val Asp Gly Leu Gly
            660                 665                 670
Glu Leu Met Asp Ser Leu Gly Ser Val Gly Gln Ser Ile Thr Asn Leu
        675                 680                 685
Val Ser Thr Val Gly Gly Leu Phe Ser Ser Leu Val Ser Gly Phe Ile
    690                 695                 700
Ser Phe Phe Lys Asn Pro Phe Gly Gly Met Leu Ile Leu Val Leu Val
705                 710                 715                 720
Ala Gly Val Val Ile Leu Val Ile Ser Leu Thr Arg Arg Thr Arg Gln
                725                 730                 735
Met Ser Gln Gln Pro Val Gln Met Leu Tyr Pro Gly Ile Asp Glu Leu
            740                 745                 750
Ala Gln Gln His Ala Ser Gly Glu Gly Pro Gly Ile Asn Pro Ile Ser
        755                 760                 765
Lys Thr Glu Leu Gln Ala Ile Met Leu Ala Leu His Glu Gln Asn Gln
    770                 775                 780
Glu Gln Lys Arg Ala Ala Gln Arg Ala Ala Gly Pro Ser Val Ala Ser
785                 790                 795                 800
Arg Ala Leu Gln Ala Ala Arg Asp Arg Phe Pro Gly Leu Arg Arg Arg
                805                 810                 815
Arg Tyr His Asp Pro Glu Thr Ala Ala Ala Leu Leu Gly Glu Ala Glu
            820                 825                 830
Thr Glu Phe
        835

<210> SEQ ID NO 11
<211> LENGTH: 1215
<212> TYPE: DNA
<213> ORGANISM: Artificial Sequence
<220> FEATURE:
<223> OTHER INFORMATION: Chemically synthesized, gM

<400> SEQUENCE: 11
atgaaaagca gcaaaaatga taccttcgtc tacaggactt ggtttaagac tctggtcgtc      60
tacttcgtga tgttcgtgat gtcagccgtg gtgcctatca cagccatgtt ccctaacctg     120
ggctacccat gctacttcaa cgccctggtg gactacggcg ccctgaacct gaccaactat     180
```

-continued

```
aatctggccc caccacctgac cccaacactg tacctggagc ccctgagat gttcgtgtac      240 atcacactgg tgttcatcgc cgactgcgtg gccttatct actatgcctg tggcgaggtg      300
gccctgatca aggcccgcaa gaaggtgagc ggcctgacag atctgagcgc ctgggtgtcc     360
gccgtgggct ctcctaccgt gctgttcctg gccatcctga agctgtggtc catccaggtg     420
ttcatccagg tgctgtctta caagcacgtg tttctgagcg ccttcgtgta ttttctgcac     480
ttcctggcat ctgtgctgca cgcatgcgca tgcgtgacaa ggttctctcc cgtgtgggtg     540
gtgaaggccc aggacaacag catccctcag gataccttc tgtggtgggt ggtgttctac      600
ctgaagccag tggtgacaaa tctgtatctg ggctgcctgg ccctggagac actggtgttc    660
agcctgagcg tgttcctggc cctgggcaac agcttctact ttatggtggg cgacatggtg    720
ctgggcgccg tgaatctgtt tctgatcctg cccatcttct ggtatatcct gaccgaagtg    780
tggctggcca gcttcctgag acacaacttc ggctttact gtggcatgtt tatcgcctcc     840
atcatcctga tcctgccact ggtgcggtat gaggccgtgt tcgtgtctgc caagctgcac    900
accacagtgg ccatcaatgt ggccatcatc cccatcctgt gctccgtggc catgctgatc    960
cgcatctgta ggatctttaa gtctatgcgg cagggcaccg attacgtgcc cgtgagcgag   1020
acagtggagc tggagctgga gtccgagcca agaccccggc ctagcagaac ccatccccca   1080
ggacggaata ggagacggag ctccacctct agctcctcta gccgctccac aaggaggcag   1140
aggcccgtga gcacccaggc tctggtctca agcgtgctgc caatgacaac tgatagcgag   1200
gaggagattt ttcca                                                   1215
```

<210> SEQ ID NO 12
<211> LENGTH: 405
<212> TYPE: PRT
<213> ORGANISM: Artificial Sequence
<220> FEATURE:
<223> OTHER INFORMATION: Chemically synthesized, gM

<400> SEQUENCE: 12

```
Met Lys Ser Ser Lys Asn Asp Thr Phe Val Tyr Arg Thr Trp Phe Lys
 1               5                  10                  15

Thr Leu Val Val Tyr Phe Val Met Phe Val Met Ser Ala Val Val Pro
            20                  25                  30

Ile Thr Ala Met Phe Pro Asn Leu Gly Tyr Pro Cys Tyr Phe Asn Ala
        35                  40                  45

Leu Val Asp Tyr Gly Ala Leu Asn Leu Thr Asn Tyr Asn Leu Ala His
    50                  55                  60

His Leu Thr Pro Thr Leu Tyr Leu Glu Pro Pro Glu Met Phe Val Tyr
65                  70                  75                  80

Ile Thr Leu Val Phe Ile Ala Asp Cys Val Ala Phe Ile Tyr Tyr Ala
                85                  90                  95

Cys Gly Glu Val Ala Leu Ile Lys Ala Arg Lys Lys Val Ser Gly Leu
            100                 105                 110

Thr Asp Leu Ser Ala Trp Val Ser Ala Val Gly Ser Pro Thr Val Leu
        115                 120                 125

Phe Leu Ala Ile Leu Lys Leu Trp Ser Ile Gln Val Phe Ile Gln Val
    130                 135                 140

Leu Ser Tyr Lys His Val Phe Leu Ser Ala Phe Val Tyr Phe Leu His
145                 150                 155                 160

Phe Leu Ala Ser Val Leu His Ala Cys Ala Cys Val Thr Arg Phe Ser
                165                 170                 175
```

```
Pro Val Trp Val Val Lys Ala Gln Asp Asn Ser Ile Pro Gln Asp Thr
            180                 185                 190

Phe Leu Trp Trp Val Val Phe Tyr Leu Lys Pro Val Val Thr Asn Leu
        195                 200                 205

Tyr Leu Gly Cys Leu Ala Leu Glu Thr Leu Val Phe Ser Leu Ser Val
        210                 215                 220

Phe Leu Ala Leu Gly Asn Ser Phe Tyr Phe Met Val Gly Asp Met Val
225                 230                 235                 240

Leu Gly Ala Val Asn Leu Phe Leu Ile Leu Pro Ile Phe Trp Tyr Ile
                245                 250                 255

Leu Thr Glu Val Trp Leu Ala Ser Phe Leu Arg His Asn Phe Gly Phe
            260                 265                 270

Tyr Cys Gly Met Phe Ile Ala Ser Ile Ile Leu Ile Leu Pro Leu Val
        275                 280                 285

Arg Tyr Glu Ala Val Phe Val Ser Ala Lys Leu His Thr Thr Val Ala
        290                 295                 300

Ile Asn Val Ala Ile Ile Pro Ile Leu Cys Ser Val Ala Met Leu Ile
305                 310                 315                 320

Arg Ile Cys Arg Ile Phe Lys Ser Met Arg Gln Gly Thr Asp Tyr Val
                325                 330                 335

Pro Val Ser Glu Thr Val Glu Leu Glu Leu Glu Ser Glu Pro Arg Pro
            340                 345                 350

Arg Pro Ser Arg Thr Pro Ser Pro Gly Arg Asn Arg Arg Ser Ser
        355                 360                 365

Thr Ser Ser Ser Ser Arg Ser Thr Arg Arg Gln Arg Pro Val Ser
        370                 375                 380

Thr Gln Ala Leu Val Ser Ser Val Leu Pro Met Thr Thr Asp Ser Glu
385                 390                 395                 400

Glu Glu Ile Phe Pro
                405

<210> SEQ ID NO 13
<211> LENGTH: 210
<212> TYPE: DNA
<213> ORGANISM: Artificial Sequence
<220> FEATURE:
<223> OTHER INFORMATION: Chemically synthesized, gN

<400> SEQUENCE: 13
tcttcaccta ctaacgccgc cgcagcaagt ctgaccgagg cccaggacca gttctacagc      60
tatacctgca acgccgatac attcagcccc tccctgacct cttttgccag catctgggcc     120
ctgctgaccc tggtgctggt catcatcgcc agcgcaatct acctgatgta tgtctgtttt     180
aataagttcg tgaatactct gctgaccgat                                      210

<210> SEQ ID NO 14
<211> LENGTH: 70
<212> TYPE: PRT
<213> ORGANISM: Artificial Sequence
<220> FEATURE:
<223> OTHER INFORMATION: Chemically synthesized, gN

<400> SEQUENCE: 14

Ser Ser Pro Thr Asn Ala Ala Ala Ala Ser Leu Thr Glu Ala Gln Asp
1               5                   10                  15

Gln Phe Tyr Ser Tyr Thr Cys Asn Ala Asp Thr Phe Ser Pro Ser Leu
            20                  25                  30
```

Thr Ser Phe Ala Ser Ile Trp Ala Leu Leu Thr Leu Val Leu Val Ile
            35                  40                  45

Ile Ala Ser Ala Ile Tyr Leu Met Tyr Val Cys Phe Asn Lys Phe Val
 50                  55                  60

Asn Thr Leu Leu Thr Asp
 65                  70

<210> SEQ ID NO 15
<211> LENGTH: 1071
<212> TYPE: DNA
<213> ORGANISM: Artificial Sequence
<220> FEATURE:
<223> OTHER INFORMATION: Chemically synthesized, BMRF2

<400> SEQUENCE: 15
atgttctctt gtaaacagca tctgagtctg ggagcttgcg tcttttgcct gggcctgctg      60
gcttctaccc ccttcatttg gtgcttcgtg tttgccaacc tgctgtccct ggagatcttc     120
tctccttggc agaccacgt gtacagactg gcttcccaa cagcctgcct gatggccgtg      180
ctgtggaccc tggtgccagc caagcacgcc gtgagagccg tgacaccgc catcatgctg     240
aacatcgcct ctgccctgat cttctttagc ctgcgggtgt actctaccag cacatgggtg    300
agcgcccct gcctgtttct ggccaatctg ccctgctgt gcctgtggcc tagactggcc     360
atcgagatcg tgtatatctg ccctgccatc accagcggt tctttgagct gggcctgctg    420
ctggcctgta caatcttcgc actgagcgtg gtgtcccgcg ccctggaggt gagcgccgtg    480
tttatgtccc ccttctttat cttcctggcc ctgggatccg gctctctggc aggagcaagg    540
agaaaccaga tctataccag cggcctggag cggcgcaggt ccatcttttg cgcaaggggc    600
gaccactctg tggcaagcct gaaggagaca ctgcacaagt gcccatggga tctgctggcc    660
atctccgccc tgaccgtgct ggtggtgtgc gtgatgatcg tgctgcacgt gcacgccgag    720
gtgttctttg gcctgtctag gtacctgcca ctgttcctgt gcggagcaat ggcaagcggc    780
ggcctgtatc tgggacacag ctccatcatc gcctgcgtga tggccaccct gtgcaccctg    840
acatccgtgg tggtgtactt cctgcacgag acactgggcc ctctgggcaa gacagtgctg    900
ttcatctcta tcttcgtgta ctatttctcc ggagtggccg ccctgtctgc cgcaatgcgc    960
tataagctga agaagttcgt gaatggccca ctggtgcacc tgagggtggt gtatatgtgc   1020
tgtttcgtgt tcaccttctg cgagtacctg ctggtcactt tcatcaaatc c            1071

<210> SEQ ID NO 16
<211> LENGTH: 357
<212> TYPE: PRT
<213> ORGANISM: Artificial Sequence
<220> FEATURE:
<223> OTHER INFORMATION: Chemically synthesized, BMRF2

<400> SEQUENCE: 16

Met Phe Ser Cys Lys Gln His Leu Ser Leu Gly Ala Cys Val Phe Cys
 1               5                  10                  15

Leu Gly Leu Leu Ala Ser Thr Pro Phe Ile Trp Cys Phe Val Phe Ala
             20                  25                  30

Asn Leu Leu Ser Leu Glu Ile Phe Ser Pro Trp Gln Thr His Val Tyr
         35                  40                  45

Arg Leu Gly Phe Pro Thr Ala Cys Leu Met Ala Val Leu Trp Thr Leu
     50                  55                  60

Val Pro Ala Lys His Ala Val Arg Ala Val Thr Pro Ala Ile Met Leu
 65                  70                  75                  80

Asn Ile Ala Ser Ala Leu Ile Phe Phe Ser Leu Arg Val Tyr Ser Thr
                85                  90                  95

Ser Thr Trp Val Ser Ala Pro Cys Leu Phe Leu Ala Asn Leu Pro Leu
            100                 105                 110

Leu Cys Leu Trp Pro Arg Leu Ala Ile Glu Ile Val Tyr Ile Cys Pro
        115                 120                 125

Ala Ile His Gln Arg Phe Phe Glu Leu Gly Leu Leu Leu Ala Cys Thr
    130                 135                 140

Ile Phe Ala Leu Ser Val Val Ser Arg Ala Leu Glu Val Ser Ala Val
145                 150                 155                 160

Phe Met Ser Pro Phe Phe Ile Phe Leu Ala Leu Gly Ser Gly Ser Leu
                165                 170                 175

Ala Gly Ala Arg Arg Asn Gln Ile Tyr Thr Ser Gly Leu Glu Arg Arg
            180                 185                 190

Arg Ser Ile Phe Cys Ala Arg Gly Asp His Ser Val Ala Ser Leu Lys
        195                 200                 205

Glu Thr Leu His Lys Cys Pro Trp Asp Leu Leu Ala Ile Ser Ala Leu
    210                 215                 220

Thr Val Leu Val Val Cys Val Met Ile Val Leu His Val His Ala Glu
225                 230                 235                 240

Val Phe Phe Gly Leu Ser Arg Tyr Leu Pro Leu Phe Leu Cys Gly Ala
                245                 250                 255

Met Ala Ser Gly Gly Leu Tyr Leu Gly His Ser Ser Ile Ile Ala Cys
            260                 265                 270

Val Met Ala Thr Leu Cys Thr Leu Thr Ser Val Val Tyr Phe Leu
        275                 280                 285

His Glu Thr Leu Gly Pro Leu Gly Lys Thr Val Leu Phe Ile Ser Ile
    290                 295                 300

Phe Val Tyr Tyr Phe Ser Gly Val Ala Ala Leu Ser Ala Ala Met Arg
305                 310                 315                 320

Tyr Lys Leu Lys Lys Phe Val Asn Gly Pro Leu Val His Leu Arg Val
                325                 330                 335

Val Tyr Met Cys Cys Phe Val Phe Thr Phe Cys Glu Tyr Leu Leu Val
            340                 345                 350

Thr Phe Ile Lys Ser
        355

<210> SEQ ID NO 17
<211> LENGTH: 1260
<212> TYPE: DNA
<213> ORGANISM: Artificial Sequence
<220> FEATURE:
<223> OTHER INFORMATION: Chemically synthesized, BDLF2

<400> SEQUENCE: 17
atggtcgatg aacaggtcgc agtcgagcac ggcacagtgt cacatactat ttccagagag    60
gaggatgggg tcgtccacga gagaagggtg ctggcatctg agagagggt ggaggtgttc   120 tacaaggcac ctgccccacg gccccgcgag ggacgcgcca gcacattcca cgactttacc   180
gtgcctgctg ccgccgccgt gcctggacca gagccagagc tgagccaca ccctcccatg   240 ccaatccacg caaacggcgg cggcgagaca agacaaata cccaggatca gaaccagaat   300
cagaccacaa ggacaagaac caacgccaag gccgaggaga ggacagccga gatgacgat   360 accatggcaa gctccggcgg ccagagaggc gcccccatca gcgccgacct gctgtccctg   420

```
tctagcctga caggaaggat ggcagcaatg gcaccttcct ggatgaagtc tgaggtgtgc    480
ggcgagcgga tgcgctttaa ggaggacgtg tacgatggag aggcagagac actggcagag    540
ccacccagat gtttcatgct gagcttcgtg tttatctact attgctgtta tctggccttt    600
ctggccctgc tggccttcgg ctttaaccct ctgttcctgc catcctttat gcccgtggga    660
gcaaaggtgc tgaggggcaa gggaagggac ttcggagtgc cactgtctta cggctgccca    720
acaaatccct tttgtaaggt gtataccctg atccccgccg tggtcatcaa caatgtgaca    780
tactatccta caataccga tagcctgggc ggccacggcg gattcgaggc cgccgccctg    840
cacgtggccg ccctgtttga gtccggatgc ccaaacctgc aggcagtgac caacaggaat    900
agaacattca atgtgaccag ggcctccggc agagtggaga ggagactggt gcaggacatg    960
cagcgggtgc tggcatctgc cgtggtggtc atgcaccacc actgtcacta tgagacatac    1020
tacgtgttcg acggcgtggg cccagagttt ggcacaatcc ccaccccttg cttcaaggat    1080
gtgctggcct ttcgcccctc cctggtgaca aactgtaccg cccctctgaa gacctctgtg    1140
aagggaccaa attggagcgg agcagccggc ggaatgaaga ggaagcagtg ccgcgtggat    1200
cgcctgactg atagaagttt tcccgcctac ctggaagaag tgatgtatgt gatggtgcag    1260
```

<210> SEQ ID NO 18
<211> LENGTH: 420
<212> TYPE: PRT
<213> ORGANISM: Artificial Sequence
<220> FEATURE:
<223> OTHER INFORMATION: Chemically synthesized, BDLF2

<400> SEQUENCE: 18

```
Met Val Asp Glu Gln Val Ala Val Glu His Gly Thr Val Ser His Thr
1               5                   10                  15

Ile Ser Arg Glu Glu Asp Gly Val Val His Glu Arg Arg Val Leu Ala
            20                  25                  30

Ser Gly Glu Arg Val Glu Val Phe Tyr Lys Ala Pro Ala Pro Arg Pro
        35                  40                  45

Arg Glu Gly Arg Ala Ser Thr Phe His Asp Phe Thr Val Pro Ala Ala
    50                  55                  60

Ala Ala Val Pro Gly Pro Glu Pro Glu Pro Glu Pro His Pro Pro Met
65                  70                  75                  80

Pro Ile His Ala Asn Gly Gly Gly Glu Thr Lys Thr Asn Thr Gln Asp
                85                  90                  95

Gln Asn Gln Asn Gln Thr Thr Arg Thr Arg Thr Asn Ala Lys Ala Glu
            100                 105                 110

Glu Arg Thr Ala Glu Met Asp Asp Thr Met Ala Ser Ser Gly Gly Gln
        115                 120                 125

Arg Gly Ala Pro Ile Ser Ala Asp Leu Leu Ser Leu Ser Ser Leu Thr
    130                 135                 140

Gly Arg Met Ala Ala Met Ala Pro Ser Trp Met Lys Ser Glu Val Cys
145                 150                 155                 160

Gly Glu Arg Met Arg Phe Lys Glu Asp Val Tyr Asp Gly Glu Ala Glu
                165                 170                 175

Thr Leu Ala Glu Pro Pro Arg Cys Phe Met Leu Ser Phe Val Phe Ile
            180                 185                 190

Tyr Tyr Cys Cys Tyr Leu Ala Phe Leu Ala Leu Leu Ala Phe Gly Phe
        195                 200                 205

Asn Pro Leu Phe Leu Pro Ser Phe Met Pro Val Gly Ala Lys Val Leu
    210                 215                 220
```

Arg Gly Lys Gly Arg Asp Phe Gly Val Pro Leu Ser Tyr Gly Cys Pro
225                 230                 235                 240

Thr Asn Pro Phe Cys Lys Val Tyr Thr Leu Ile Pro Ala Val Val Ile
                245                 250                 255

Asn Asn Val Thr Tyr Tyr Pro Asn Asn Thr Asp Ser Leu Gly Gly His
            260                 265                 270

Gly Gly Phe Glu Ala Ala Ala Leu His Val Ala Ala Leu Phe Glu Ser
        275                 280                 285

Gly Cys Pro Asn Leu Gln Ala Val Thr Asn Arg Asn Arg Thr Phe Asn
    290                 295                 300

Val Thr Arg Ala Ser Gly Arg Val Glu Arg Leu Val Gln Asp Met
305                 310                 315                 320

Gln Arg Val Leu Ala Ser Ala Val Val Val Met His His His Cys His
                325                 330                 335

Tyr Glu Thr Tyr Tyr Val Phe Asp Gly Val Gly Pro Glu Phe Gly Thr
            340                 345                 350

Ile Pro Thr Pro Cys Phe Lys Asp Val Leu Ala Phe Arg Pro Ser Leu
        355                 360                 365

Val Thr Asn Cys Thr Ala Pro Leu Lys Thr Ser Val Lys Gly Pro Asn
    370                 375                 380

Trp Ser Gly Ala Ala Gly Gly Met Lys Arg Lys Gln Cys Arg Val Asp
385                 390                 395                 400

Arg Leu Thr Asp Arg Ser Phe Pro Ala Tyr Leu Glu Glu Val Met Tyr
                405                 410                 415

Val Met Val Gln
            420

<210> SEQ ID NO 19
<211> LENGTH: 618
<212> TYPE: DNA
<213> ORGANISM: Artificial Sequence
<220> FEATURE:
<223> OTHER INFORMATION: Chemically synthesized, BDLF3

<400> SEQUENCE: 19
tcttcaactg cttctgctgg gaacgtgact ggaaccacag ccgtgaccac accatcccct      60
tctgccagcg gaccatctac caaccagagc accacactga ccacaacctc cgccccatc     120 acaaccacag ccctgctgag caccaatacc acaaccgtga catccaccgg cacaaccgtg     180
acaccagtgc ccacaaccag caacgcctcc accatcaatg tgacaaccaa ggtgacagcc     240
cagaacatca cagccaccga ggcaggaaca ggcacctcca caggagtgac ctctaatgtg     300
acaaccagga gctccacaac cgcctctgcc acaaccagaa tcaccaacgc cacaaccctg     360
gcccctacac tgtctagcaa gggcaccagc aatgccacaa agacaaccgc cgagctgcct     420
accgtgccag cgagaggca gccctccctg tcttacggcc tgcctctgtg gaccctggtg     480
ttcgtgggcc tgacatttct gatgctgatc ctgatcttcg ccgccggcct gatgatgtct     540
accaagaaca agcccctgga cgaggcactg ctgactaatg ctgtgacaag ggacccatct     600
ctgtataagg gactggtg                                                   618

<210> SEQ ID NO 20
<211> LENGTH: 206
<212> TYPE: PRT
<213> ORGANISM: Artificial Sequence
<220> FEATURE:
<223> OTHER INFORMATION: Chemically synthesized, BDLF3

<400> SEQUENCE: 20

```
Ser Ser Thr Ala Ser Ala Gly Asn Val Thr Gly Thr Thr Ala Val Thr
1               5                   10                  15

Thr Pro Ser Pro Ser Ala Ser Gly Pro Ser Thr Asn Gln Ser Thr Thr
            20                  25                  30

Leu Thr Thr Thr Ser Ala Pro Ile Thr Thr Ala Leu Leu Ser Thr
        35                  40                  45

Asn Thr Thr Thr Val Thr Ser Thr Gly Thr Thr Val Thr Pro Val Pro
    50                  55                  60

Thr Thr Ser Asn Ala Ser Thr Ile Asn Val Thr Thr Lys Val Thr Ala
65                  70                  75                  80

Gln Asn Ile Thr Ala Thr Glu Ala Gly Thr Gly Thr Ser Thr Gly Val
                85                  90                  95

Thr Ser Asn Val Thr Thr Arg Ser Ser Thr Ala Ser Ala Thr Thr
                100                 105                 110

Arg Ile Thr Asn Ala Thr Thr Leu Ala Pro Thr Leu Ser Ser Lys Gly
            115                 120                 125

Thr Ser Asn Ala Thr Lys Thr Thr Ala Glu Leu Pro Thr Val Pro Asp
    130                 135                 140

Glu Arg Gln Pro Ser Leu Ser Tyr Gly Leu Pro Leu Trp Thr Leu Val
145                 150                 155                 160

Phe Val Gly Leu Thr Phe Leu Met Leu Ile Leu Phe Ala Ala Gly
                165                 170                 175

Leu Met Met Ser Thr Lys Asn Lys Pro Leu Asp Glu Ala Leu Leu Thr
            180                 185                 190

Asn Ala Val Thr Arg Asp Pro Ser Leu Tyr Lys Gly Leu Val
            195                 200                 205
```

<210> SEQ ID NO 21
<211> LENGTH: 693
<212> TYPE: DNA
<213> ORGANISM: Artificial Sequence
<220> FEATURE:
<223> OTHER INFORMATION: Chemically synthesized, BILF2

<400> SEQUENCE: 21

```
ttcttctctg atctggtcaa attcgaaaac gtgaccgcac acgcaggagc aagagtgaac    60
ctgacatgca gcgtgccctc caatgagagc gtgtccagga tcgagctggg aaggggctac   120
accccaggcg acggacagct gccactggca gtggccacat ctaacaatgg cacccacatc   180
acaaacggcg atacaattat tccctgacca ctggagtggg tgaacgattc taatacatct   240
gtgagcctga tcatccctaa cgtgaccctg gcccacgccg gctactatac ctgcaacgtg   300
acactgagga attgttctgt ggccagcgga gtgcactgca actactccgc cggagaggag   360
gacgatcagt atcacgccaa taggacccctg acacagagaa tgcacctgac cgtgatccct   420
gccaccacaa tcgccccaac cacactggtg agccacacca tccacatctc acaggcct    480
cacaggaggc ccgtgagcaa gcgccccacc cacaagcctg tgacactggg ccccttccct   540
atcgacccat ggaggcccaa gaccacatgg gtgcactggg ccctgctgct gatcacctgt   600
gcagtggtgg cacccgtgct gctgatcatc atcatttcct gcctgggctg gctggctggc   660
tgggggagaa gacgcaaggg atggattcct ctg                                693
```

<210> SEQ ID NO 22
<211> LENGTH: 231

<212> TYPE: PRT
<213> ORGANISM: Artificial Sequence
<220> FEATURE:
<223> OTHER INFORMATION: Chemically synthesized, BILF2

<400> SEQUENCE: 22

```
Phe Phe Ser Asp Leu Val Lys Phe Glu Asn Val Thr Ala His Ala Gly
1               5                   10                  15

Ala Arg Val Asn Leu Thr Cys Ser Val Pro Ser Asn Glu Ser Val Ser
            20                  25                  30

Arg Ile Glu Leu Gly Arg Gly Tyr Thr Pro Gly Asp Gly Gln Leu Pro
        35                  40                  45

Leu Ala Val Ala Thr Ser Asn Asn Gly Thr His Ile Thr Asn Gly Gly
    50                  55                  60

Tyr Asn Tyr Ser Leu Thr Leu Glu Trp Val Asn Asp Ser Asn Thr Ser
65                  70                  75                  80

Val Ser Leu Ile Ile Pro Asn Val Thr Leu Ala His Ala Gly Tyr Tyr
                85                  90                  95

Thr Cys Asn Val Thr Leu Arg Asn Cys Ser Val Ala Ser Gly Val His
            100                 105                 110

Cys Asn Tyr Ser Ala Gly Glu Glu Asp Asp Gln Tyr His Ala Asn Arg
        115                 120                 125

Thr Leu Thr Gln Arg Met His Leu Thr Val Ile Pro Ala Thr Thr Ile
    130                 135                 140

Ala Pro Thr Thr Leu Val Ser His Thr Thr Ser Thr Ser His Arg Pro
145                 150                 155                 160

His Arg Arg Pro Val Ser Lys Arg Pro Thr His Lys Pro Val Thr Leu
                165                 170                 175

Gly Pro Phe Pro Ile Asp Pro Trp Arg Pro Lys Thr Thr Trp Val His
            180                 185                 190

Trp Ala Leu Leu Leu Ile Thr Cys Ala Val Val Ala Pro Val Leu Leu
        195                 200                 205

Ile Ile Ile Ile Ser Cys Leu Gly Trp Leu Ala Gly Trp Gly Arg Arg
    210                 215                 220

Arg Lys Gly Trp Ile Pro Leu
225                 230
```

<210> SEQ ID NO 23
<211> LENGTH: 867
<212> TYPE: DNA
<213> ORGANISM: Artificial Sequence
<220> FEATURE:
<223> OTHER INFORMATION: Chemically synthesized, BILF1

<400> SEQUENCE: 23

```
accgaagacg cttgtactaa gagctattca gcattcctgt ccggcatgac ctctctgctg      60
ctggtgctgc tgatcctgct gacactggcc ggcatcctgt tcatcatctt tgtgagaaag     120
ctggtgcacc ggatggacgt gtggctgatc gccctgctga tcgagctgct gctgtgggtg     180
ctgggcaaga tgatccagga gttcagctcc accggcctgt gcctgctgac acagaacatg     240
atgtttctgg gcctgatgtg cagcgtgtgg acccacctgg aatggcact ggagaagaca     300 ctggccctgt tctctcggac ccccaagcgc acaagccaca ggaacgtgtg cctgtacctg     360
atgggcgtgt ttgtctggt gctgctgctg atcatcatcc tgctgatcac catgggccct     420
gatgccaacc tgaatcgcgg cccaaatatg tgcaggagg ccccaccaa gggcatgcac      480 acagcagtgc agggcctgaa ggcaggatgt tatctgctgg ccgccgtgct gatcgtgctg     540
```

```
ctgaccgtga tcatcatctg gaagctgctg aggacaaagt tcggcaggaa gcctagactg    600
atctgcaatg tgacctttac aggcctgatc tgtgccttca gctggtttat gctgtccctg    660
ccactgctgt tcctgggaga ggcaggctcc ctgggatttg actgcacaga gtctctggtg    720
gccagatact atccaggacc tgcagcatgt ctggccctgc tgctgatcat cctgtacgcc    780
tggtctttca gccactttat ggattccctg aagaaccagg tcacagtcac agcacgatac    840
tttagacgag tcccctcaca gtccaca                                        867
```

<210> SEQ ID NO 24
<211> LENGTH: 289
<212> TYPE: PRT
<213> ORGANISM: Artificial Sequence
<220> FEATURE:
<223> OTHER INFORMATION: Chemically synthesized, BILF1

<400> SEQUENCE: 24

```
Thr Glu Asp Ala Cys Thr Lys Ser Tyr Ser Ala Phe Leu Ser Gly Met
  1               5                  10                  15

Thr Ser Leu Leu Leu Val Leu Leu Ile Leu Leu Thr Leu Ala Gly Ile
             20                  25                  30

Leu Phe Ile Ile Phe Val Arg Lys Leu Val His Arg Met Asp Val Trp
         35                  40                  45

Leu Ile Ala Leu Leu Ile Glu Leu Leu Trp Val Leu Gly Lys Met
 50                  55                  60

Ile Gln Glu Phe Ser Ser Thr Gly Leu Cys Leu Leu Thr Gln Asn Met
 65                  70                  75                  80

Met Phe Leu Gly Leu Met Cys Ser Val Trp Thr His Leu Gly Met Ala
                 85                  90                  95

Leu Glu Lys Thr Leu Ala Leu Phe Ser Arg Thr Pro Lys Arg Thr Ser
            100                 105                 110

His Arg Asn Val Cys Leu Tyr Leu Met Gly Val Phe Cys Leu Val Leu
        115                 120                 125

Leu Leu Ile Ile Ile Leu Leu Ile Thr Met Gly Pro Asp Ala Asn Leu
    130                 135                 140

Asn Arg Gly Pro Asn Met Cys Arg Glu Gly Pro Thr Lys Gly Met His
145                 150                 155                 160

Thr Ala Val Gln Gly Leu Lys Ala Gly Cys Tyr Leu Leu Ala Ala Val
                165                 170                 175

Leu Ile Val Leu Leu Thr Val Ile Ile Trp Lys Leu Leu Arg Thr
            180                 185                 190

Lys Phe Gly Arg Lys Pro Arg Leu Ile Cys Asn Val Thr Phe Thr Gly
        195                 200                 205

Leu Ile Cys Ala Phe Ser Trp Phe Met Leu Ser Pro Leu Leu Phe
    210                 215                 220

Leu Gly Glu Ala Gly Ser Leu Gly Phe Asp Cys Thr Glu Ser Leu Val
225                 230                 235                 240

Ala Arg Tyr Tyr Pro Gly Pro Ala Ala Cys Leu Ala Leu Leu Leu Ile
                245                 250                 255

Ile Leu Tyr Ala Trp Ser Phe Ser His Phe Met Asp Ser Leu Lys Asn
            260                 265                 270

Gln Val Thr Val Thr Ala Arg Tyr Phe Arg Arg Val Pro Ser Gln Ser
        275                 280                 285

Thr
```

<210> SEQ ID NO 25
<211> LENGTH: 603
<212> TYPE: DNA
<213> ORGANISM: Artificial Sequence
<220> FEATURE:
<223> OTHER INFORMATION: Chemically synthesized, BARF1

<400> SEQUENCE: 25

```
gtcactgcct ttctggggga gagggtcaca ctgacatctt actggaggag agtgagcctg      60
ggccccgaga tcgaggtgtc ttggttcaag ctgggacctg agaggagca ggtgctgatc     120
ggcaggatgc accacgacgt gatcttcatc gagtggccct tcgggggctt ctttgatatc     180
caccgctccg ccaacacatt ctttctggtg gtgaccgccg ccaacatctc tcacgacggc     240
aattatctgt gcaggatgaa gctgggcgag acagaggtga ccaagcagga gcacctgagc     300
gtggtgaagc cactgaccct gtctgtgcac agcgagcggt cccagttccc cgattttccc     360
gtgctgaccg tgacatgtac cgtgaacgcc tttccccacc ctcacgtgca gtggctgatg     420
cctgagggag tggagccagc accaacagca gcaaatggcg gcgtgatgaa ggagaaggac     480
ggcagcctgt ccgtggccgt ggatctgagc ctgcctaagc catggcacct gccagtgacc     540
tgcgtcggaa agaacgataa ggaggaagca cacggagtct atgtcagtgg ctacctgtca     600
cag                                                                  603
```

<210> SEQ ID NO 26
<211> LENGTH: 201
<212> TYPE: PRT
<213> ORGANISM: Artificial Sequence
<220> FEATURE:
<223> OTHER INFORMATION: Chemically synthesized, BARF1

<400> SEQUENCE: 26

```
Val Thr Ala Phe Leu Gly Glu Arg Val Thr Leu Thr Ser Tyr Trp Arg
1               5                   10                  15

Arg Val Ser Leu Gly Pro Glu Ile Glu Val Ser Trp Phe Lys Leu Gly
            20                  25                  30

Pro Gly Glu Glu Gln Val Leu Ile Gly Arg Met His His Asp Val Ile
        35                  40                  45

Phe Ile Glu Trp Pro Phe Arg Gly Phe Phe Asp Ile His Arg Ser Ala
    50                  55                  60

Asn Thr Phe Phe Leu Val Val Thr Ala Ala Asn Ile Ser His Asp Gly
65                  70                  75                  80

Asn Tyr Leu Cys Arg Met Lys Leu Gly Glu Thr Glu Val Thr Lys Gln
                85                  90                  95

Glu His Leu Ser Val Val Lys Pro Leu Thr Leu Ser Val His Ser Glu
            100                 105                 110

Arg Ser Gln Phe Pro Asp Phe Ser Val Leu Thr Val Thr Cys Thr Val
        115                 120                 125

Asn Ala Phe Pro His Pro His Val Gln Trp Leu Met Pro Glu Gly Val
    130                 135                 140

Glu Pro Ala Pro Thr Ala Ala Asn Gly Gly Val Met Lys Glu Lys Asp
145                 150                 155                 160

Gly Ser Leu Ser Val Ala Val Asp Leu Ser Leu Pro Lys Pro Trp His
                165                 170                 175

Leu Pro Val Thr Cys Val Gly Lys Asn Asp Lys Glu Glu Ala His Gly
            180                 185                 190

Val Tyr Val Ser Gly Tyr Leu Ser Gln
        195                 200
```

<210> SEQ ID NO 27
<211> LENGTH: 957
<212> TYPE: DNA
<213> ORGANISM: Artificial Sequence
<220> FEATURE:
<223> OTHER INFORMATION: Chemically synthesized, EBNA1

<400> SEQUENCE: 27

```
atgagcgacg aaggacctgg aactggacct gggaacggac tggggcagaa ggaagataca      60
agcggacctg aggggagcgg gggcagcggc cctcagagga gaggcggcga caaccacggc     120
cgccctggag caccaggcgg cagcggctcc ggcccacggc accgcgatgg cgtgcggcgc     180
ccccagaaga ggccttcttg catcggctgt aagggagcac acggcggaac cccaggcagg     240
aggcccttct tccaccctgt gggagaggca gactacttcg agtatcacca ggagggcggc     300
ccagacggag agccagatgt gccccctggc gccatcgagc agggacctgc agacgatcca     360
ggagcaggac ccgccacagg ccctagaggc agggcgatg cgggccggcg caagaagggc     420
ggctggttcg gcaagcacag ggacagggc ggctccaacc ccaagtttga aatatcgca      480
gagggcctga gggtgctgct ggcaagatct cacgtggagc ggaccacaga ggagggaaac     540
tgggtggcag gcgtgttcgt gtacggcgga tctaagacca gcctgtataa tctgaggaga     600
ggaatcgccc tggcaatccc tcagtgcagg ctgacaccac tgagcaggct gcccttcggc     660
atggcaccag gacctggacc acagccagga cctctgaggg agtccatcgt gtgctacttc     720
atggtgtttc tgcagaccca catctttgcc gaggtgctga aggacgccat caaggacctg     780
gtcatgacca gccagccccc cacatgcaat atcaaggtga ccgtgtgctc cttcgacgat     840
ggcgtggacc tgccaccctg gtttcctcca atggtggagg cgctgccgc cgagggcgat     900
gatggcgacg atggcgacga gggaggcgac ggagatgaag agaggagg acaggaa         957
```

<210> SEQ ID NO 28
<211> LENGTH: 319
<212> TYPE: PRT
<213> ORGANISM: Artificial Sequence
<220> FEATURE:
<223> OTHER INFORMATION: Chemically synthesized, EBNA1

<400> SEQUENCE: 28

```
Met Ser Asp Glu Gly Pro Gly Thr Gly Pro Gly Asn Gly Leu Gly Gln
1               5                   10                  15

Lys Glu Asp Thr Ser Gly Pro Glu Gly Ser Gly Ser Gly Pro Gln
            20                  25                  30

Arg Arg Gly Gly Asp Asn His Gly Arg Pro Gly Ala Pro Gly Gly Ser
        35                  40                  45

Gly Ser Gly Pro Arg His Arg Asp Gly Val Arg Arg Pro Gln Lys Arg
    50                  55                  60

Pro Ser Cys Ile Gly Cys Lys Gly Ala His Gly Thr Pro Gly Arg
65                  70                  75                  80

Arg Pro Phe Phe His Pro Val Gly Glu Ala Asp Tyr Phe Glu Tyr His
                85                  90                  95

Gln Glu Gly Gly Pro Asp Gly Glu Pro Asp Val Pro Pro Gly Ala Ile
            100                 105                 110

Glu Gln Gly Pro Ala Asp Asp Pro Gly Ala Gly Pro Ala Thr Gly Pro
        115                 120                 125

Arg Gly Gln Gly Asp Gly Gly Arg Arg Lys Lys Gly Gly Trp Phe Gly
```

```
                130               135                140
Lys His Arg Gly Gln Gly Gly Ser Asn Pro Lys Phe Glu Asn Ile Ala
145                 150                 155                 160

Glu Gly Leu Arg Val Leu Leu Ala Arg Ser His Val Glu Arg Thr Thr
            165                 170                 175

Glu Glu Gly Asn Trp Val Ala Gly Val Phe Val Tyr Gly Gly Ser Lys
                180                 185                 190

Thr Ser Leu Tyr Asn Leu Arg Arg Gly Ile Ala Leu Ala Ile Pro Gln
            195                 200                 205

Cys Arg Leu Thr Pro Leu Ser Arg Leu Pro Phe Gly Met Ala Pro Gly
        210                 215                 220

Pro Gly Pro Gln Pro Gly Pro Leu Arg Glu Ser Ile Val Cys Tyr Phe
225                 230                 235                 240

Met Val Phe Leu Gln Thr His Ile Phe Ala Glu Val Leu Lys Asp Ala
                245                 250                 255

Ile Lys Asp Leu Val Met Thr Lys Pro Ala Pro Thr Cys Asn Ile Lys
            260                 265                 270

Val Thr Val Cys Ser Phe Asp Asp Gly Val Asp Leu Pro Pro Trp Phe
        275                 280                 285

Pro Pro Met Val Glu Gly Ala Ala Glu Gly Asp Asp Gly Asp Asp
290                 295                 300

Gly Asp Glu Gly Gly Asp Gly Asp Glu Gly Glu Glu Gly Gln Glu
305                 310                 315

<210> SEQ ID NO 29
<211> LENGTH: 1491
<212> TYPE: DNA
<213> ORGANISM: Artificial Sequence
<220> FEATURE:
<223> OTHER INFORMATION: Chemically synthesized, LMP2A

<400> SEQUENCE: 29
atgggcagcc tggagatggt gcccatggga gcaggccctc cctcccctgg cggcgaccca      60
gatggcgacg atggcggaaa caatagccag tacccatctg ccagcggaag ctccggaaac     120
accccaacac cacccaatga cgaggagagg gagtccaacg aggagccagc agcaccatac     180
gaggatcctt attggggcaa tggcgacagg cactccgatt ccagccact gggcacccag      240 gaccagtctc tgtttctggg cctgcagcac gacggaaacg atggcctgcc tgcagcacca     300
tactctccca gagacgattc tagccagcac atcttcgagg aggcaggaag gggaagcatg     360
aatcccgtgt gcctgcctgt gatcgtggcc cctatctgt tctggctggc agcaatcgca      420
gcatcctgct ttacagcctc cgtgtctacc gtggtgaccg caacaggcct ggccctgtct     480
ctgctgctgc tggcagcagt ggcatcctct tatgctgccg cccagagaaa gctgctgacc     540
ccagtgacag tgctgaccgc cgtggtgaca ttctttgcca tctgtctgac ctggcggatc     600
gaggaccctc cattcaacag cctgctgttt gcactgctgg ccgccgcgg cggcctgcag      660 ggcatctacg tgctggtcat gctggtgctg ctgatcctgg cctataggag acggtggcgc     720 aggctgacccg tgtgcggcgg aatcatgttc ctggcctgcg tgctggtgct gatcgtggat     780
gccgtgctgc agctgtctcc cctgctggga gcagtgacag tggtgagcat gaccctgctg     840
ctgctggcct ttgtgctgtg ctgagctcc cctggcggcc tgggcacact gggagccgcc     900
ctgctgaccc tggccgccgc cctggccctg ctggcatccc tgatcctggg cacactgaat     960
ctgaccacaa tgttcctgct gatgctgctg tggaccctgg tggtgctgct gatctgctct    1020
```

```
agctgttcct cttgccccct gtctaagatc ctgctggcaa ggctgttcct gtacgcactg    1080
gccctgctgc tgctggcaag cgccctgatc gccggcggat ccatcctgca gacaaacttt    1140
aagtctctga gctccaccga gttcatccca aatctgtttt gtatgctgct gctgatcgtg    1200
gccggcatcc tgttcatcct ggccatcctg acagagtggg gcagcggcaa cagaacctat    1260
ggccccgtgt ttatgtgcct gggcggcctg ctgacaatgg tggcaggagc cgtgtggctg    1320
accgtgatga ccaatacact gctgagcgcc tggatcctga cagccggctt cctgatcttt    1380
ctgatcggct tcgccctgtt tggcgtgatc agatgctgtc ggtactgctg ttactattgc    1440 ctgacccctgg agtccgagga gaggcctccc acaccttata ggaacaccgt g            1491
```

<210> SEQ ID NO 30
<211> LENGTH: 497
<212> TYPE: PRT
<213> ORGANISM: Artificial Sequence
<220> FEATURE:
<223> OTHER INFORMATION: Chemically synthesized, LMP2A

<400> SEQUENCE: 30

```
Met Gly Ser Leu Glu Met Val Pro Met Gly Ala Gly Pro Ser Pro
1               5                   10                  15

Gly Gly Asp Pro Asp Gly Asp Gly Gly Asn Asn Ser Gln Tyr Pro
                20                  25                  30

Ser Ala Ser Gly Ser Ser Gly Asn Thr Pro Thr Pro Pro Asn Asp Glu
            35                  40                  45

Glu Arg Glu Ser Asn Glu Glu Pro Ala Ala Pro Tyr Glu Asp Pro Tyr
        50                  55                  60

Trp Gly Asn Gly Asp Arg His Ser Asp Phe Gln Pro Leu Gly Thr Gln
65                  70                  75                  80

Asp Gln Ser Leu Phe Leu Gly Leu Gln His Asp Gly Asn Asp Gly Leu
                85                  90                  95

Pro Ala Ala Pro Tyr Ser Pro Arg Asp Asp Ser Ser Gln His Ile Phe
            100                 105                 110

Glu Glu Ala Gly Arg Gly Ser Met Asn Pro Val Cys Leu Pro Val Ile
        115                 120                 125

Val Ala Pro Tyr Leu Phe Trp Leu Ala Ala Ile Ala Ala Ser Cys Phe
130                 135                 140

Thr Ala Ser Val Ser Thr Val Val Thr Ala Thr Gly Leu Ala Leu Ser
145                 150                 155                 160

Leu Leu Leu Leu Ala Ala Val Ala Ser Ser Tyr Ala Ala Ala Gln Arg
                165                 170                 175

Lys Leu Leu Thr Pro Val Thr Val Leu Thr Ala Val Val Thr Phe Phe
            180                 185                 190

Ala Ile Cys Leu Thr Trp Arg Ile Glu Asp Pro Pro Phe Asn Ser Leu
        195                 200                 205

Leu Phe Ala Leu Leu Ala Ala Ala Gly Gly Leu Gln Gly Ile Tyr Val
    210                 215                 220

Leu Val Met Leu Val Leu Leu Ile Leu Ala Tyr Arg Arg Arg Trp Arg
225                 230                 235                 240

Arg Leu Thr Val Cys Gly Gly Ile Met Phe Leu Ala Cys Val Leu Val
                245                 250                 255

Leu Ile Val Asp Ala Val Leu Gln Leu Ser Pro Leu Leu Gly Ala Val
            260                 265                 270

Thr Val Val Ser Met Thr Leu Leu Leu Leu Ala Phe Val Leu Trp Leu
        275                 280                 285
```

```
Ser Ser Pro Gly Gly Leu Gly Thr Leu Gly Ala Ala Leu Leu Thr Leu
    290                 295                 300
Ala Ala Ala Leu Ala Leu Leu Ala Ser Leu Ile Leu Gly Thr Leu Asn
305                 310                 315                 320
Leu Thr Thr Met Phe Leu Leu Met Leu Leu Trp Thr Leu Val Val Leu
                325                 330                 335
Leu Ile Cys Ser Ser Cys Ser Ser Cys Pro Leu Ser Lys Ile Leu Leu
                340                 345                 350
Ala Arg Leu Phe Leu Tyr Ala Leu Ala Leu Leu Leu Leu Ala Ser Ala
            355                 360                 365
Leu Ile Ala Gly Gly Ser Ile Leu Gln Thr Asn Phe Lys Ser Leu Ser
    370                 375                 380
Ser Thr Glu Phe Ile Pro Asn Leu Phe Cys Met Leu Leu Leu Ile Val
385                 390                 395                 400
Ala Gly Ile Leu Phe Ile Leu Ala Ile Leu Thr Glu Trp Gly Ser Gly
                405                 410                 415
Asn Arg Thr Tyr Gly Pro Val Phe Met Cys Leu Gly Gly Leu Leu Thr
            420                 425                 430
Met Val Ala Gly Ala Val Trp Leu Thr Val Met Thr Asn Thr Leu Leu
    435                 440                 445
Ser Ala Trp Ile Leu Thr Ala Gly Phe Leu Ile Phe Leu Ile Gly Phe
450                 455                 460
Ala Leu Phe Gly Val Ile Arg Cys Cys Arg Tyr Cys Cys Tyr Tyr Cys
465                 470                 475                 480
Leu Thr Leu Glu Ser Glu Glu Arg Pro Pro Thr Pro Tyr Arg Asn Thr
            485                 490                 495
Val

<210> SEQ ID NO 31
<211> LENGTH: 1041
<212> TYPE: DNA
<213> ORGANISM: Artificial Sequence
<220> FEATURE:
<223> OTHER INFORMATION: Chemically synthesized, LMP1TT30

<400> SEQUENCE: 31
atggactgga cttggattct gtttctggtc gccgccgcca cacgggtgca tagtgactgg      60
actggagggg ctctgctggt gctgtattcc ttcgccctga tgctgatcat catcatcctg     120
atcatcttca tctttaggag agatctgctg tgcccactgg cgccctgtg cctgctgctg      180 ctgatgatca ccctgctgct gatcgccctg tggaacctgc tgctgggcct gtggatctat     240
ctgctggaga tcctgtggag gctgggagca accatcggc agctgctggc cttctttctg      300
gccttctttc tggatctgat cctgctgatc atcgccctgt acctgcagca gaattggtgg     360
acactgctgg tggacctgct gtggctgctg ctgtttctgg ccatcctgat ctggatgtac     420
tatcacggac agaggcactc cgacgagcac caccacgacg attctctgcc tcacctgcag     480
ctggcagcag acgattctgg ccacgagagc gactccaact ctaatgaggg ccgccaccac     540
ctgctggtga cgagccgg cgatggccct ccctgtgct cccagaacct gggagcacct       600
ggcggcggcc ccgacaatgg cccacaggac cccgataaca ccgacgataa tggccctcag     660
gacccagata acacagacga taatggcccc caggaccctg acaataccga cgataacgga     720
cctcaggatc ccgacaatac agacgataat ggccctcacg atccctgcc tcacaaccca      780 agcgactccg ccggaaacga tggcggccca cccaatctga ccgaggaggt ggagaataag     840
```

```
ggcggcgacc ggggcctcc atctatgaca gacggcggcg gcggcgaccc ccacctgcca    900
accctgctgc tgggcacatc tggaagcggc ggcgacgatg acgatccaca cggacctgtg    960
cagctgagcg gctatgactt caataatttc acagtctcat tttggctgcg agtgcctaaa   1020
gtgtctgcct ctcatctgga g                                              1041
```

<210> SEQ ID NO 32
<211> LENGTH: 347
<212> TYPE: PRT
<213> ORGANISM: Artificial Sequence
<220> FEATURE:
<223> OTHER INFORMATION: Chemically synthesized, LMP1TT30

<400> SEQUENCE: 32

```
Asp Trp Thr Gly Gly Ala Leu Leu Val Leu Tyr Ser Phe Ala Leu Met
1               5                   10                  15

Leu Ile Ile Ile Ile Leu Ile Ile Phe Ile Phe Arg Arg Asp Leu Leu
            20                  25                  30

Cys Pro Leu Gly Ala Leu Cys Leu Leu Leu Met Ile Thr Leu Leu
        35                  40                  45

Leu Ile Ala Leu Trp Asn Leu His Gly Gln Ala Leu Tyr Leu Gly Ile
    50                  55                  60

Val Leu Phe Ile Phe Gly Cys Leu Leu Val Leu Gly Leu Trp Ile Tyr
65                  70                  75                  80

Leu Leu Glu Ile Leu Trp Arg Leu Gly Ala Thr Ile Trp Gln Leu Leu
                85                  90                  95

Ala Phe Phe Leu Ala Phe Phe Leu Asp Leu Ile Leu Leu Ile Ile Ala
            100                 105                 110

Leu Tyr Leu Gln Gln Asn Trp Trp Thr Leu Leu Val Asp Leu Leu Trp
        115                 120                 125

Leu Leu Leu Phe Leu Ala Ile Leu Ile Trp Met Tyr Tyr His Gly Gln
    130                 135                 140

Arg His Ser Asp Glu His His His Asp Asp Ser Leu Pro His Leu Gln
145                 150                 155                 160

Leu Ala Ala Asp Asp Ser Gly His Glu Ser Asp Ser Asn Ser Asn Glu
                165                 170                 175

Gly Arg His His Leu Leu Val Ser Gly Ala Gly Asp Gly Pro Pro Leu
            180                 185                 190

Cys Ser Gln Asn Leu Gly Ala Pro Gly Gly Gly Pro Asp Asn Gly Pro
        195                 200                 205

Gln Asp Pro Asp Asn Thr Asp Asp Asn Gly Pro Gln Asp Pro Asp Asn
    210                 215                 220

Thr Asp Asp Asn Gly Pro Gln Asp Pro Asp Asn Thr Asp Asp Asn Gly
225                 230                 235                 240

Pro Gln Asp Pro Asp Asn Thr Asp Asp Asn Gly Pro His Asp Pro Leu
                245                 250                 255

Pro His Asn Pro Ser Asp Ser Ala Gly Asn Asp Gly Gly Pro Pro Asn
            260                 265                 270

Leu Thr Glu Glu Val Glu Asn Lys Gly Gly Asp Arg Gly Pro Pro Ser
        275                 280                 285

Met Thr Asp Gly Gly Gly Gly Asp Pro His Leu Pro Thr Leu Leu Leu
    290                 295                 300

Gly Thr Ser Gly Ser Gly Gly Asp Asp Asp Pro His Gly Pro Val
305                 310                 315                 320
```

```
Gln Leu Ser Gly Tyr Asp Phe Asn Asn Phe Thr Val Ser Phe Trp Leu
            325                 330                 335
Arg Val Pro Lys Val Ser Ala Ser His Leu Glu
            340                 345

<210> SEQ ID NO 33
<211> LENGTH: 18
<212> TYPE: PRT
<213> ORGANISM: Artificial Sequence
<220> FEATURE:
<223> OTHER INFORMATION: Chemically synthesized, IgE leader sequence

<400> SEQUENCE: 33

Met Asp Trp Thr Trp Ile Leu Phe Leu Val Ala Ala Ala Thr Arg Val
1               5                   10                  15
His Ser

<210> SEQ ID NO 34
<211> LENGTH: 20
<212> TYPE: PRT
<213> ORGANISM: Artificial Sequence
<220> FEATURE:
<223> OTHER INFORMATION: Chemically synthesized, gp350 leader sequence

<400> SEQUENCE: 34

Met Glu Ala Ala Leu Leu Val Cys Gln Tyr Thr Ile Gln Ser Leu Ile
1               5                   10                  15
His Leu Thr Gly
            20

<210> SEQ ID NO 35
<211> LENGTH: 33
<212> TYPE: PRT
<213> ORGANISM: Artificial Sequence
<220> FEATURE:
<223> OTHER INFORMATION: Chemically synthesized, gp42 leader sequence

<400> SEQUENCE: 35

Met Val Ser Phe Lys Gln Val Arg Val Pro Leu Phe Thr Ala Ile Ala
1               5                   10                  15
Leu Val Ile Val Leu Leu Leu Ala Tyr Phe Leu Pro Pro Arg Val Arg
            20                  25                  30
Gly

<210> SEQ ID NO 36
<211> LENGTH: 22
<212> TYPE: PRT
<213> ORGANISM: Artificial Sequence
<220> FEATURE:
<223> OTHER INFORMATION: Chemically synthesized, gL leader sequence

<400> SEQUENCE: 36

Met Arg Ala Val Gly Val Phe Leu Ala Thr Cys Leu Val Thr Ile Phe
1               5                   10                  15
Val Leu Pro Thr Trp Gly
            20

<210> SEQ ID NO 37
<211> LENGTH: 18
<212> TYPE: PRT
<213> ORGANISM: Artificial Sequence
<220> FEATURE:
<223> OTHER INFORMATION: Chemically synthesized, gH leader sequence
```

```
<400> SEQUENCE: 37

Met Gln Leu Leu Cys Val Phe Cys Leu Val Leu Leu Trp Glu Val Gly
1               5                   10                  15

Ala Ala

<210> SEQ ID NO 38
<211> LENGTH: 22
<212> TYPE: PRT
<213> ORGANISM: Artificial Sequence
<220> FEATURE:
<223> OTHER INFORMATION: Chemically synthesized, gB leader sequence

<400> SEQUENCE: 38

Met Thr Arg Arg Arg Val Leu Ser Val Val Leu Leu Ala Ala Leu
1               5                   10                  15

Ala Cys Arg Leu Gly Ala
            20

<210> SEQ ID NO 39
<211> LENGTH: 32
<212> TYPE: PRT
<213> ORGANISM: Artificial Sequence
<220> FEATURE:
<223> OTHER INFORMATION: Chemically synthesized, gN leader sequence

<400> SEQUENCE: 39

Met Gly Lys Val Leu Arg Lys Pro Phe Ala Lys Ala Val Pro Leu Leu
1               5                   10                  15

Phe Leu Ala Ala Thr Trp Leu Leu Thr Gly Val Leu Pro Ala Gly Ala
            20                  25                  30

<210> SEQ ID NO 40
<211> LENGTH: 28
<212> TYPE: PRT
<213> ORGANISM: Artificial Sequence
<220> FEATURE:
<223> OTHER INFORMATION: Chemically synthesized, BDLF3 leader sequence

<400> SEQUENCE: 40

Met Ala His Ala Arg Asp Lys Ala Gly Ala Val Leu Ala Met Ile Leu
1               5                   10                  15

Ile Cys Glu Thr Ser Leu Ile Trp Thr Ser Ser Gly
            20                  25

<210> SEQ ID NO 41
<211> LENGTH: 17
<212> TYPE: PRT
<213> ORGANISM: Artificial Sequence
<220> FEATURE:
<223> OTHER INFORMATION: Chemically synthesized, BILF2 leader sequence

<400> SEQUENCE: 41

Met Thr His Leu Val Leu Leu Leu Cys Cys Cys Val Gly Ser Val Cys
1               5                   10                  15

Ala

<210> SEQ ID NO 42
<211> LENGTH: 23
<212> TYPE: PRT
<213> ORGANISM: Artificial Sequence
<220> FEATURE:
<223> OTHER INFORMATION: Chemically synthesized, BILF1 leader sequence

<400> SEQUENCE: 42
```

```
Met Leu Ser Thr Met Ala Pro Gly Ser Thr Val Gly Thr Leu Val Ala
1               5                   10                  15

Asn Met Thr Ser Val Asn Ala
            20

<210> SEQ ID NO 43
<211> LENGTH: 20
<212> TYPE: PRT
<213> ORGANISM: Artificial Sequence
<220> FEATURE:
<223> OTHER INFORMATION: Chemically synthesized, BARF1 leader sequence

<400> SEQUENCE: 43

Met Ala Arg Phe Ile Ala Gln Leu Leu Leu Ala Ser Cys Val Ala
1               5                   10                  15

Ala Gly Gln Ala
            20
```

EPSTEIN-BARR VIRUS NUCLEIC ACID CONSTRUCTS AND VACCINES MADE THEREFROM, AND METHODS OF USING SAME

CROSS-REFERENCE TO RELATED APPLICATIONS

This application is the U.S. national phase application filed under 35 U.S.C. § 371 claiming benefit to International Patent Application No. PCT/US2019/018159, filed Feb. 15, 2019, which claims priority to and the benefit of U.S. Provisional Application No. 62/710,396, filed Feb. 16, 2018, the disclosures of which are hereby incorporated by reference herein in their entireties.

FIELD OF THE INVENTION

The present invention relates to vaccines for inducing immune responses and treating individuals infected with Epstein-Barr virus (EBV) and/or treating or preventing an EBV associated disease. The present invention relates to consensus EBV glycoprotein antigens and latent stage EBV protein antigens and nucleic acid molecules which encode the same.

BACKGROUND OF THE INVENTION

Epstein-Barr virus (EBV), also known as human herpesvirus 4 (HHV4), is a member of the herpes virus family. It is one of the most common human viruses and infects 95% of the population. EBV can cause or is associated with several diseases including post-transplant lymphoproliferative disease (PTLD), infectious mononucleosis (mono), and autoimmune diseases, and is linked to 2% of all human cancers.

Currently there are no FDA approved vaccines against EBV. Therefore, there is need in the art for prophylactic and therapeutic vaccines against EBV and EBV associated diseases. The current invention satisfies this unmet need.

SUMMARY OF THE INVENTION

In one embodiment, the invention relates to an immunogenic composition comprising a nucleic acid molecule encoding at least one Epstein-Barr virus (EBV) antigen. In one embodiment, at least one EBV antigen is an EBV glycoprotein antigen, or a latent-stage EBV antigen.

In one embodiment, the immunogenic composition comprises at least one nucleotide sequence encoding at least one EBV glycoprotein antigen. In one embodiment, at least one EBV glycoprotein antigen is gp350, gp42, gL, gH, gB, gM, gN, BDLF2, BDLF3, BILF1, BILF2, BARF1 or a combination thereof.

In one embodiment, the immunogenic composition comprises at least one nucleotide sequence encoding at least one latent-stage EBV antigen. In one embodiment, at least one latent-stage EBV antigen is EBNA1, LMP1, LMP2A or a combination thereof.

In one embodiment, the antigen comprises at least one mutation that disrupts at least one function of a native EBV antigen. In one embodiment, at least one function is selected from the group consisting of DNA replication, mitotic segregation, transcriptional activation, autoregulation, and suppression of the lytic cycle.

In one embodiment, the antigen is an EBNA1 antigen comprising at least one mutation selected from the group consisting of Δ41-52, Δ90-309, mutation of amino acid E444, and mutation of amino acid S446 relative to the native antigen sequence.

In one embodiment, the antigen is an LMP1 antigen comprising at least one mutation at an amino acid residue selected from the group consisting of P204, Q206, T208 and Y369 relative to the native antigen sequence.

In one embodiment, the antigen is an LMP2A antigen comprising at least one mutation at an amino acid residue selected from the group consisting of P57, P58, Y74, Y85, P98, P99 and Y112 relative to the native antigen sequence.

In one embodiment, the nucleic acid molecule encodes a peptide comprising an amino acid sequence selected from a) an amino acid sequence having at least about 90% identity over an entire length of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, b) an immunogenic fragment comprising at least about 90% identity over at least 60% of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, c) an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, or d) an immunogenic fragment comprising at least 60% of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32.

In one embodiment, the nucleic acid molecule is a DNA molecule or a RNA molecule.

In one embodiment, the nucleic acid molecule comprises a nucleotide sequence of a) a nucleotide sequence having at least about 90% identity over an entire length of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, b) an immunogenic fragment of a nucleotide sequence having at least about 90% identity over at least 60% of the nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, c) a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ NO:31, or d) an immunogenic fragment of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ NO:31.

In one embodiment, the nucleotide sequence encoding the peptide is operably linked to at least one regulatory sequence selected from the group consisting of a start codon, a leader sequence, an IgE leader sequence and at least one stop codon.

In one embodiment, the nucleic acid molecule encodes a peptide comprising an amino acid sequence of a) an amino acid sequence having at least about 90% identity over an entire length of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, b) an immunogenic fragment comprising at least about 90% identity over at least 60% of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, c) an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, or d) an immunogenic fragment comprising at least 60% of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, operably linked to an amino acid sequence as set forth in SEQ ID NO:33.

In one embodiment, the nucleic acid molecule comprises a nucleotide sequence of a) a nucleotide sequence having at least about 90% identity over an entire length of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, b) an immunogenic fragment of a nucleotide sequence having at least about 90% identity over at least 60% of the nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, c) a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, or d) an immunogenic fragment of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, operably linked to an nucleotide sequence encoding SEQ ID NO:33.

In one embodiment, the nucleic acid molecule comprises an expression vector. In one embodiment, the nucleic acid molecule is incorporated into a viral particle.

In one embodiment, the immunogenic composition further comprises a pharmaceutically acceptable excipient. In one embodiment, the immunogenic composition further comprises an adjuvant.

In one embodiment, the invention relates to a nucleic acid molecule encoding a peptide comprising an amino acid sequence of a) an amino acid sequence having at least about 90% identity over an entire length of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, b) an immunogenic fragment comprising at least about 90% identity over at least 60% of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, c) an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, or d) an immunogenic fragment comprising at least 60% of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32.

In one embodiment, the nucleic acid molecule is a DNA molecule or an RNA molecule.

In one embodiment, the nucleic acid molecule comprises a nucleotide sequence of a) a nucleotide sequence having at least about 90% identity over an entire length of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, b) an immunogenic fragment of a nucleotide sequence having at least about 90% identity over at least 60% of the nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, c) a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, or d) an immunogenic fragment of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31.

In one embodiment, the nucleotide sequence encoding the peptide is operably linked to at least one regulatory sequence selected from the group consisting of a start codon, a leader sequence, an IgE leader sequence and at least one stop codon.

In one embodiment, the nucleic acid molecule encodes a peptide comprising an amino acid sequence of a) an amino acid sequence having at least about 90% identity over an entire length of the amino acid sequence selected from the group consisting of SEQ NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, b) an immunogenic fragment comprising at least about 90% identity over at least 60% of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, c) an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, or d) an immunogenic fragment comprising at least 60% of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, operably linked to an amino acid sequence as set forth in SEQ ID NO:33.

In one embodiment, the nucleic acid molecule comprises a nucleotide sequence of a) a nucleotide sequence having at least about 90% identity over an entire length of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, b) an immunogenic fragment of a nucleotide sequence having at least about 90% identity over at least 60% of the nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, c) a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, or d) an immunogenic fragment of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, operably linked to an nucleotide sequence encoding SEQ ID NO:33.

In one embodiment, the nucleic acid molecule comprises an expression vector. In one embodiment, the nucleic acid molecule is incorporated into a viral particle.

In one embodiment, the invention relates to an immunogenic composition comprising a peptide comprising an amino acid sequence of a) an amino acid sequence having at least about 90% identity over an entire length of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, b) an immunogenic fragment comprising at least about 90% identity over at least 60% of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, c) an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, or d) an immunogenic fragment comprising at least 60% of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32.

In one embodiment, the invention relates to a peptide comprising an amino acid sequence of a) an amino acid sequence having at least about 90% identity over an entire length of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, b) an immunogenic fragment comprising at least about 90% identity over at least 60% of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, c) an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, or d) an immunogenic fragment comprising at least 60% of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32.

In one embodiment, the invention relates to a method of inducing an immune response against an EBV antigen in a subject in need thereof, the method comprising administering an immunogenic composition comprising a nucleic acid molecule encoding at least one EBV antigen to the subject.

In one embodiment, the invention relates to a method of preventing EBV infection in a subject in need thereof, the method comprising administering an immunogenic composition comprising a nucleic acid molecule encoding at least one EBV antigen to the subject.

In one embodiment, the immunogenic composition comprises at least one nucleotide sequence encoding at least one EBV glycoprotein antigen. In one embodiment, at least one EBV glycoprotein antigen is selected from the group consisting of gp350, gp42, gL, gH, gB, gM, gN, BDLF2, BDLF3, BILF1, BILF2, and BARF1.

In one embodiment, the invention relates to a method of treating or preventing a disease or disorder associated with EBV latency in a subject in need thereof, the method comprising administering an immunogenic composition comprising a nucleic acid molecule encoding at least one EBV antigen to the subject.

In one embodiment, the immunogenic composition comprises at least one nucleotide sequence encoding at least one latent-stage EBV antigen. In one embodiment, at least one latent-stage EBV antigen is selected from the group consisting of EBNA1, LMP1, LMP2A and a combination thereof.

In one embodiment, the disease or disorder associated with EBV latency is at least one of Burkitt's lymphoma, Hodgkin lymphoma, Post-transplant lymphoma, T-cell lymphoma, AIDS-associated B-cell lymphoma, gastric carcinoma, nasopharyngeal carcinoma, infectious mononucleosis, or an autoimmune disease or disorder.

BRIEF DESCRIPTION OF DRAWINGS

FIG. 1 depicts a table of exemplary EBV associated cancers and diseases and the EBV antigens expressed.

FIG. 2 depicts a table of different exemplary cell types and the EBV antigens expressed. BL=Burkitt's lymphoma; NPC=nasopharyngeal carcinoma; CLL=chronic lymphocytic leukemia; LCL=lymphoblastoid cell line; EBNA=Epstein-Barr virus nuclear antigen; LMP=latent membrane protein; BARF1=BamHI A rightward frame 1.

FIG. 3 depicts a table of exemplary EBV associated cancers and diseases, percentage of the disease that are EBV positive, and the EBV antigens expressed.

FIG. 17, comprising FIG. 17A depicts a diagram of the EBNA1 protein. FIG. 17B depicts mutations that were incorporated into the optimized consensus EBNA1 protein to disrupt protein functions. FIG. 17C depicts mutations that were incorporated into the optimized consensus LMP1 protein to disrupt protein functions, FIG. 17D depicts mutations that were incorporated into the optimized consensus LMP2A protein to disrupt protein functions. FIG. 17E depicts an exemplary experimental design for immunization with EBNA1, LMP1 or LMP2A as individual vaccines. FIG. 17F depicts an exemplary experimental design for immunization with EBNA1, LMP1 and LMP2A as a triple vaccine.

DETAILED DESCRIPTION

Figure 4:
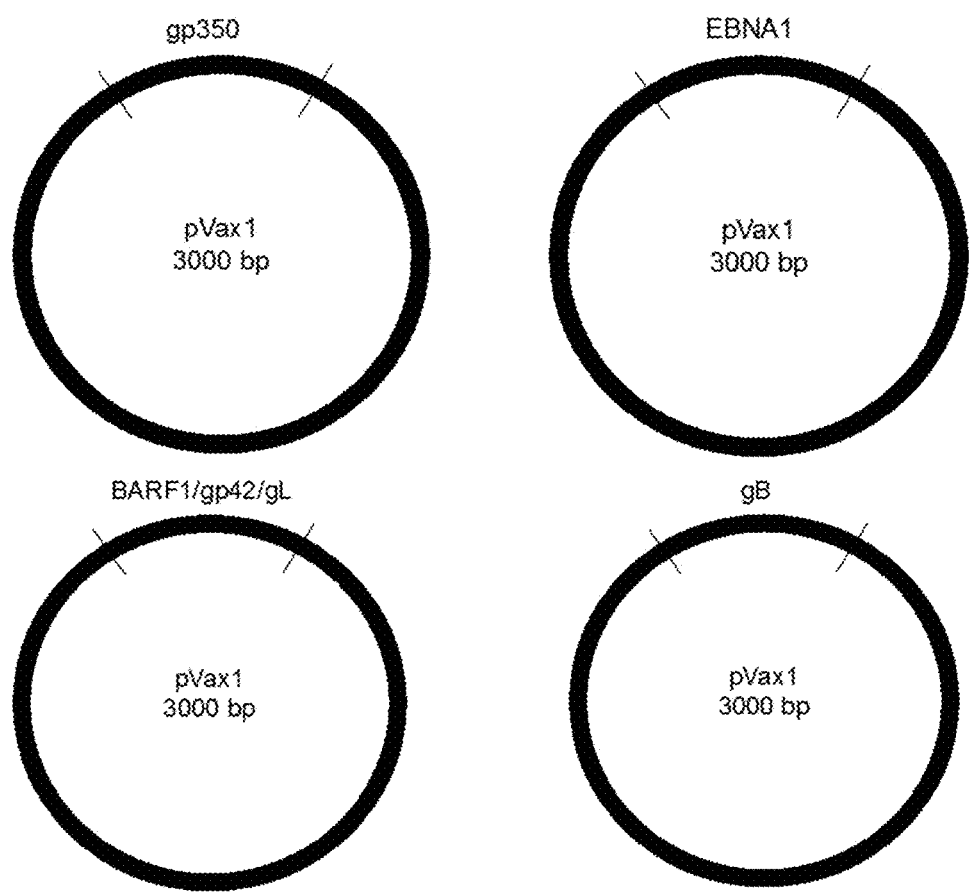
FIG. 4 depicts exemplary plasmid maps of expression plasmids for expression of one or multiple EBV antigens.
Figure 5:
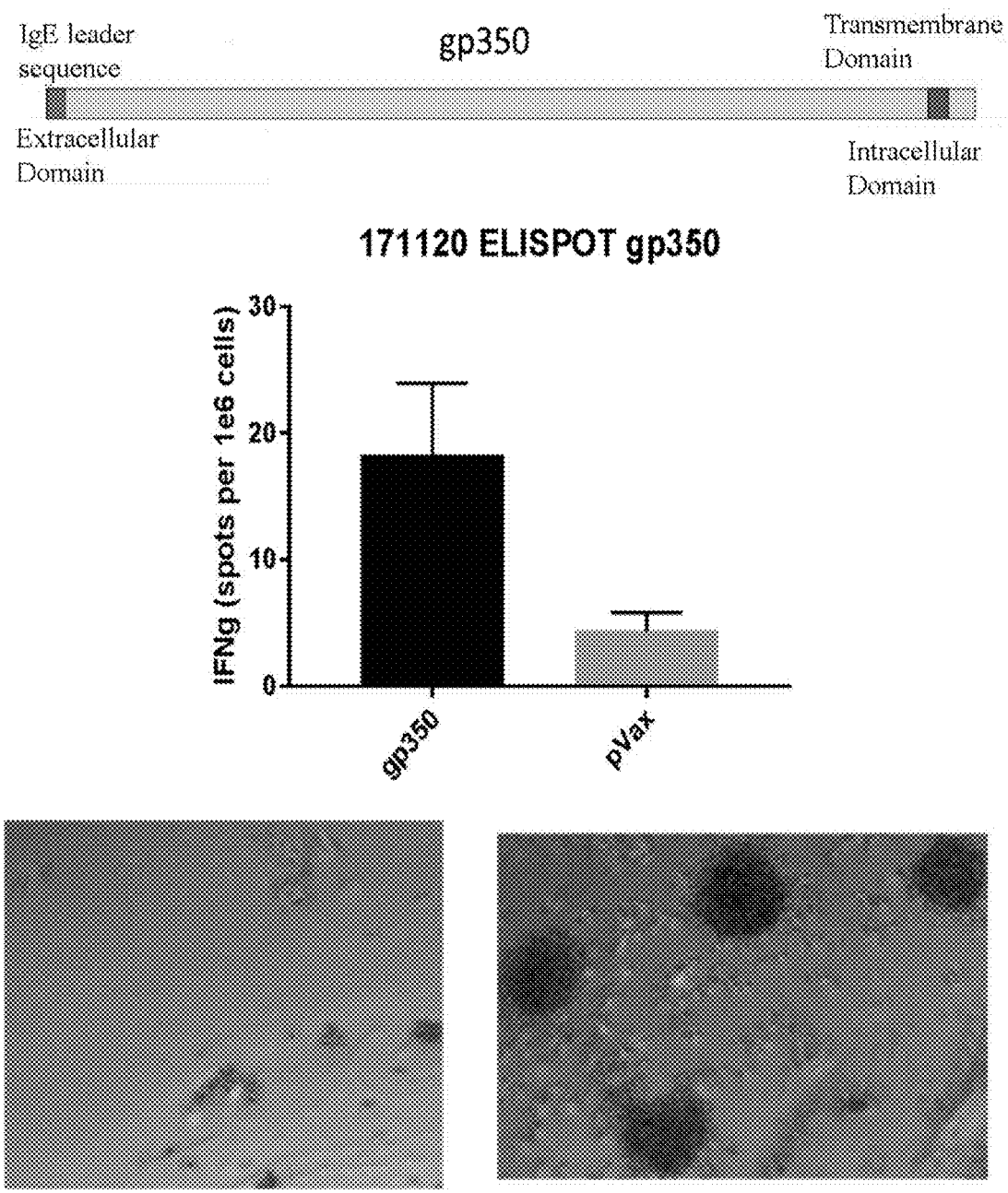
FIG. 5 depicts exemplary experimental data demonstrating that the gp350 vaccine was able to neutralize EBV infection in B cells. Primary B cells were co-cultured with sera from mice vaccinated with gp350 vaccine (lower left) or pVax (lower right), and EBV was added 1 h after the sera. Cell clumps appeared 4 to 7 days later. The formation of B cell clumps was visualized under the microscope, showing B cell EBV-induced malignant transformation.
Figure 6:
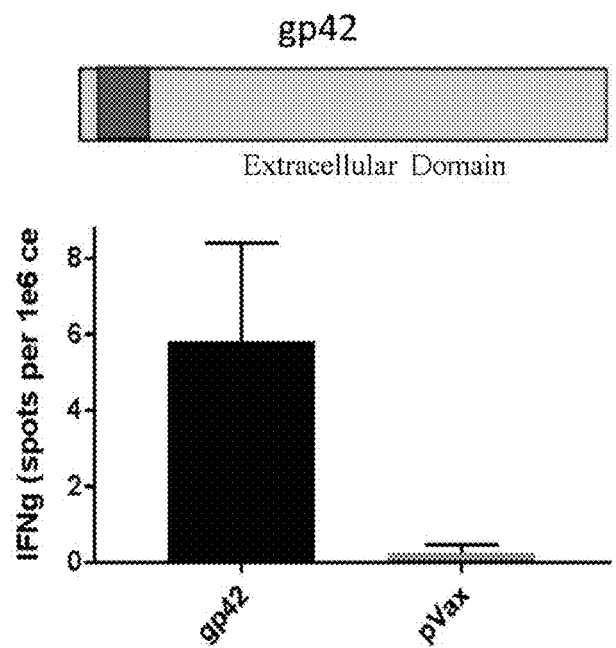
FIG. 6 depicts an exemplary Enzyme-Linked Immuno-Spot (ELISPOT) assay demonstrating an IFNγ response following immunization with optimized gp42.
Figure 7:
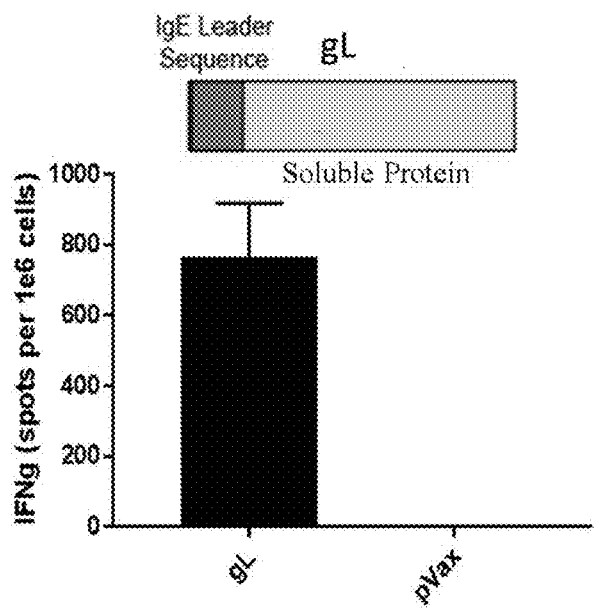
FIG. 7 depicts an exemplary ELISPOT assay demonstrating an IFNγ response following immunization with optimized gL.
Figure 8:
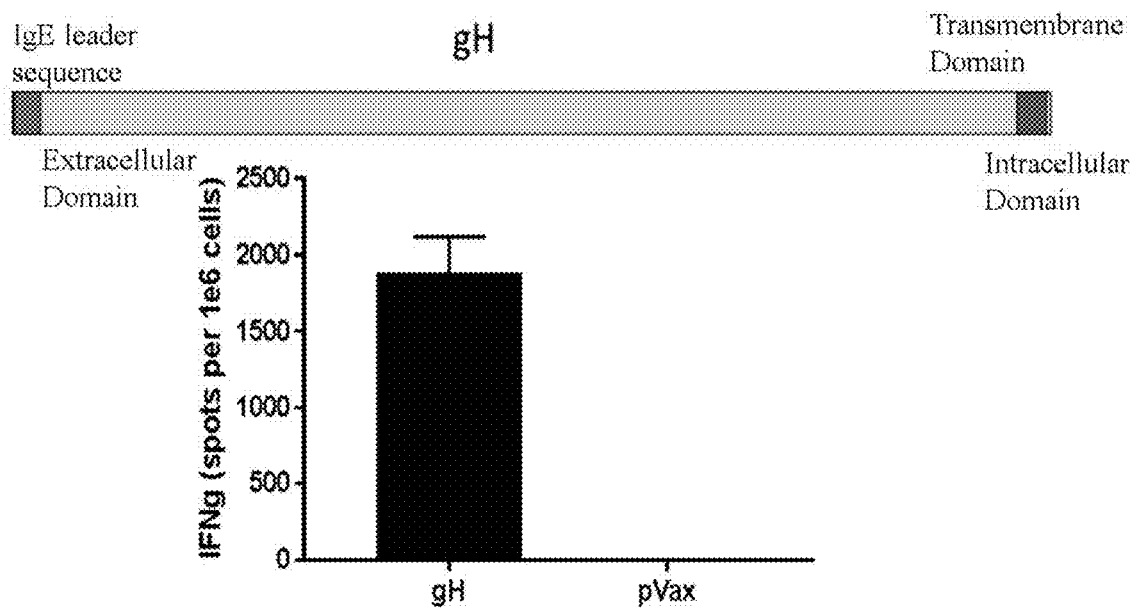
FIG. 8 depicts an exemplary ELISPOT assay demonstrating an IFNγ response following immunization with optimized gH.
Figure 9:
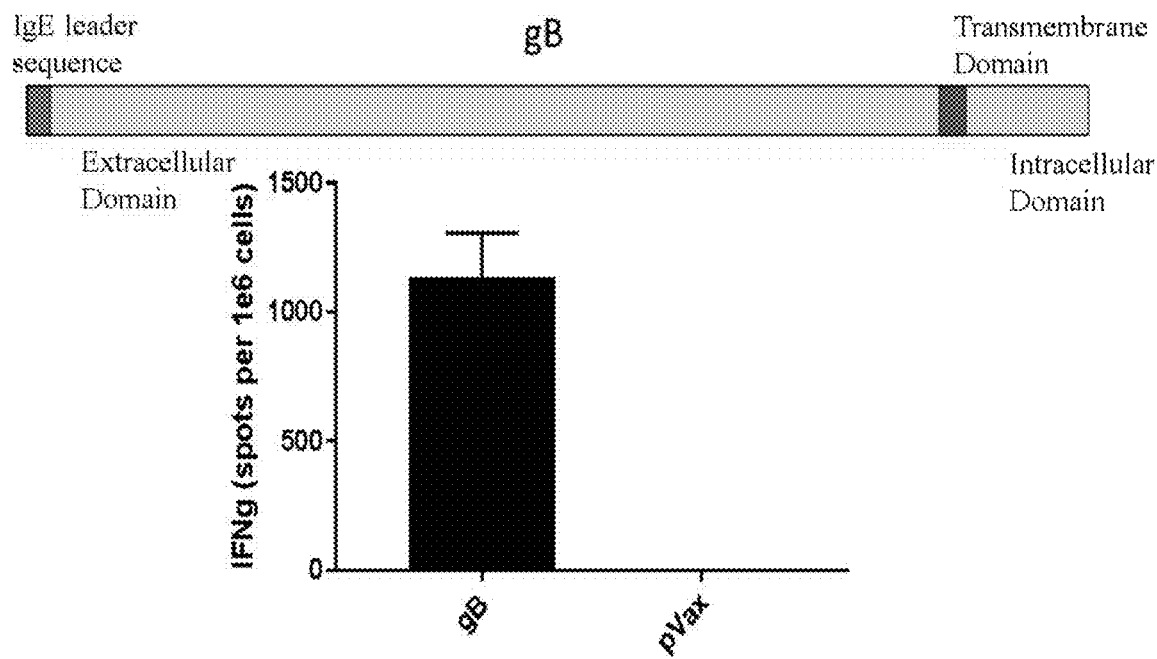
FIG. 9 depicts an exemplary ELISPOT assay demonstrating an IFNγ response following immunization with optimized gB.
Figure 10:
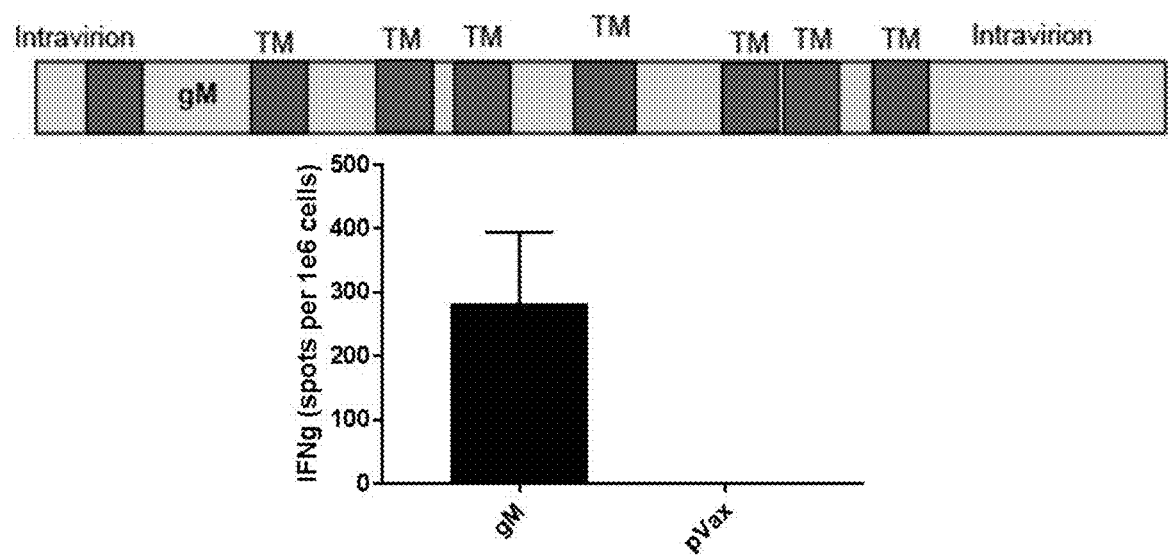
FIG. 10 depicts an exemplary ELISPOT assay demonstrating an IFNγ response following immunization with optimized gM.
Figure 11:
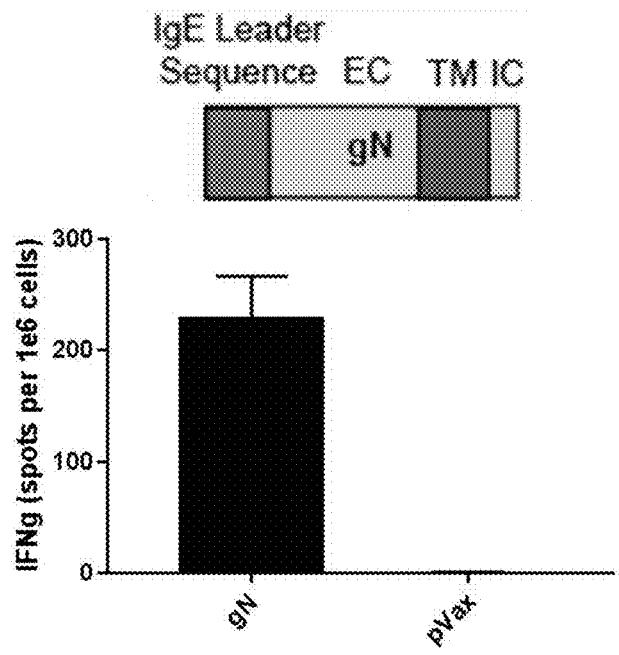
FIG. 11 depicts an exemplary ELISPOT assay demonstrating an IFNγ response following immunization with optimized gN.
Figure 12:
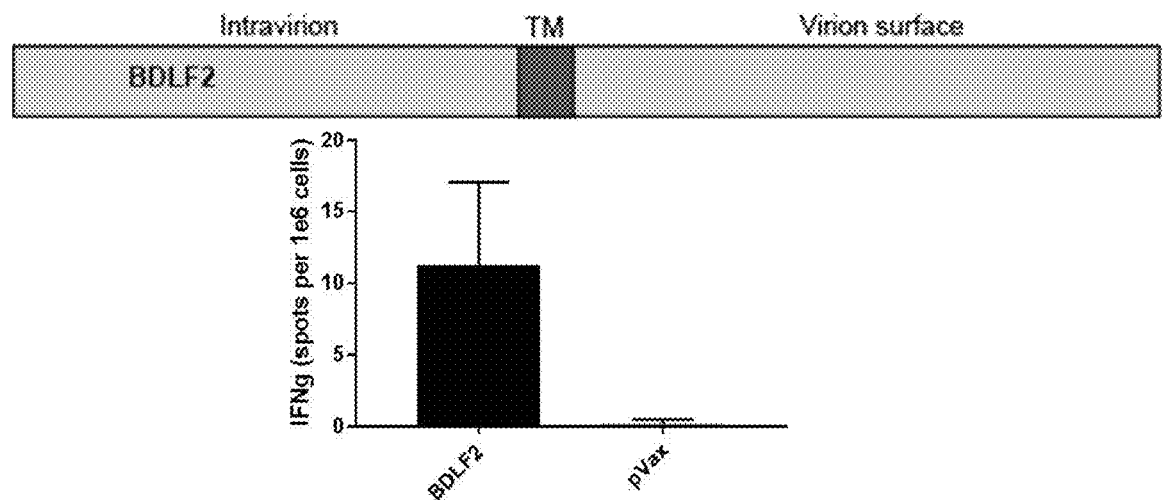
FIG. 12 depicts an exemplary ELISPOT assay demonstrating an IFNγ response following immunization with optimized BDLF2.
Figure 13:
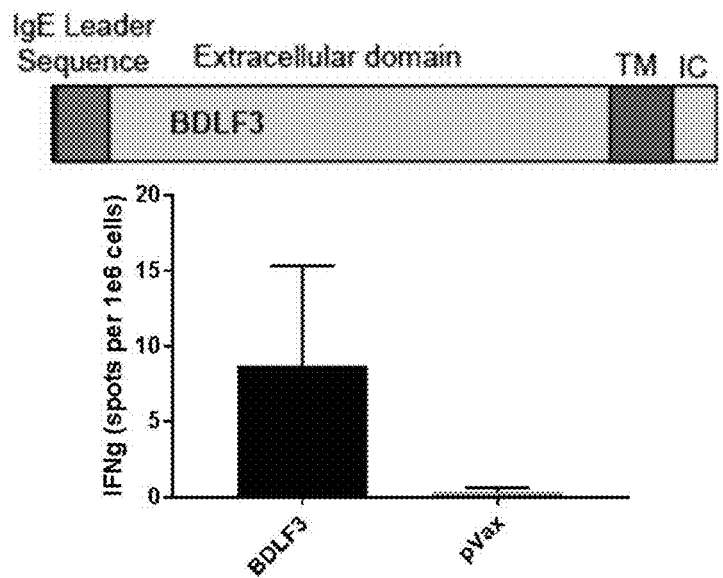
FIG. 13 depicts an exemplary ELISPOT assay demonstrating an IFNγ response following immunization with optimized BDLF3.
Figure 14:
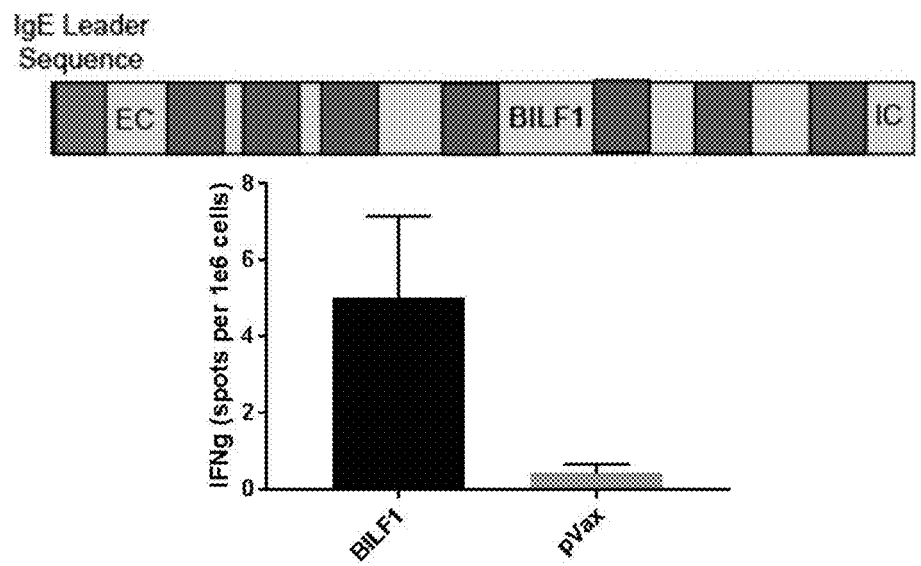
FIG. 14 depicts an exemplary ELISPOT assay demonstrating an IFNγ response following immunization with optimized BILF1.
Figure 15:
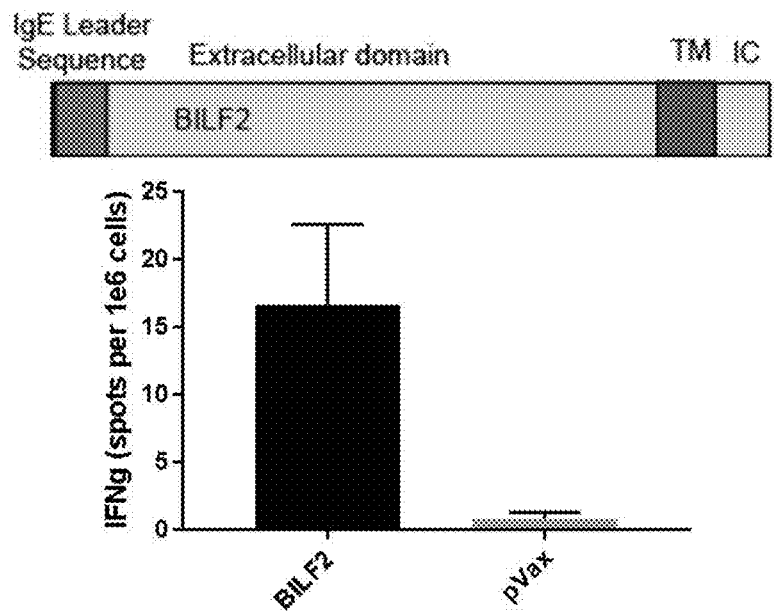
FIG. 15 depicts an exemplary ELISPOT assay demonstrating an IFNγ response following immunization with optimized BILF2.
Figure 16:
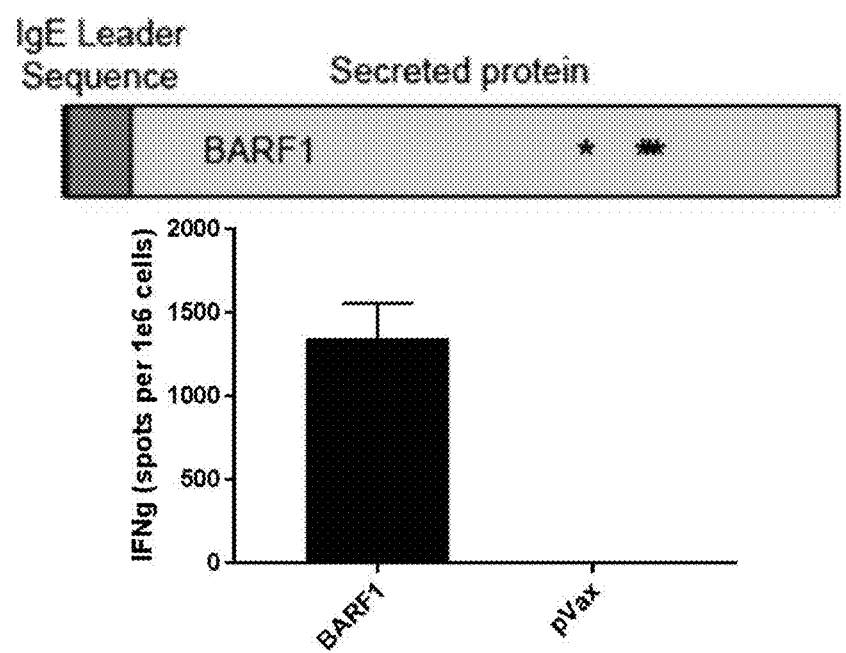
FIG. 16 depicts an exemplary ELISPOT assay demonstrating an IFNγ response following immunization with optimized BARF1.

Epstein-Barr virus (EBV) infection is associated with multiple diseases and disorders including multiple cancer types as well as autoimmune diseases.

In one embodiment, the invention includes a prophylactic nucleic acid vaccine against EBV infection. In one embodiment, the invention includes a therapeutic nucleic acid vaccine against one or more EBV-associated disease or disorder. In one embodiment, the vaccine comprise a plasmid encoding a consensus EBV antigen. In one embodiment, the consensus EBV antigen is a glycoprotein antigen. In one embodiment, the consensus EBV antigen is a latent-stage EBV antigen. In one embodiment, the consensus EBV antigens further comprise mutations that disrupt the oncogenic features of native antigens. As a vaccine candidate, an enhanced DNA (DNA)-based platform provides many advantages in genetic optimization and delivery techniques. As such, each EBV antigen can be genetically-optimized, subcloned into modified mammalian expression vectors, and then delivered using in vivo electroporation (EP).

Vaccination in preclinical rodent studies was highly potent, as vaccination with synthetic consensus EBV antigen constructs generates robust immune responses.

In some embodiments, the strategy employs a coding sequence for a synthetic consensus EBV antigen. Coding sequence for EBV glycoprotein antigens and latent-stage EBV antigens are provided. In some embodiments, the strategy employs coding sequences for a single synthetic consensus EBV antigen. In some embodiments, the strategy employs coding sequences for multiple synthetic consensus EBV antigens.

As a candidate for vaccines, DNA vaccines exhibit a multitude of advantages including rapid and inexpensive up-scale production, stability at room temperature, and ease of transport, all of which further enhance this platform from an economic and geographic perspective. Due to the synthetic nature of the plasmids, antigen sequences can be quickly and easily modified in response to newly emergent strains and/or expanded to include additional vaccine components.

Optimization of plasmid DNA vectors and their encoded antigen genes have led to increases in in vivo immunogenicity. Cellular uptake and subsequent antigen expression are substantially amplified when highly-concentrated plasmid vaccine formulations are administered with in vivo electroporation, a technology that uses brief square-wave electric pulses within the vaccination site to drive plasmids into transiently permeabilized cells. In theory, a cocktail of DNA plasmids could be assembled for directing a highly-specialized immune response against any number of variable antigens immunity can be further directed by co-delivery with plasmid molecular adjuvants encoding species-specific cytokine genes as well as 'consensus-engineering' of the antigen amino acid sequences to help bias vaccine-induced immunity towards particular strains.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein may mean any molecule added to a nucleic acid vaccines to enhance antigenicity of the vaccine.

"Antibody" may mean an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may mean refers to the nucleic acid (RNA or DNA molecule) that comprise a nucleotide sequence which encodes a protein. The coding sequence may further include initiation and termination signals operably linked to regulatory elements including a promoter and polyadenylation signal capable of directing expression in the cells of an individual or mammal to whom the nucleic acid is administered. The coding sequence may optionally further comprise a start codon that encodes an N terminal methionine or a signal peptide such as an IgE or IgG signal peptide.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Consensus" or "consensus sequence" as used herein may mean a synthetic nucleotide sequence, or corresponding polypeptide sequence, constructed based on analysis of an alignment of multiple sequences (e.g., multiple sequences of a particular virus antigen.)

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a percentage of a full length polypeptide sequence or nucleotide sequence. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the full length of the parental nucleotide sequence or amino acid sequence or variant thereof.

"Genetic construct" as used herein refers to the DNA or RNA molecules that comprise a nucleotide sequence which encodes a protein, such as an antibody. The genetic construct may also refer to a DNA molecule which transcribes an RNA. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more consensus antigen via the provided vaccines. The immune response can be in the form of a cellular or Immoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid molecule (e.g., probe) will hybridize to a second nucleic acid molecule (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance, Repressing the disease involves administering a vaccine of the present invention to a subject after clinical appearance of the disease.

"Variant" as used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference, Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleotide sequence that is substantially identical over the full length of the full gene sequence or a fragment thereof. The nucleotide sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid molecule containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Description

The invention provides an optimized consensus sequence encoding an EBV antigen. In one embodiment, the EBV antigen encoded by the optimized consensus sequence is capable of eliciting an immune response in a mammal. In one embodiment, the EBV antigen encoded by the optimized consensus sequence can comprise an epitope(s) that makes it particularly effective as an immunogen against which an immune response can be induced.

The optimized consensus sequence can be a consensus sequence derived from two or more EBV antigens. The optimized consensus sequence can comprise a consensus sequence and/or modification(s) for improved expression. Modification can include codon optimization, RNA optimization, addition of a kozak sequence for increased translation initiation, and/or the addition of an immunoglobulin leader sequence to increase immunogenicity. The EBV antigen encoded by the optimized consensus sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized consensus sequence can comprise a hemagglutinin (HA) tag. The antigen encoded by the optimized consensus sequence can be designed to elicit stronger cellular and/or humoral immune responses than a corresponding non-optimized antigen.

Provided herein are EBV antigens that can be used to induce immunity against EBV in genetically diverse subjects with EBV infection. In one embodiment, the present invention provides an immunogenic composition comprising one or more nucleic acid molecules that are capable of generating in a mammal an immune response against an EBV antigen. The present invention also provides isolated nucleic acid molecules that are capable of generating in a mammal an immune response against an EBV antigen. In one embodiment, the nucleic acid molecule comprises an optimized nucleotide sequence encoding a consensus EBV antigen.

In one embodiment, the EBV antigens are modified to reduce or disrupt at least one feature of a native EBV antigen. In various embodiments, the EBV antigens are modified to reduce or disrupt at least one of DNA replication, mitotic segregation, transcriptional activation, autoregulation, and suppression of the lytic cycle.

In one embodiment, the latent-stage EBV antigen of the invention is an EBNA1 antigen comprising at least one mutation of Δ41-52, Δ90-309, mutation of amino acid E444 or mutation of amino acid S446 relative to the native antigen sequence. In one embodiment, the EBNA1 antigen comprises at least one of Δ41-52, Δ90-309, a E444A mutation, and a S446A mutation.

In one embodiment, the latent-stage EBV antigen of the invention is a LMP1 antigen comprising at least one mutation of amino acid P204, Q206, T208 or Y369 relative to the native antigen sequence. In one embodiment, the LMP1 antigen of the invention is operably linked at the C terminus to a 30 amino acid peptide (LMP1TT30). In one embodiment, the LMP1 antigen comprises at least one of P204L, Q206L, T208A and Y369G.

In one embodiment, the latent-stage EBV antigen of the invention is a LMP2A antigen comprising at least one mutation of amino acid P57, P58, Y74, Y85, P98, P99 or Y112 relative to the native antigen sequence. In one embodiment, the LMP2A antigen comprises at least one of P57A, P58A, Y74F, Y85F, P98A, P99A and Y112F.

In one embodiment, the EBV glycoprotein antigen is gp350, gp42, gL, gH, gB, gM, gN, BDLF2, BDLF3, BILF1, BILF2, or BARF1. In one embodiment, the latent-stage EBV antigen is EBNA1, LMP1 or LMP2A. Table 1 provides a listing of exemplary sequences for EBV antigens for use in the compositions and methods of the invention.

TABLE 1

Synthetic Consensus sequences of EBV antigens

| SEQ ID NO: | Sequence Type | Antigen | Antigen Type |
|---|---|---|---|
| 1 | Nucleotide | gp350 | glycoprotein |
| 2 | Amino acid | gp350 | glycoprotein |
| 3 | Nucleotide | gp42 | glycoprotein |
| 4 | Amino acid | gp42 | glycoprotein |
| 5 | Nucleotide | gL | glycoprotein |
| 6 | Amino acid | gL | glycoprotein |
| 7 | Nucleotide | gH | glycoprotein |
| 8 | Amino acid | gH | glycoprotein |

TABLE 1-continued

Synthetic Consensus sequences of EBV antigens

| SEQ ID NO: | Sequence Type | Antigen | Antigen Type |
|---|---|---|---|
| 9 | Nucleotide | gB | glycoprotein |
| 10 | Amino acid | gB | glycoprotein |
| 11 | Nucleotide | gM | glycoprotein |
| 12 | Amino acid | gM | glycoprotein |
| 13 | Nucleotide | gN | glycoprotein |
| 14 | Amino acid | gN | glycoprotein |
| 15 | Nucleotide | BMRF2 | glycoprotein |
| 16 | Amino acid | BMRF2 | glycoprotein |
| 17 | Nucleotide | BDLF2 | glycoprotein |
| 18 | Amino acid | BDLF2 | glycoprotein |
| 19 | Nucleotide | BDLF3 | glycoprotein |
| 20 | Amino acid | BDLF3 | glycoprotein |
| 21 | Nucleotide | BILF2 | glycoprotein |
| 22 | Amino acid | BILF2 | glycoprotein |
| 23 | Nucleotide | BILF1 | glycoprotein |
| 24 | Amino acid | BILF1 | glycoprotein |
| 25 | Nucleotide | BARF1 | glycoprotein |
| 26 | Amino acid | BARF1 | glycoprotein |
| 27 | Nucleotide | EBNA1 | latent-stage |
| 28 | Amino acid | EBNA1 | latent-stage |
| 29 | Nucleotide | LMP2A | latent-stage |
| 30 | Amino acid | LMP2A | latent-stage |
| 31 | Nucleotide | LMP1TT30 | latent-stage |
| 32 | Amino acid | LMP1TT30 | latent-stage |

Consensus amino acid sequences for EBV glycoprotein antigens include SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and SEQ ID NO:26 and variants thereof, and fragments of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and SEQ ID NO:26, and variants thereof.

Consensus amino acid sequences for latent-stage EBV antigens include SEQ ID NO:28, SEQ ID NO:30, and SEQ ID NO:32, and variants thereof, and fragments of SEQ ID NO:28, SEQ ID NO:30, and SEQ ID NO:32, and variants thereof.

In one embodiment, the invention provides compositions comprising a nucleic acid molecule comprising a nucleotide sequence that encodes a synthetic consensus EBV antigen. In one embodiment, nucleotide sequences which encode synthetic consensus EBV glycoprotein antigens are provided as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, and SEQ ID NO:25, which encode SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and SEQ ID NO:26 respectively. In one embodiment, nucleotide sequences which encode synthetic consensus latent-stage EBV antigens are provided as SEQ ID NO:27, SEQ NO:29, and SEQ ID NO:31, which encode SEQ ID NO:28, SEQ ID NO:30, and SEQ ID NO:32 respectively.

In various embodiments, the invention provides compositions comprising a combination of one or more nucleic acid molecules encoding one or more synthetic consensus EBV antigen. The compositions may comprise a plurality of copies of a single nucleic acid molecule such a single plasmid, or a plurality of copies of two or more different nucleic acid molecules such as two or more different plasmids.

Compositions may comprise a single nucleic acid molecule, such as a plasmid, that contains coding sequence for multiple consensus EBV antigens. In one embodiment, the compositions may comprise a single nucleic acid molecule comprising nucleotide sequences that encode multiple EBV glycoprotein antigens. In one embodiment, the compositions may comprise a single nucleic acid molecule comprising nucleotide sequences that encode multiple latent-stage EBV antigens. In one embodiment, each coding sequence for each consensus EBV antigen is on a separate plasmid.

Accordingly, compositions that comprise one or more nucleotide sequence that encode multiple consensus EBV antigens may be on a single plasmid. In one embodiment, a composition comprises a single plasmid that encodes multiple synthetic consensus EBV antigens under a single promoter. In such an embodiment, the sequence that encodes a first synthetic consensus EBV antigen and the sequence that encodes a second synthetic consensus EBV antigen may be linked by a fusion peptide sequence, for example a furin cleavage sequence. Similarly, a sequence that encodes a second synthetic consensus EBV antigen and the sequence that encodes a third synthetic consensus EBV antigen may be linked by a fusion peptide sequence, for example a furin cleavage sequence In one embodiment, an optimized consensus encoded EBV antigen is operably linked to one or more regulatory elements. In one embodiment, a regulatory element is a leader sequence. In one embodiment, the leader sequence is an IgE leader sequence. In one embodiment, the IgE leader sequence has an amino acid sequence as set forth in SEQ ID NO:33. Therefore in one embodiment, the invention relates to an amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32 operably linked to an amino acid sequence as set forth in SEQ ID NO:33. In one embodiment, the invention relates to a nucleotide sequence encoding an amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32 operably linked to an amino acid sequence as set forth in SEQ ID NO:33.

In one embodiment, the gp350 antigen of the invention comprises SEQ ID NO:2 operably linked to a native gp350 leader sequence MEAALLVCQYTIQSLIHLTG (SEQ ID NO:34). In one embodiment, the gp350 antigen of the invention comprises SEQ ID NO:2 operably linked to the IgE leader sequence: MDWTWILFLVAAATRVHS (SEQ ID NO:33).

In one embodiment, the gp42 antigen of the invention comprises SEQ ID NO:4 operably linked to a native gp42 leader sequence MVSFKQVRVPLFTAIALVIVLLLAYFLPPRVRG (SEQ ID NO:35). In one embodiment, the gp42 antigen of the invention comprises SEQ ID NO:4 operably linked to the IgE leader sequence: MDWTWILFLVAAATRVHS (SEQ ID NO:33).

In one embodiment, the gL antigen of the invention comprises SEQ ID NO:6 operably linked to a native gL leader sequence MRAVGVFLATCLVTIFVLPTWG (SEQ ID NO:36). In one embodiment, the gL antigen of the invention comprises SEQ ID NO:6 operably linked to the IgE leader sequence: MDWTWILFLVAAATRVHS (SEQ ID NO:33).

In one embodiment, the gH antigen of the invention comprises SEQ ID NO:8 operably linked to a native gH leader sequence MQLLCVFCLVLLWEVGAA (SEQ ID NO:37). In one embodiment, the gH antigen of the invention comprises SEQ ID NO:8 operably linked to the IgE leader sequence: MDWTWILFLVAAATRVHS (SEQ ID NO:33).

In one embodiment, the gB antigen of the invention comprises SEQ ID NO:10 operably linked to a native gB leader sequence MTRRRVLSVVVLLAALACRLGA (SEQ ID NO:38). In one embodiment, the gB antigen of the invention comprises SEQ ID NO:10 operably linked to the IgE leader sequence: MDWTWILFLVAAATRVHS (SEQ ID NO:33).

In one embodiment, the gN antigen of the invention comprises SEQ ID NO:14 operably linked to a native gN leader sequence MGKVLRKPFAKAVPLLF-LAATWLLTGVLPAGA (SEQ ID NO:39). In one embodiment, the gN antigen of the invention comprises SEQ ID NO:14 operably linked to the IgE leader sequence: MDWTWILFLVAAATRVHS (SEQ ID NO:33).

In one embodiment, the BDLF3 antigen of the invention comprises SEQ ID NO:20 operably linked to a native BDLF3 leader sequence MAHARDKAGAVLAMILICET-SLIWTSSG (SEQ ID NO:40). In one embodiment, the BDLF3 antigen of the invention comprises SEQ ID NO:20 operably linked to the IgE leader sequence: MDWTWILFLVAAATRVHS (SEQ ID NO:33).

In one embodiment, the BILF2 antigen of the invention comprises SEQ ID NO:22 operably linked to a native BILF2 leader sequence MTHLVLLLCCCVGSVCA (SEQ ID NO:41). In one embodiment, the BILF2 antigen of the invention comprises SEQ ID NO:22 operably linked to the IgE leader sequence: MDWTWILFLVAAATRVHS (SEQ ID NO:33).

In one embodiment, the BILF1 antigen of the invention comprises SEQ ID NO:24 operably linked to a native BILF1 leader sequence MLSTMAPGSTVGTLVANMTSVNA (SEQ ID NO:42). In one embodiment, the BILF1 antigen of the invention comprises SEQ ID NO:24 operably linked to the IgE leader sequence: MDWTWILFLVAAATRVHS (SEQ ID NO:33).

In one embodiment, the BARF1 antigen of the invention comprises SEQ ID NO:26 operably linked to a native BARF1 leader sequence MARFIAQLLLLASCVAAGQA (SEQ ID NO:43). In one embodiment, the BARF1 antigen of the invention comprises SEQ ID NO:26 operably linked to the IgE leader sequence: MDWTWILFLVAAATRVHS (SEQ ID NO:33).

In one embodiment, a regulatory element is a start codon. Therefore, in one embodiment, the invention relates to a nucleotide sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 or a fragment or homolog thereof, operably linked to a nucleotide sequence comprising a start codon at the 5' terminus. In one embodiment, the invention relates to an amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32 or a fragment or homolog thereof, operably linked to an amino acid encoded by a start codon (e.g., a Methionine) at the N-terminus.

In one embodiment, a regulatory element is at least one stop codon. Therefore, in one embodiment, the invention relates to a nucleotide sequence as set forth in SEQ NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID SEQ ID NO:21, SEQ ID NO:23, SEQ ID NO:25, SEQ ID NO:27, SEQ ID NO:29, or SEQ ID NO:31, or a fragment or homolog thereof, operably linked to a nucleotide sequence comprising at least one stop codon at the 3' terminus. In one embodiment, the nucleotide sequence is operably linked to two stop codons to increase the efficiency of translational termination.

In one embodiment, nucleic acid molecule can encode at least one peptide having the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. In one embodiment, the nucleic acid molecule comprises at least one nucleotide sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. In some embodiments, the sequence can be the nucleotide sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleotide sequence set forth in SEQ ID NO:1, SEQ ID NO:3, SEQ ID NO:5, SEQ ID NO:7, SEQ ID NO:9, SEQ ID NO: 11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. In other embodiments, sequence can be the nucleotide sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32.

In some embodiments, the nucleic acid molecule comprises an RNA sequence that is a transcript from a DNA sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleotide sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. In some embodiments, the nucleic acid molecule comprises an RNA sequence that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32.

In some embodiments, the nucleic acid molecule may comprise a nucleotide sequence that encodes a full length consensus EBV antigen. The nucleic acid molecules may comprise a sequence that encodes SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. The nucleic acid molecules may comprise a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. The nucleic acid molecule may optionally comprise coding sequences that encode a signal peptide such as for example an IgE or IgG signal peptide.

The consensus-EBV antigen can be a peptide having the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32.

In some embodiments, the antigen can have an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32.

Immunogenic fragments of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of the full length of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. In some embodiments, immunogenic fragments include a leader sequence, such as for example an immunoglobulin leader, such as the IgE leader. In some embodiments, immunogenic fragments are free of a leader sequence.

Immunogenic fragments of proteins with amino acid sequences homologous to immunogenic fragments of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32, can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

In one embodiment, an immunogenic fragment of a nucleic acid molecule encodes at least one immunodominant or sub-immunodominant epitope of a full length optimized consensus EBV antigen.

Some embodiments relate to immunogenic fragments of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 comprising at least 60%, at least 65%, at least 70%, at least 75%, at least 80%, at least 85%, at least 90%, at least 95%, at least 96%, at least 97%, at least 98% or at least 99% of the full length of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. Immunogenic fragments can be at least 96%, at least 97% at least 98% or at least 99% homologous to fragments of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. In some embodiments, immunogenic fragments include sequences that encode a leader sequence, such as for example an immunoglobulin leader, such as the IgE leader. In some embodiments, fragments are free of coding sequences that encode a leader sequence.

In one embodiment, the nucleic acid molecule comprises a sequence at least 90% homologous to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31.

In one embodiment, the nucleic acid molecule comprises an RNA sequence encoding a consensus EBV antigen sequence described herein. For example, nucleic acids may comprise an RNA sequence encoding one or more of SEQ ID NO:2, SEQ NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32, a variant thereof, a fragment thereof or any combination thereof.

In some embodiments, the nucleic acid molecule includes a sequence that encodes for an EBV antigen minus an IgE leader sequence on the N-terminal end of the coding sequence. In some embodiments, the DNA nucleic acid molecule further comprises an IgE leader sequence attached to an N-terminal end of the coding sequence and operably linked to the promoter.

The nucleic acid molecule can further include a polyadenylation sequence attached to the C-terminal end of the coding sequence. In one embodiment, the nucleic acid molecule is codon optimized.

Vaccines and Immunogenic Compositions

Immunogenic compositions, such as vaccines, are provided comprising an optimized consensus sequence, an optimized consensus-encoded antigen, a fragment thereof, a variant thereof, or a combination thereof. The immunogenic composition can significantly induce an immune response of a subject administered with the immunogenic composition against the EBV antigen. The vaccine may comprise a plurality of the nucleic acid molecules, or combinations thereof. The vaccine may be provided to induce a therapeutic or prophylactic immune response.

The immunogenic composition can be a DNA vaccine, an RNA vaccine, a peptide vaccine, or a combination vaccine. The vaccine can include an optimized consensus nucleotide sequence encoding an antigen. The nucleotide sequence can be DNA, RNA, cDNA, a variant thereof, a fragment thereof, or a combination thereof. The nucleotide sequence can also include additional sequences that encode linker, leader, or tag sequences that are linked to the antigen by a peptide bond. The peptide vaccine can include an antigen, a variant thereof, a fragment thereof, or a combination thereof. The combination DNA and peptide vaccine can include the above described optimized consensus nucleotide sequence and the encoded antigen.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can be an RNA of the one or more EBV antigens. The RNA vaccine can be introduced into the cell.

The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine of the present invention can have features required of effective vaccines such as being safe so that the vaccine itself does not cause illness or death; being protective against illness; inducing protective cell responses; and providing ease of administration, few side effects, biological stability, and low cost per dose.

Provided herein is an immunogenic composition capable of generating in a mammal an immune response against EBV. The immunogenic composition may comprise each plasmid as discussed above. The immunogenic composition may comprise a plurality of the plasmids, or combinations thereof. The immunogenic composition may be provided to induce a therapeutic or prophylactic immune response.

Immunogenic compositions may be used to deliver nucleic acid molecules that encode one or more consensus EBV antigen. Immunogenic compositions are preferably compositions comprising plasmids.

The immunogenic composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the immunogenic composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the immunogenic compositions may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the immunogenic composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be one or more adjuvants. An adjuvant may be other genes that are expressed from the same or from an alternative plasmid or are delivered as proteins in combination with the plasmid above in the immunogenic composition. The one or more adjuvants may be proteins and/or nucleic acid molecules that encode proteins selected from the group consisting of: CCL20, α-interferon (IFN-α), β-interferon (IFN-β), γ-interferon, platelet derived growth factor (PDGF), TNFα, TNFβ, GM-CSF, epidermal growth factor (EGF), cutaneous cell-attracting chemokine (CTACK), epithelial thymus-expressed chemokine (TECK), mucosae-associated epithelial chemokine (MEC), IL-12, IL-15 including IL-15 having the signal sequence or coding sequence that encodes the signal sequence deleted and optionally including a different signal peptide such as that from IgE or coding sequence that encodes a difference signal peptide such as that from IgE, IL-28, MHC, CD80, CD86, IL-1, IL-2, IL-4, IL-5, IL-6, IL-10, IL-18, MCP-1, MIP-1α, MIP-1β, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof. or a combination thereof.

In some embodiments, the adjuvant may be one or more proteins and/or nucleic acid molecules that encode proteins selected from the group consisting of: CCL-20, IL-12, IL-15, IL-28, CTACK, TECK, MEC or RANTES. Examples of IL-12 constricts and sequences are disclosed in PCT application no. PCT/US1997/019502 and corresponding U.S. application Ser. No. 08/956,865, and U.S. Provisional Application Ser. No. 61/569,600 filed Dec. 12, 2011, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/US10/048827, which are each incorporated herein by reference. Examples of IL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

The immunogenic composition may further comprise a genetic vaccine facilitator agent as described in U.S. Ser. No. 021,579 filed Apr. 1, 1994, which is fully incorporated by reference.

The immunogenic composition may comprise the consensus antigens and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the consensus antigen or plasmid thereof.

In some embodiments, pharmaceutical compositions according to the present invention comprise at least 10, 15, 20, 25, 30, 35, 40, 45, 50, 55, 60, 65, 70, 75, 80, 85, 90, 95 or 100 nanograms of a nucleic acid molecule of the invention. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms of a nucleic acid molecule of the invention. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of a nucleic acid molecule of the invention.

In other embodiments, the pharmaceutical composition can comprise up to and including 15, 20, 25, 30, 35, 40, 45, 50, 55, 60, 65, 70, 75, 80, 85, 90, 95 or 100 nanograms of a nucleic acid molecule of the invention. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms of a nucleic acid molecule of the invention. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of a nucleic acid molecule of the invention.

The immunogenic composition may be formulated according to the mode of administration to be used. An injectable immunogenic composition pharmaceutical composition may be sterile, pyrogen free and particulate free. An isotonic formulation or solution may be used. Additives for isotonicity may include sodium chloride, dextrose, mannitol, sorbitol, and lactose. The immunogenic composition may comprise a vasoconstriction agent. The isotonic solutions may include phosphate buffered saline. Immunogenic composition may further comprise stabilizers including gelatin and albumin. The stabilizing may allow the formulation to be stable at room or ambient temperature for extended periods of time such as LGS or polycations or polyanions to the immunogenic composition formulation.

The immunogenic composition may be stable at room temperature (25° C.) for more than 1 week, in some embodiments for more than 2 weeks, in some embodiments for more than 3 weeks, in some embodiments for more than 4 weeks, in some embodiments for more than 5 weeks, and in some embodiments for more than 6 weeks. In some embodiments, the vaccine is stable for more than one month, more than 2 months, more than 3 months, more than 4 months, more than 5 months, more than 6 months, more than 7 months, more than 8 months, more than 9 months, more than 10 months, more than 11 months, or more than 12 months. In some embodiments, the vaccine is stable for more than 1 year, more than 2 years, more than years, or more than 5 years. In one embodiment, the immunogenic composition is stable under refrigeration (2-8° C.). Accordingly, in one embodiment, the immunogenic composition does not require frozen cold-chain. An immunogenic composition is stable if it retains its biological activity for a sufficient period to allow its intended use (e.g., to generate an immune response in a subject). For example, for immunogenic compositions that are to be stored, shipped, etc., it may be desired that the immunogenic compositions remain stable for months to years.

Vector

The nucleotide construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid construct may be chimeric, meaning that at least one of its components is heterologous with respect to at least one of its other components.

(2) Plasmid

The one or more vectors can be a plasmid. The plasmid may be useful for transfecting cells with the recombinant nucleic acid construct. The plasmid may be useful for introducing the recombinant nucleic acid construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

(3) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to one of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO: 31, or a variant thereof or a fragment thereof. In another embodiment, the nucleotide sequence comprises an RNA sequence transcribed by a DNA sequence encoding a polypeptide sequence at least 90% homologous to one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32 or a variant thereof or a fragment thereof. Accordingly, in one embodiment, the invention provides an RNA molecule encoding one or more of the EBV antigens. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

(4) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid construct. The LEC may be any linear DNA devoid of any phosphate backbone. The LEC may not contain any antibiotic resistance genes and/or a phosphate backbone. The LEC may not contain other nucleotide sequences unrelated to the desired gene expression.

The LEC may be derived from any plasmid capable of being linearized. The plasmid may be capable of expressing the heavy chain polypeptide and/or light chain polypeptide encoded by the recombinant nucleic acid construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid construct.

The LEC can be pcrM2. The LEC can be pcrNP. pcrNP and pcrMR can be derived from pNP (Puerto Rico/34) and pM2 (New Caledonia/99), respectively.

(5) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al, (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585, 362.

(6) Method of Preparing the Vector

Provided herein is a method for preparing the one or more vectors in which the recombinant nucleic acid construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939, 792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

Multiple Vectors

The immunogenic composition may comprise a plurality of copies of a single nucleic acid molecule such a single plasmid, or a plurality of copies of two or more different nucleic acid molecules such as two or more different plasmids. For example an immunogenic composition may comprise plurality of two, three, four, five, six, seven, eight, nine or ten or more different nucleic acid molecules. Such compositions may comprise plurality of two, three, four, five, six, or more different plasmids.

Immunogenic compositions may comprise nucleic acid molecules, such as plasmids, that collectively contain coding sequence for an EBV antigen immunogenic compositions may comprise nucleic acid molecules, such as plasmids, that collectively contain coding sequence for multiple antigens. In one embodiment, the antigens are an EBV antigen and one or more additional cancer antigen. Immunogenic compositions may comprise nucleic acid molecules, such as plasmids, that collectively contain coding sequence for one or more EBV antigen and one or more cancer antigen.

Cancer Antigens

The immunogenic composition can comprise one or more cancer antigens such as WT1, MUC1, LMP2, HPV E6 E7, EGFRvIII, HER-2/neu, Idiotype, MAGE A3, p53 (non-mutant), NY-ESO-1, PSMA, GD2, CEA, MelanA/MART1, Ras-mutant, gp100, p53 mutant, Proteinase 3 (PR1), Bcr-abl, Tyrosinase, Survivin, PSA, hTERT, EphA2, PAP, ML-IAP, AFP, EpCAM, ERG, NA17, PAX3, ALK, Androgen Receptor, Cyclin B1, Polysialic Acid, MYCN, TRP-2, RhoC, GD3, Fucosyl GM1, Mesothelin, PSCA, MAGE A1, sLe(a), CYP1B1, PLAC1, GM3 ganglioside, BORIS, Tn, GloboH, ETV6-AML, NY-BR-1, RGS5, SART3, STn, Carbonic anhydrase IX, PAX5, OY-TES1, Sperm Protein 17, LCK, HMWMAA, Sperm fibrous sheath proteins, AKAP-4, SSX2, XAGE 1, B7H3, Legumain, Tie 2, Page 4, VEGFR2, MAD-CT-1 (protamine 2), MAD-CT-2, and FOS-related antigen 1 to treat or prevent a tumor associated pathology. The immunogenic composition can further combine one or more cancer antigens WT1, MUC1, LMP2, HPV E6 E7, EGFRvIII, HER-2/neu, Idiotype, MAGE A3, p53 (non-mutant), NY-ESO-1, PSMA, GD2, CEA, MelanA/MART1, Ras-mutant, gp100, p53 mutant, Proteinase 3 (PR1), Bcr-abl, Tyrosinase, Survivin, PSA, hTERT, EphA2, PAP, ME-IAP, AFP, EpCAM, ERG, NA17, PAX3, ALK, Androgen Receptor, Cyclin B1, Polysialic Acid, MYCN, TRP-2, RhoC, GD3, Fucosyl GM1, Mesothelin, PSCA, MAGE A1, sLe(a), CYP1B1, PLAC1, GM3 ganglioside, BORIS, Tn, GloboH, ETV6-AML, NY-BR-1, RGS5, SART3, STn, Carbonic anhydrase IX, PAX5, OY-TES1, Sperm Protein 17, LCK, HMWMAA, Sperm fibrous sheath proteins, AKAP-4, SSX2, XAGE 1, B7H3, Legumain, Tie 2, Page 4, VEGFR2, MAD-CT-1 (protamine 2), MAD-CT-2, and FOS-related antigen with an optimized consensus encoded EBV antigen for treating or preventing a tumor associated pathology. Other combinations of cancer antigens may also be applied for treating or preventing a tumor associated pathology.

Methods

Provided herein are methods of treating, protecting against, and/or preventing an EBV associated disease in a subject in need thereof by administering one or more immunogenic composition described herein to the subject. Administration of the immunogenic composition to the subject can induce or elicit an immune response in the subject. The induced immune response can be used to treat, prevent, and/or protect against disease, for example, EBV infection or a disease or disorder associated with EBV latency.

Provided herein is a method for delivering the immunogenic composition for providing genetic constructs and proteins of the consensus antigen which comprise epitopes that make them particular effective against EBV or a disease or disorder associated with EBV latency, against which an immune response can be induced. The method of delivering the immunogenic composition or vaccination may be provided to induce a therapeutic and prophylactic immune response. The vaccination process may generate in the mammal an immune response against EBV or a disease or disorder associated with EBV latency. The immunogenic composition may be delivered to an individual to modulate the activity of the mammal's immune system and enhance the immune response. The delivery of the immunogenic composition may be the transfection of the consensus antigen as a nucleic acid molecule that is expressed in the cell and delivered to the surface of the cell upon which the immune system recognized and induces a cellular, humoral, or cellular and humoral response. The delivery of the immunogenic composition may be used to induce or elicit and immune response in mammals against EBV or a disease or disorder associated with EBV latency by administering to the mammals the immunogenic composition as discussed above.

Upon delivery of the immunogenic composition and plasmid into the cells of the mammal, the transfected cells will express and secrete consensus antigens for each of the plasmids injected from the immunogenic composition. These proteins will be recognized as foreign by the immune system and antibodies will be made against them. These antibodies will be maintained by the immune system and allow for an effective response to subsequent infections by EBV.

The immunogenic composition may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

The induced immune response can include an induced humoral immune response and/or an induced cellular immune response. The humoral immune response can be induced by about 1.5-fold to about 16-fold, about 2-fold to about 12-fold, or about 3-fold to about 10-fold. The induced cellular immune response can include a CD8$^+$ cell response, which is induced by about 2-fold to about 30-fold, about 3-fold to about 25-fold, or about 4-fold to about 20-fold.

Immune Response

The immunogenic composition can induce an immune response in the subject administered the composition. The induced immune response can be specific for an EBV antigen. The induced immune response can be reactive with an EBV antigen related to the optimized consensus-encoded antigen. In various embodiments, related antigens include antigens having amino acid sequences having at least 90%, at least 91%, at least 92%, at least 93%, at least 94%, at least 95%, at least 96%, at least 97%, at least 98%, at least 99%, or 100% homology to the amino acid sequence of the optimized consensus-encoded antigen. In various embodiments, related antigens include antigens encoded by nucleotide sequences having at least 90%, at least 91%, at least 92%, at least 93%, at least 94%, at least 95%, at least 96%, at least 97%, at least 98%, at least 99%, or 100% homology to the optimized consensus nucleotide sequences disclosed herein.

The immunogenic composition can induce a humoral immune response in the subject administered the immunogenic composition. The induced humoral immune response can be specific for an EBV antigen. The induced humoral immune response can be reactive with the EBV antigen related to the optimized consensus-encoded antigen. The humoral immune response can be induced in the subject administered the immunogenic composition by about 1.5-fold to about 16-fold, about 2-fold to about 12-fold, or about 3-fold to about 10-fold. The humoral immune response can be induced in the subject administered the immunogenic composition by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized EBV antigen.

The humoral immune response induced by the immunogenic composition can include an increased level of IgG antibodies associated with the subject administered the immunogenic composition as compared to a subject not administered the immunogenic composition. These IgG antibodies can be specific for the EBV antigen genetically related to the optimized consensus antigen. These IgG antibodies can be reactive with the EBV antigen genetically related to the optimized consensus antigen. The level of IgG antibody associated with the subject administered the immunogenic composition can be increased by about 1.5-fold to about 16-fold, about 2-fold to about 12-fold, or about 3-fold to about 10-fold as compared to the subject not administered the immunogenic composition. The level of IgG antibody associated with the subject administered the immunogenic composition can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized EBV antigen.

The immunogenic composition can induce a cellular immune response in the subject administered the immunogenic composition. The induced cellular immune response can be specific for an EBV antigen related to the optimized consensus-encoded antigen. The induced cellular immune response can be reactive to the EBV antigen related to the optimized consensus-encoded antigen. The induced cellular immune response can include eliciting a CD8$^+$ cell response. The elicited CD8$^+$ cell response can be reactive with the EBV antigen genetically related to the optimized consensus antigen. The elicited CD8$^+$ cell response can be polyfunctional. The induced cellular immune response can include eliciting a CD8+ cell response, in which the CD8+ cells produce interferon-gamma (IFN-γ), tumor necrosis factor alpha (TNF-α), interleukin-2 (IL-2), or a combination of IFN-γ and TNF-α.

The induced cellular immune response can include an increased CD8+ cell response associated with the subject administered the immunogenic composition as compared to the subject not administered the immunogenic composition. The CD8+ cell response associated with the subject administered the immunogenic composition can be increased by about 2-fold to about 30-fold, about 3-fold to about 25-fold, or about 4-fold to about 20-fold as compared to the subject not administered the immunogenic composition. The CD8+ cell response associated with the subject administered the immunogenic composition can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic composition or a subject administered a non-optimized EBV antigen.

The induced cellular immune response can include an increased frequency of CD107a/IFNγ/T-bet triple-positive CD8 cells that are reactive against the EBV antigen. The frequency of CD107a/IFNγ/T-bet triple-positive CD8 cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized EBV antigen.

The induced cellular immune response can include an increased frequency of CD107a/IFNγ double-positive CD8 cells that are reactive against the EBV antigen. The frequency of CD107a/IFNγ double-positive CD8 cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic composition or a subject administered a non-optimized EBV antigen.

The cellular immune response induced by the immunogenic composition can include eliciting a CD4+ cell response. The elicited CD4+ cell response can be reactive with the EBV antigen genetically related to the optimized consensus antigen. The elicited CD4+ cell response can be polyfunctional. The induced cellular immune response can include eliciting a CD4+ cell response, in which the CD4+ cells produce IFN-γ, TNF-α, IL-2, or a combination of IFN-γ and TNF-α.

The induced cellular immune response can include an increased frequency of CD4+ cells that produce IFN-γ. The frequency of CD4+IFN-γ+ cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized EBV antigen.

The induced cellular immune response can include an increased frequency of CD4+ cells that produce TNF-α. The frequency of CD4+TNF-α+ cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic composition or a subject administered a non-optimized EBV antigen.

The induced cellular immune response can include an increased frequency of CD4+ cells that produce both IFN-γ and TNF-α. The frequency of CD4+IFN-γ+TNF-α+ associated with the subject administered the immunogenic composition can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic composition or a subject administered a non-optimized EBV antigen.

The immunogenic composition can further induce an immune response when administered to different tissues such as the muscle or skin. The immunogenic composition can further induce an immune response when administered via electroporation, or injection, or subcutaneously, or intramuscularly.

Dosage and Formulation

The immunogenic composition dose can be between 1 μg to 10 mg active component/kg body weight/time, and can be 20 μg to 10 mg component/kg body weight/time. The immunogenic composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of immunogenic composition doses for effective treatment can be 1, 2, 3, 4, 5, 6, 7, 8, 9, or 10.

The immunogenic composition can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration.

The immunogenic composition can be administered prophylactically or therapeutically. In prophylactic administration, the immunogenic compositions can be administered in an amount sufficient to induce an immune response. In therapeutic applications, the immunogenic compositions are administered to a subject in need thereof in an amount sufficient to elicit a therapeutic effect. An amount adequate to accomplish this is defined as "therapeutically effective dose." Amounts effective for this use will depend on, e.g., the particular composition of the immunogenic composition regimen administered, the manner of administration, the stage and severity of the disease, the general state of health of the subject, and the judgment of the prescribing physician.

The immunogenic composition can be administered by methods well known in the art as described in Donnelly et al. (Ann. Rev. Immunol. 15:617-648 (1997)); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the immunogenic composition can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The immunogenic composition can be delivered via a variety of routes. Typical delivery routes include parenteral administration, e.g., intradermal, intramuscular or subcutaneous delivery. Other routes include oral administration, intranasal, and intravaginal routes. For the DNA of the immunogenic composition in particular, the immunogenic composition can be delivered to the interstitial spaces of tissues of an individual (Feigner et al., U.S. Pat. Nos. 5,580,859 and 5,703,055, the contents of all of which are incorporated herein by reference in their entirety). The immunogenic composition can also be administered to muscle, or can be administered via intradermal or subcutaneous injections, or transdermally, such as by iontophoresis. Epidermal administration of the immunogenic composition can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The immunogenic composition can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the immunogenic composition.

The immunogenic composition can be a liquid preparation such as a suspension, syrup or elixir. The immunogenic composition can also be a preparation for parenteral, subcutaneous, intradermal, intramuscular or intravenous administration (e.g., injectable administration), such as a sterile suspension or emulsion.

The immunogenic composition can be incorporated into liposomes, microspheres or other polymer matrices (Feigner et al., U.S. Pat. No. 5,703,055; Gregoriadis, Liposome Technology, Vols. Ito III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

Infectious Disease

Epstein-Barr can cause infectious mononucleosis, also known as 'glandular fever', 'mono' and 'Pfeiffer's disease'. The vaccine can be used to generate or elicit an immune response in a mammal that is reactive or directed to a cell expressing a latent-stage EBV antigen in a subject. The elicited immune response can treat or prevent infectious mononucleosis disease in the subject administered the vaccine.

Autoimmune Disease

The vaccine can be used to generate or elicit an immune response in a mammal that is reactive or directed to a cell expressing a latent-stage EBV antigen in a subject. The elicited immune response can treat or prevent an autoimmune disease or disorder in the subject. In one embodiment, an autoimmune disease or disorder is at least one of Addison's disease, Agammaglobulinemia, Alopecia areata, Amyloidosis, Ankylosing spondylitis, Anti-GBM/Anti-TBM nephritis, Antiphospholipid syndrome (APS), Asthma, Autoimmune inner ear disease (AIED), Axonal & neuronal neuropathy (AMAN), Behcet's disease, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss, Cicatricial pemphigoid/benign mucosal pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Food allergies, Gastroenteritis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammalglobulinemia, IgA Nephropathy, IgG4-related sclerosing disease, Inclusion body myositis (IBM), Inflammatory bowel disease, Interstitial cystitis (IC), Juvenile arthritis, Juvenile rheumatoid arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multiple sclerosis (MS), Myasthenia gravis, Myositis, Narcolepsy, Neuromyelitis optica, Neutropenia, Ocular cicatricial pemphigoid, Optic neuritis, Palindromic rheumatism (PR), PANDAS (Pediatric Autoimmune. Neuropsychiatric Disorders Associated, with, Streptococcus), Paraneoplastic cerebellar degeneration (PCD), Parkinson's disease, Paroxysmal nocturnal hemoglobinuria (PM), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome (polyneuropathy, organomegaly, endocrinopathy, monoclonal, gammopathy, skin changes), Polyarteritis nodosa, Polymyalgia rheumatica, Polymyositis, Postmyocardial infarction syndrome, Postpericardiotomy syndrome, Progesterone dermatitis, Psoriasis, Pure red cell aplasia (PRCA), Pyoderma gangrenosum, Raynaud's phenomenon, Reactive Arthritis, Reflex sympathetic dystrophy, Reiter's syndrome, Relapsing polychondritis, Restless legs syndrome (RLS), Retroperitoneal fibrosis, Rheumatic fever, Rheumatoid arthritis (RA), Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis. Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Wegener's granulomatosis (Granulomatosis with Polyangiitis (GPA)).

Cancer

The vaccine can be used to generate or elicit an immune response in a mammal that is reactive or directed to a cancer or tumor (e.g., a cancer or tumor associated with EBV latency) of the mammal or subject in need thereof. The elicited immune response can treat or prevent cancer or tumor growth.

The elicited immune response can prevent and/or reduce metastasis of cancerous or tumor cells. Accordingly, the vaccine can be used in a method that treats and/or prevents cancer or tumors in the mammal or subject administered the vaccine.

The following are non-limiting examples of cancers that can be treated or prevented by the disclosed methods and compositions: acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, burkitt lymphoma, carcinoid tumor, central nervous system atypical teratoid/rhabdoid tumor, central nervous system embryonal tumors, central nervous system lymphoma, cerebellar astrocytoma, cerebral astrocytoma/malignant glioma, cerebral astrocytotna/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromal tumor (gist), germ cell tumor, gestational cancer, gestational trophoblastic tumor, glioblastoma, glioma, hairy cell leukemia, head and neck cancer, hepatocellular (liver) cancer, histiocytosis, hodgkin lymphoma, non-hodgkin lymphoma hypopharyngeal cancer, hypothalamic and visual pathway glioma, hypothalamic tumor, intraocular (eye) cancer, intraocular melanoma, islet cell tumors, kaposi sarcoma, kidney (renal cell) cancer, langerhans cell cancer, langerhans cell histiocytosis, laryngeal cancer, leukemia, lip and oral cavity cancer, liver cancer, lung cancer, lymphoma, macroglobulinemia, malignant fibrous histiocytoma of bone and osteosarcoma, medulloblastoma, medulloepithelioma, melanoma, merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, sezary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer stomach (gastric) cancer, supratentorial primitive neuroectodermal tumors, supratentorial primitive neuroectodennal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, waldenstrom macroglobulinemia, and wilms tumor.

The vaccine can be used to generate or elicit an immune response in a mammal that is reactive or directed to a lymphoma, including, but not limited to, Burkitt's lymphoma, Hodgkin lymphoma, non-Hodgkin lymphoma, Post-transplant lymphoma, T-cell lymphoma, Natural killer (NK) lymphoma and AIDS-associated B-cell lymphoma, in the mammal or subject in need thereof. The elicited immune response can prevent lymphoma proliferation. The elicited immune response can reduce lymphoma proliferation. Accordingly, the vaccine can be used in a method that treats and/or prevents lymphoma in the mammal or subject administered the vaccine.

The vaccine can be used to generate or elicit an immune response in a mammal that is reactive or directed to a carcinoma, including, but not limited to, gastric carcinoma and nasopharyngeal carcinoma, in the mammal or subject in need thereof. The elicited immune response can prevent carcinoma growth. The elicited immune response can reduce carcinoma growth. The elicited immune response can prevent or reduce carcinoma metastasis. Accordingly, the vaccine can be used in a method that treats and/or prevents carcinoma in the mammal or subject administered the vaccine.

In some embodiments, the administered vaccine can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic lymphocyte such as CD8+ (CTL) to attack and kill tumor cells; (3) increase helper cell responses; (4) and increase inflammatory responses via IFN-γ and TFN-α or preferably all of the aforementioned.

In some embodiments, the immune response can generate a humoral immune response and/or an antigen-specific cytotoxic lymphocyte (CTL) response that does not cause damage to or inflammation of various tissues or systems brain or neurological system, etc.) in the subject administered the vaccine.

In some embodiments, the administered vaccine can increase tumor free survival, reduce tumor mass, increase tumor survival, or a combination thereof in the subject. The administered vaccine can increase tumor free survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% or more in the subject. The administered vaccine can reduce tumor mass by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% or more in the subject after immunization. The administered vaccine can prevent and block increases in monocyte chemoattractant protein 1 (MCP-1), a cytokine secreted by myeloid derived suppressor cells, in the subject. In some embodiments, the administered vaccine can prevent and block increases in MCP-1 within the cancerous or tumor tissue in the subject, thereby reducing vascularization of the cancerous or tumor tissue in the subject.

The administered vaccine can increase tumor survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% or more in the subject. In some embodiments, the vaccine can be administered to the periphery (as described in more detail below) to establish an antigen-specific immune response targeting the cancerous or tumor cells or tissue to clear or eliminate the cancer or tumor expressing the one or more EBV antigens without damaging or causing illness or death in the subject administered the vaccine.

The administered vaccine can increase a cellular immune response in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase the cellular immune response in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The administered vaccine can increase interferon gamma (IFN-γ) levels in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase IFN-γ levels in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The vaccine dose can be between 1 µg to 10 mg active component/kg body weight/time and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

Other EBV-Associated Diseases or Disorders

Epstein-Barr can cause additional diseases or disorders, including, but not limited to, Guillain-Barre syndrome, meningoencephalitis, anemia, thrombotic thrombocytopenic purpura/hemolytic-uremic syndrome (TTP/HUS), disseminated intravascular coagulation (DIC), hemophagocytic lymphohistiocytosis and lymphomatoid granulomatosis. The vaccine can be used to generate or elicit an immune response in a mammal that is reactive or directed to a cell expressing a latent-stage EBV antigen in a subject. The elicited immune response can treat or prevent Guillain-Barre syndrome, meningoencephalitis, anemia, thrombotic thrombocytopenic purpura/hemolytic-uremic syndrome (TTP/HUS), disseminated intravascular coagulation (DIC), hemophagocytic lymphohistiocytosis or lymphomatoid granulomatosis disease in the subject administered the vaccine.

Combinational Therapies with Checkpoint Inhibitors

The present invention is also directed to a method of increasing an immune response in a mammal using the vaccine as described above in combination with one or more checkpoint inhibitor. In one embodiment, the vaccine as described above can comprise the EBV antigen and an antibody to a checkpoint protein. "Checkpoint inhibitor" as used herein includes inhibitors or molecules that block immune checkpoints as commonly understood in the field of cancer immunotherapy. More commonly the checkpoint inhibitors are antibodies that block the immune checkpoint proteins. Immune checkpoint proteins include, but are not limited to, PD1, PDL1, PDL2, CTLA-4, LAG3, TIM3, B7-H3, BTLA, VISTA, CD40, CEACAM1, CD80, CD86, OX40, CD27, GITR, DNAM-1, TIGIT, TMIGD2 and DC-SIGN. Some examples of known checkpoint inhibitors include, but are not limited to, ipilimumab, pembrolizumab, nivolumab, pidilizumab, avelumab and others.

The combination can be in a single formulation or can be separate and administered in sequence (either EBV antigen first and then checkpoint inhibitor, or checkpoint inhibitor first and then EBV antigen). In some embodiments, the EBV antigen can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the checkpoint inhibitor is administered to the subject. In other embodiments, the checkpoint inhibitor can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the EBV antigen is administered to the subject.

The combination of the EBV antigen and checkpoint inhibitor induces the immune system more efficiently than a vaccine comprising the EBV antigen alone. This more efficient immune response provides increased efficacy in the treatment and/or prevention of a particular cancer.

In some embodiments, the immune response can be increased by about 0.5-fold to about 15-fold, about 0.5-fold to about 10-fold, or about 0.5-fold to about 8-fold. Alternatively, the immune response in the subject administered the vaccine can be increased by at least about 0.5-fold, at least about 1.0-fold, at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, or at least about 15.0-fold.

In still other alternative embodiments, the immune response in the subject administered the vaccine can be increased about 50% to about 1500%, about 50% to about 1000%, or about 50% to about 800%. In other embodiments, the immune response in the subject administered the vaccine can be increased by at least about 50%, at least about 100%, at least about 150%, at least about 200%, at least about 250%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 950%, at least about 1000%, at least about 1050%, at least about 1100%, at least about 1150%, at least about 1200%, at least about 1250%, at least about 1300%, at least about 1350%, at least about 1450%, or at least about 1500%.

The vaccine dose can be between 1 µg to 10 mg active component/kg body weight/time, and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

Combination Treatments

The immunogenic composition may be administered in combination with other proteins and/or genes encoding CCL20, α-interferon, γ-interferon, platelet derived growth factor (PDGF), TNFα, TNIβ, GM-CSF, epidermal growth factor (EGF), cutaneous cell-attracting chemokine (CTACK), epithelial thymus-expressed chemokine (TECK), mucosae-associated epithelial chemokine (MEC), IL-12, IL-15 including IL-15 having the signal sequence deleted and optionally including the different signal peptide such as the IgE signal peptide, MHC, CD80, CD86, IL-28, IL-1, IL-2, IL-4, IL-6, IL-10, IL-18, MCP-1, MIP-1α, MIP-1β, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or combinations thereof. In some embodiments, the immunogenic composition is administered in combination with one or more of the following nucleic acid molecules and/or proteins: nucleic acid molecules selected from the group consisting of nucleic acid molecules comprising coding sequence that encode one or more of CCL20, IL-12, IL-15, IL-28, CTACK, TECK, MEC and RANTES or functional fragments thereof, and proteins selected from the group consisting of: CCL02, IL-12 protein, IL-15 protein, IL-28 protein, CTACK protein, TECK protein, MEC protein or RANTES protein or functional fragments thereof.

The immunogenic composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal, intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The immunogenic composition may be administered by traditional syringes, needleless injection devices, "microprojectile bombardment gone guns", or other physical methods such as electroporation ("EP"), "hydrodynamic method", or ultrasound.

The plasmid of the immunogenic composition may be delivered to the mammal by several well-known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The consensus antigen may be delivered via DNA injection and along with in vivo electroporation.

Electroporation

Administration of the immunogenic composition via electroporation may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, Pa.) or Elgen electroporator (Inovio Pharmaceuticals, Plymouth Meeting, Pa.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the immunogenic compositions of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the immunogenic compositions include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Aldi, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

Generation of Antigens In Vitro and Ex Vivo

In one embodiment, the optimized consensus EBV antigen is generated in vitro or ex vivo. For example, in one embodiment, a nucleic acid encoding an optimized consensus EBV antigen can be introduced and expressed in an in vitro or ex vivo cell.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

EXAMPLES

The present invention is further illustrated in the following Example. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Nucleic Acid Vaccine Targeting Epstein-Barr Virus

Figures 17A, 17B, 17C, 17D:
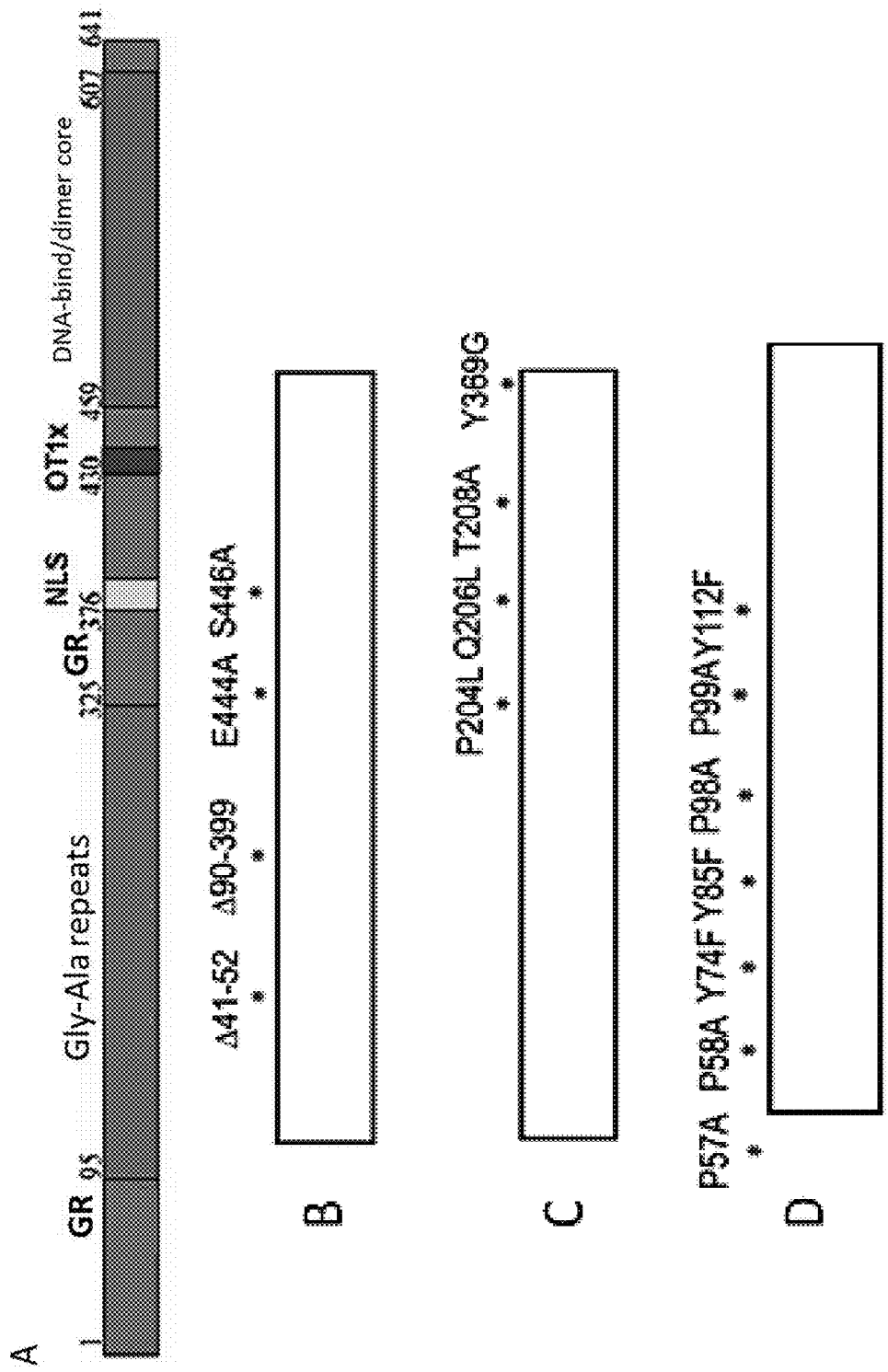
FIG. 17A through FIG. 17F, depicts diagrams of antigens for therapeutic EBV vaccines.
Figures 17E, 17F:
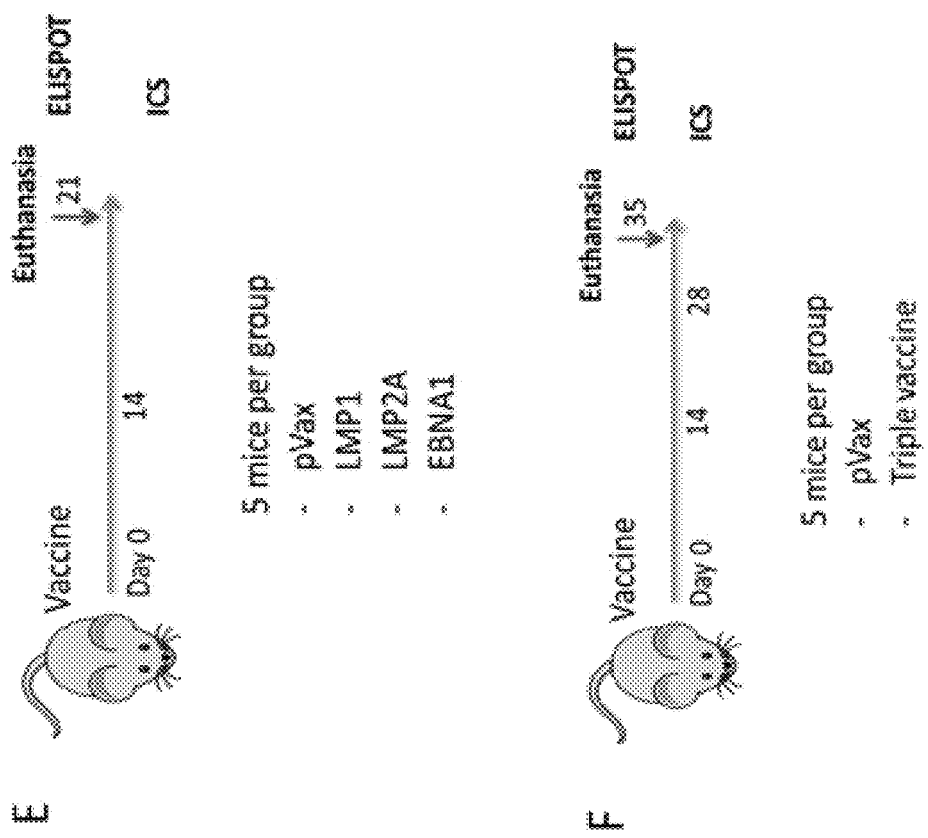
Figure 18:
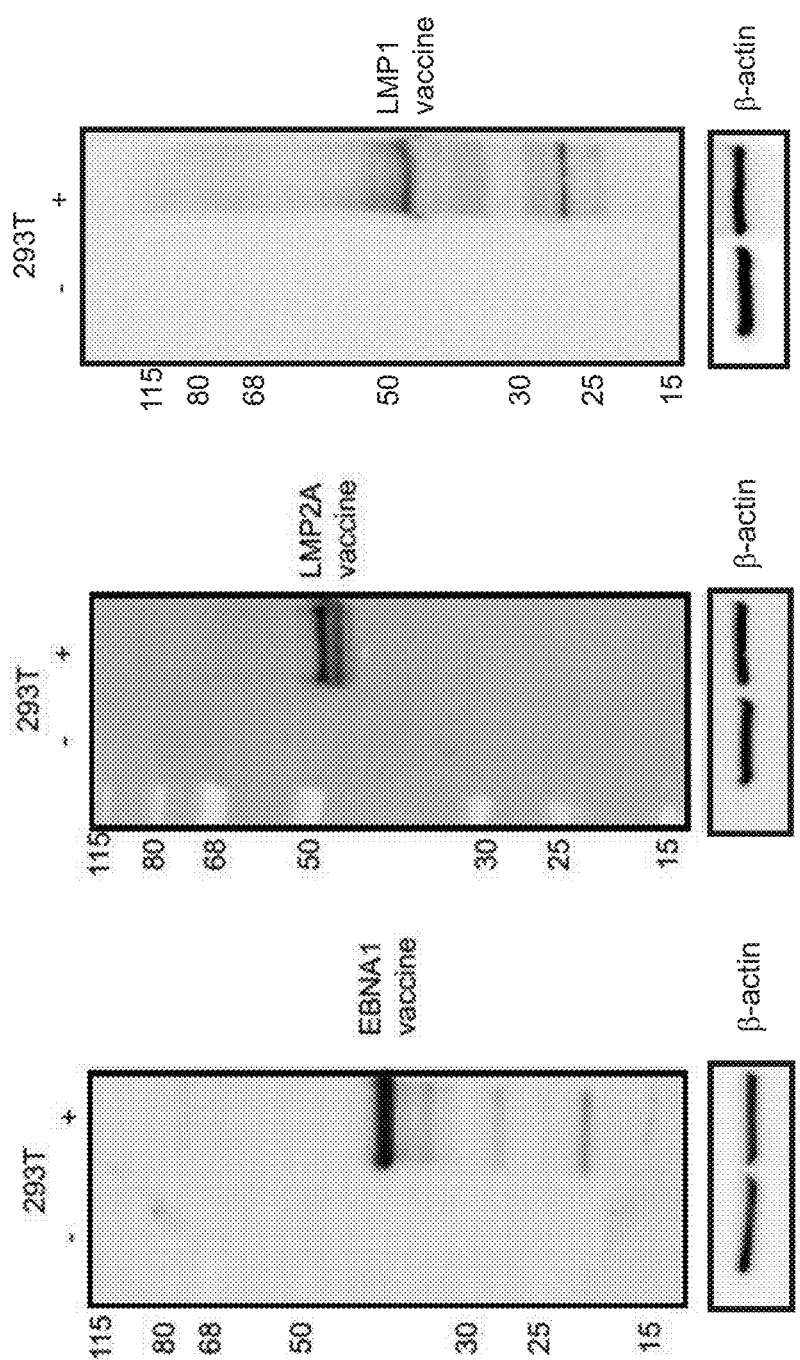
FIG. 18 depicts exemplary western blots demonstrating expression of the EBNA1. LMP2A and LMP1 vaccine constructs in 293T cells.
Figure 19:
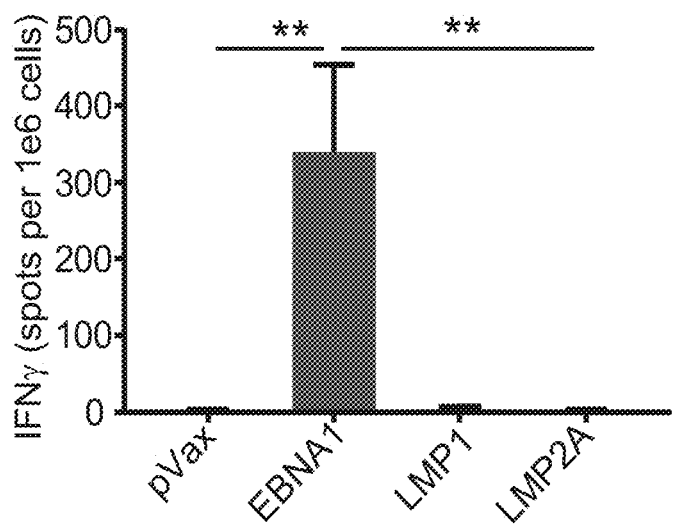
FIG. 19 depicts exemplary experimental results demonstrating that mice vaccinated with EBNA1 specifically responded to EBNA1 peptides by secreting IFNγ. Mice were vaccinated 2 times every 2 weeks with either EBNA1, LMP1, LMP2A or pVax and a week later splenocytes were collected and pulsed with EBNA1 derived peptides.
Figure 20:
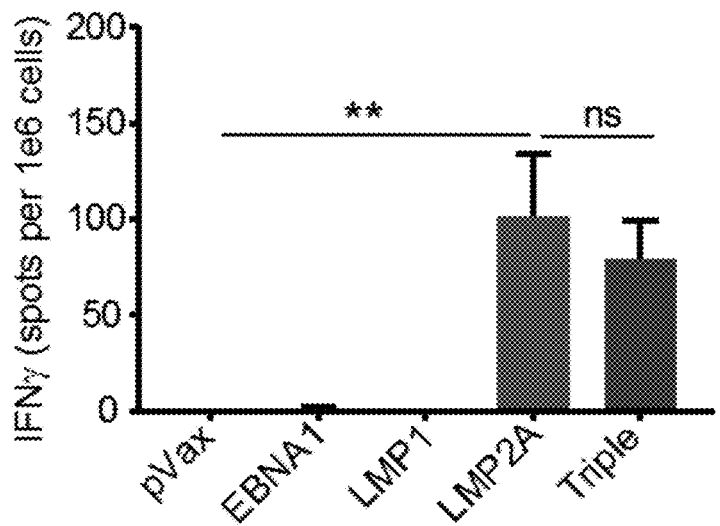
FIG. 20 depicts exemplary experimental results demonstrating that mice vaccinated with LMP2A specifically responded to LMP2A peptides by secreting IFNγ. Mice were vaccinated 2 times every 2 weeks with either EBNA1, LMP1, LMP2A, all three or pVax and a week later splenocytes were collected and pulsed with LMP2A derived peptides.
Figure 21:
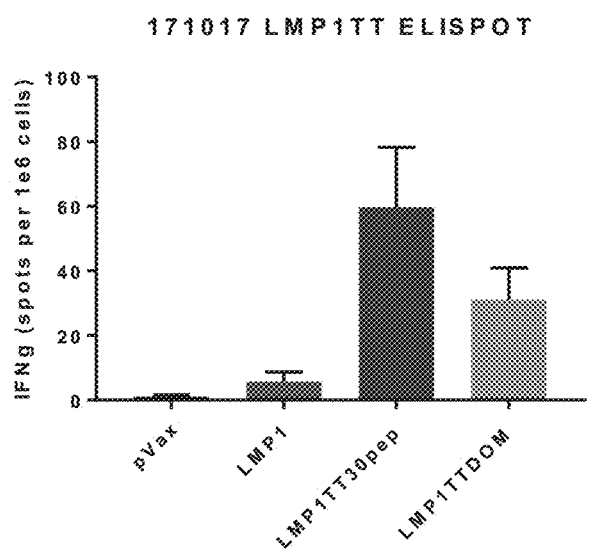
FIG. 21 depicts exemplary experimental results demonstrating that mice vaccinated with LMP1TT30 specifically responded to LMP1 peptides by secreting IFNγ with a higher strength than the other vaccines. Mice were vaccinated 3 times every 2 weeks with either LMP1, LMP1TT30 and LMPTTDOM (including modifications of the LMP1 protein that were generated to confer higher immunogenicity) or pVax and a week later splenocytes were collected and pulsed with LMP1 derived peptides.
Figure 22:
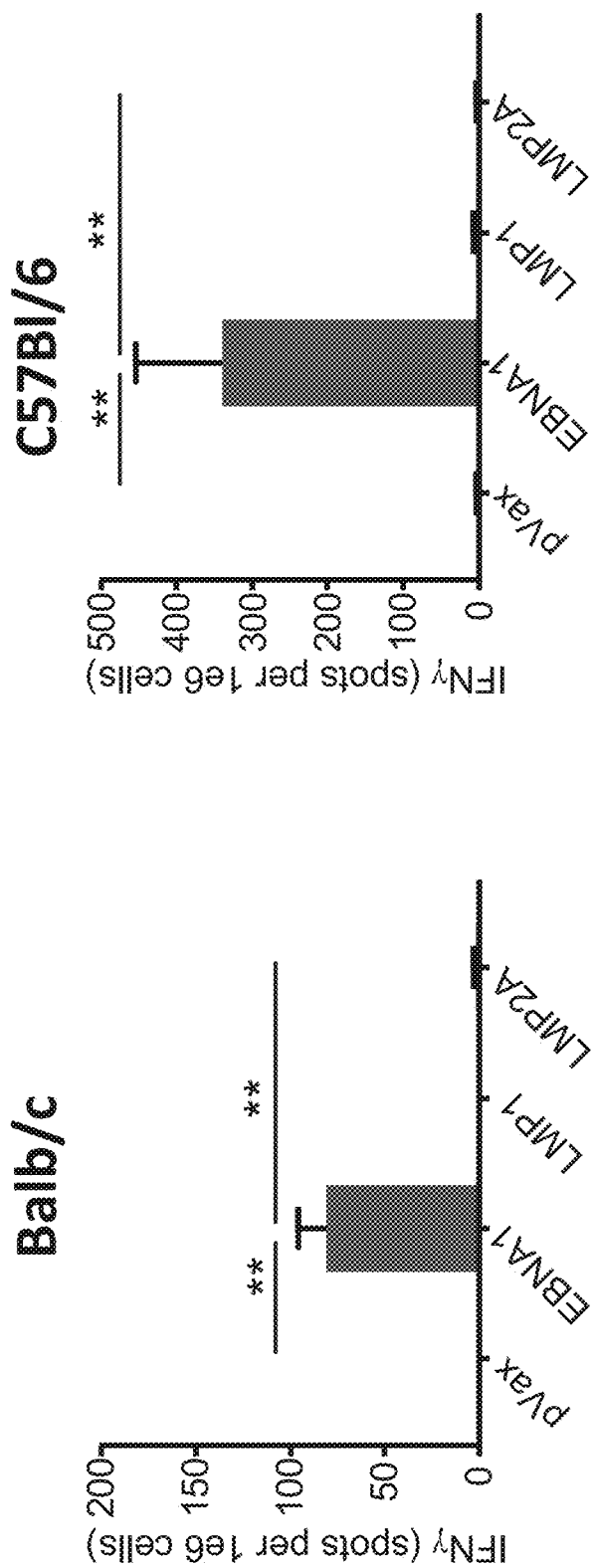
FIG. 22 depicts exemplary experimental results demonstrating that Balb/c and C57Bl/6 mice vaccinated with EBNA1 specifically responded to EBNA1 peptides by secreting IFNγ.
Figure 23:
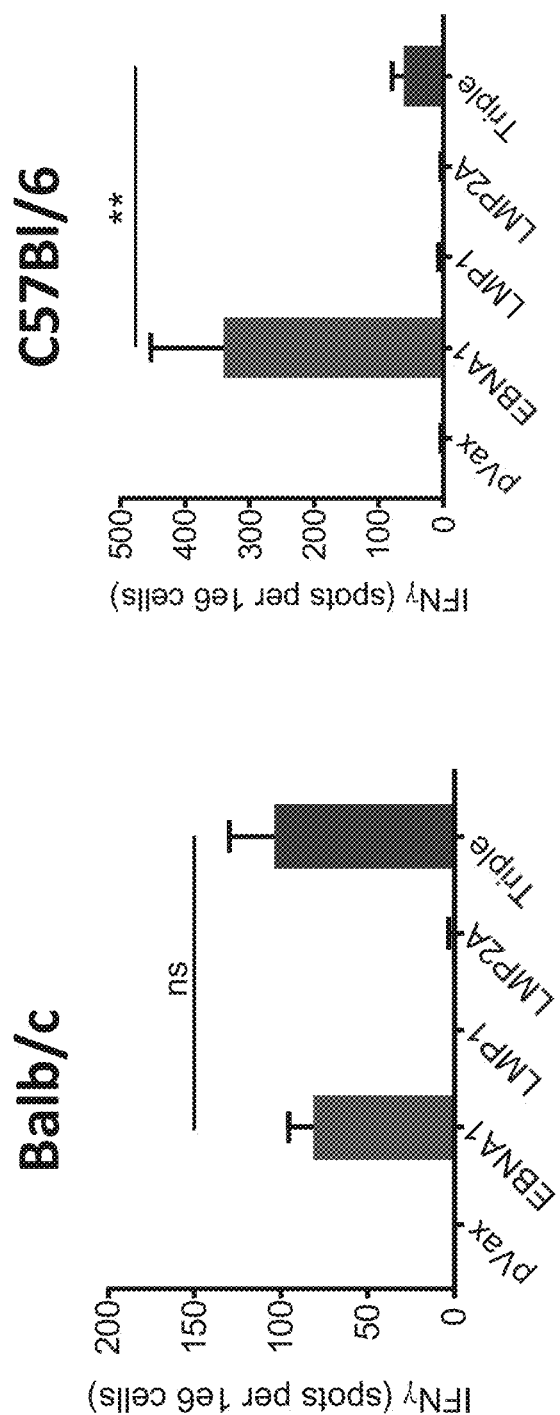
FIG. 23 depicts exemplary experimental results demonstrating that Balb/c and C57Bl/6 mice vaccinated with the triple vaccine responded to EBNA1 peptides by secreting IFNγ.
Figure 24:
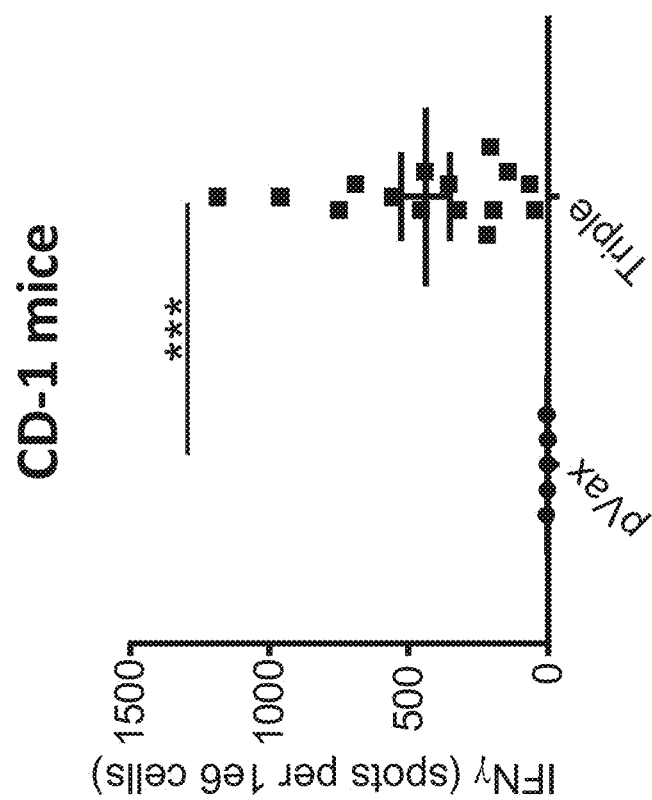
FIG. 24 depicts exemplary experimental results demonstrating that CD-1 mice vaccinated with the triple vaccine responded to EBNA1 peptides by secreting IFNγ.
Figure 25:
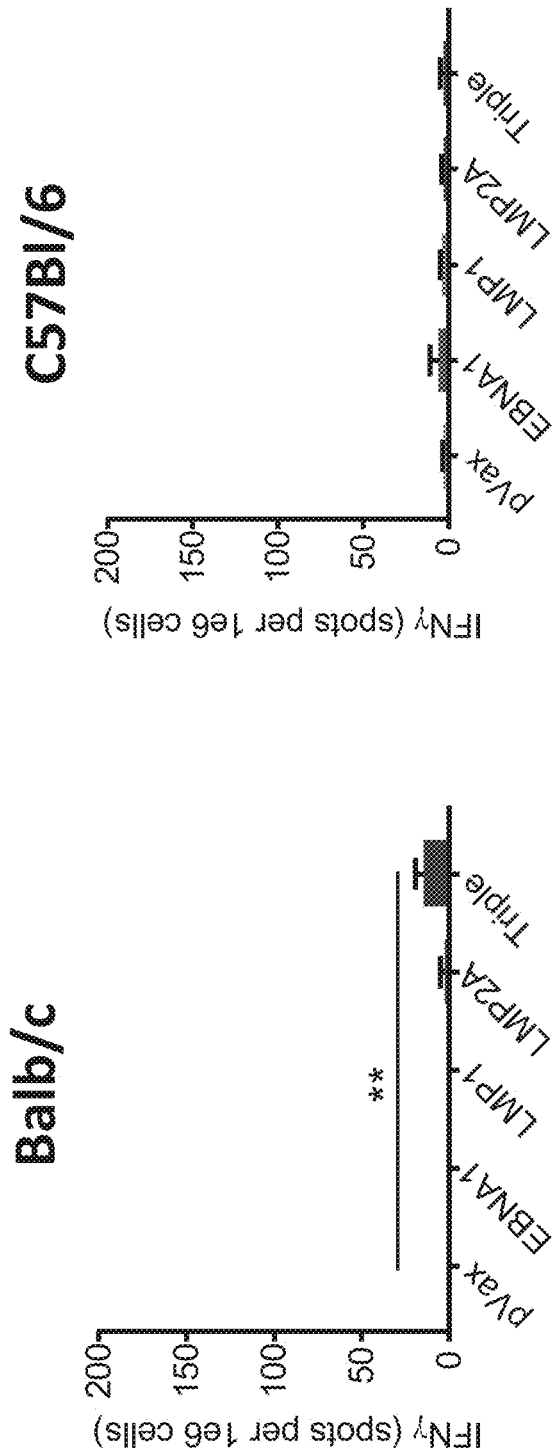
FIG. 25 depicts exemplary experimental results demonstrating the IFNγ response of vaccinated Balb/c and C57Bl/6 mice to LMP1 derived peptides.
Figure 26:
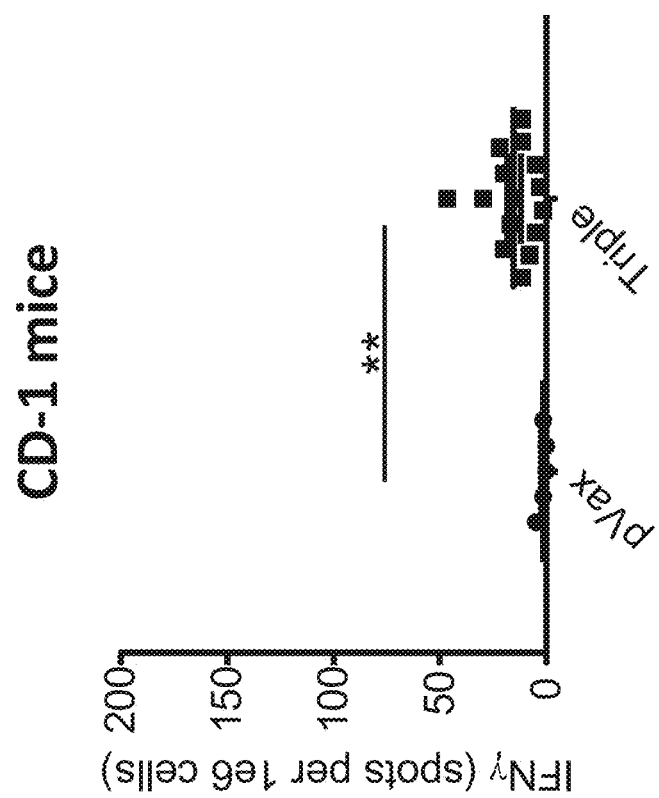
FIG. 26 depicts exemplary experimental results demonstrating the IFNγ response of CD-1 mice vaccinated with the triple vaccine to LMP1 derived peptides.
Figure 27:
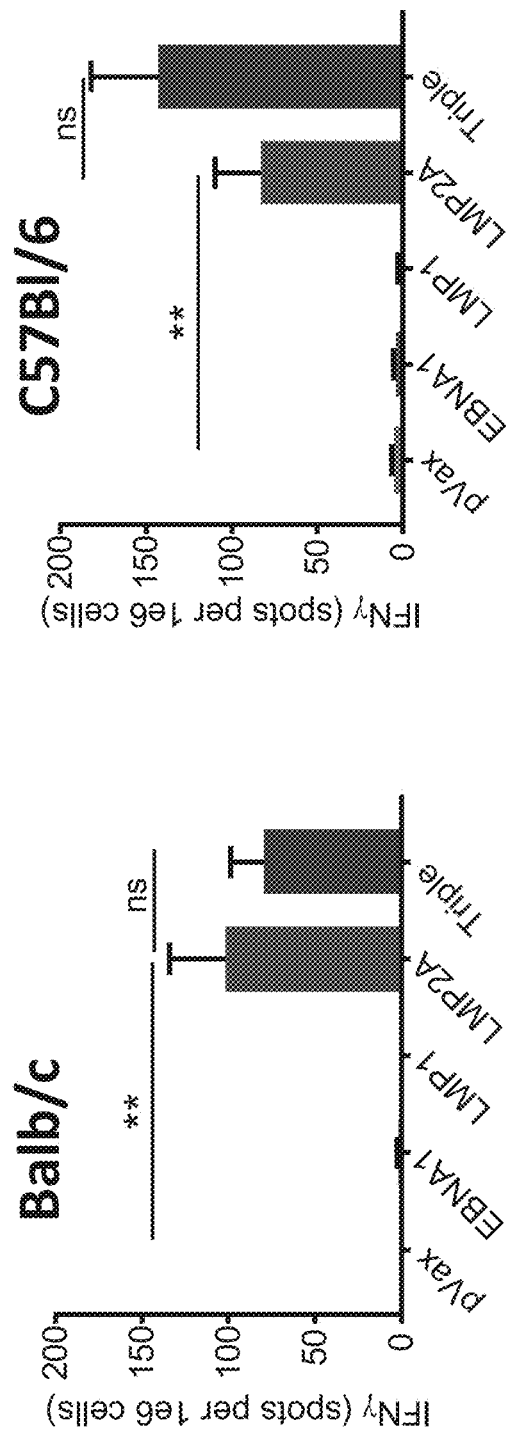
FIG. 27 depicts exemplary experimental results demonstrating that Balb/c and C57Bl/6 mice vaccinated with LMP2A or the triple vaccine responded to LMP2A peptides by secreting IFNγ.
Figure 28:
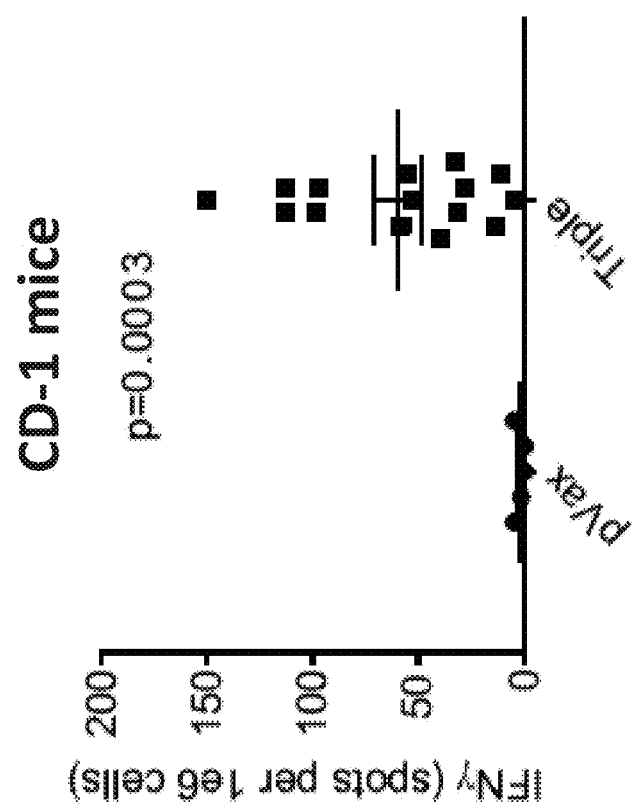
FIG. 28 depicts exemplary experimental results demonstrating that CD-1 mice vaccinated with the triple vaccine responded to LMP2A peptides by secreting IFNγ.
Figure 29:
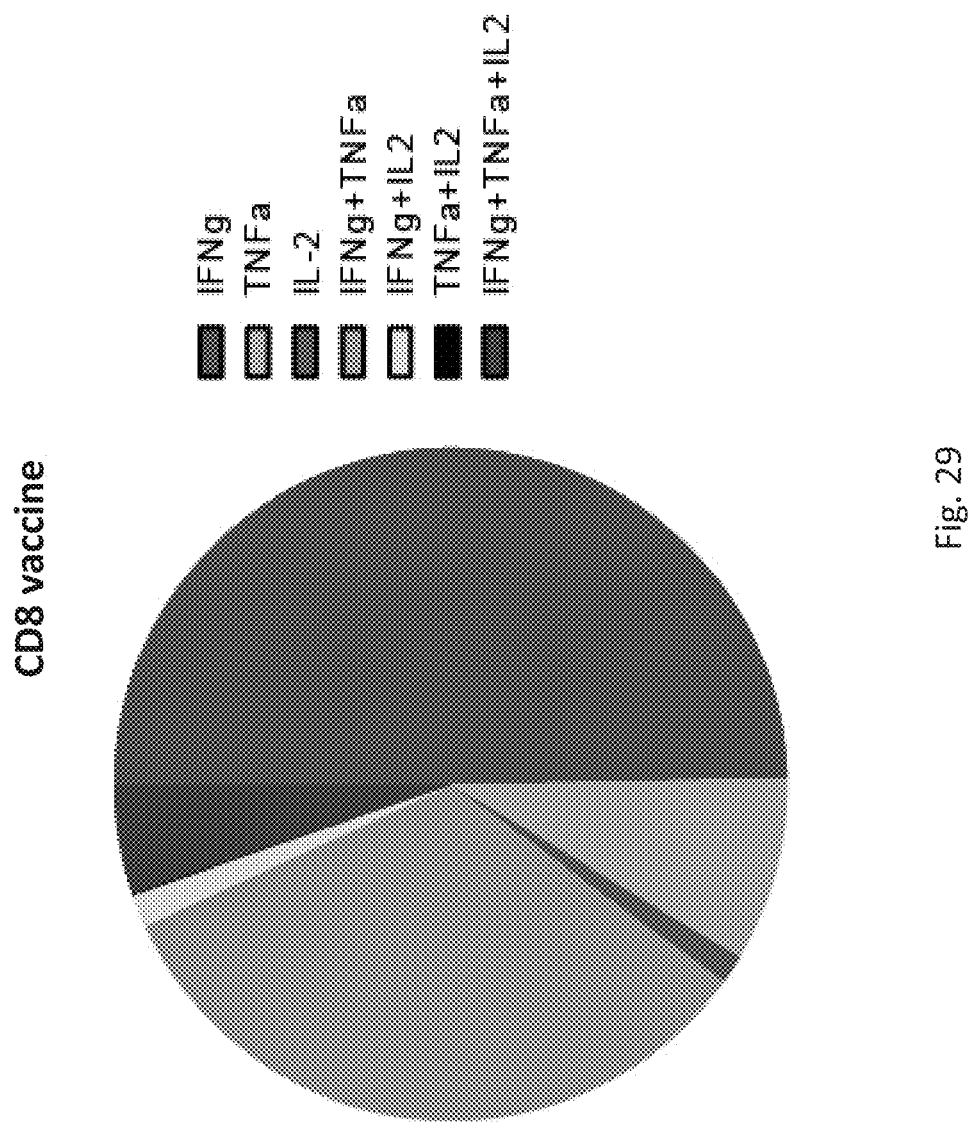
FIG. 29 depicts an exemplary comparative analysis of the CD4 and CD8 responses to vaccination.
Figure 30:
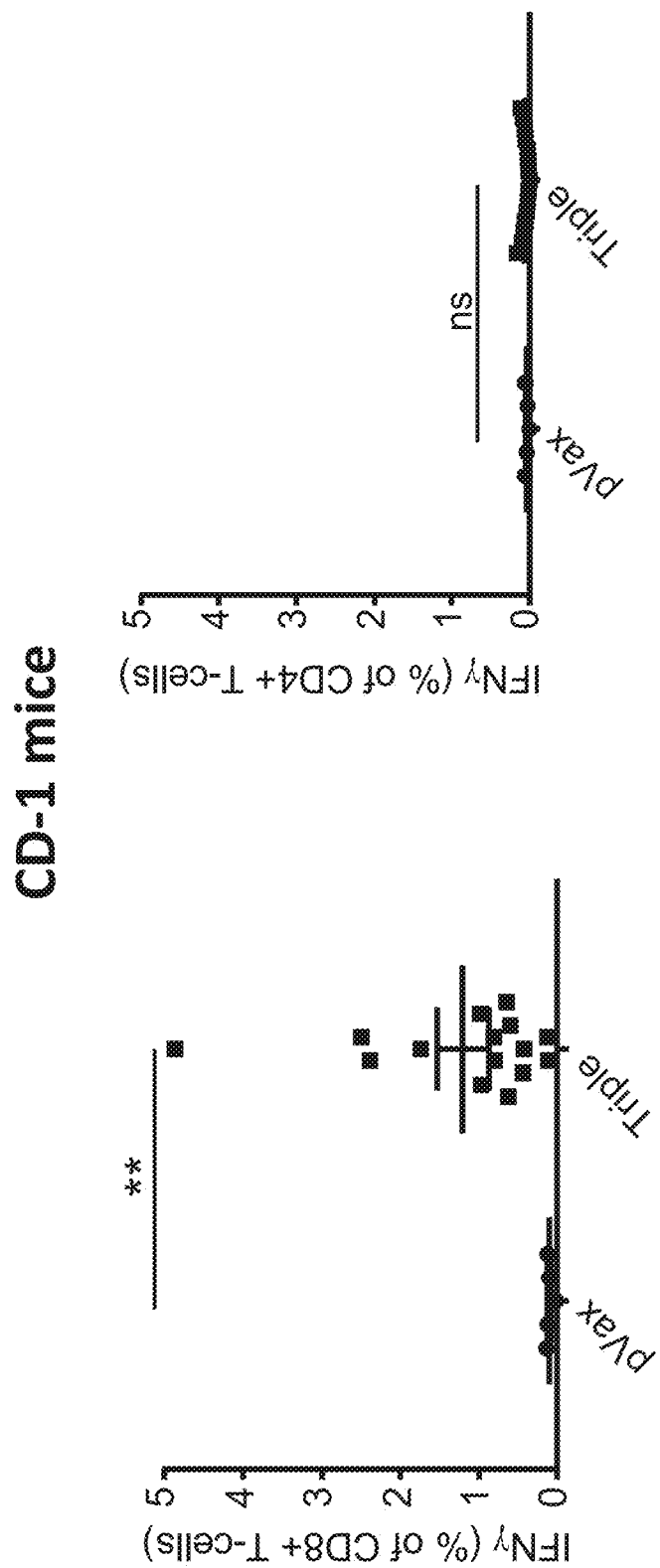
FIG. 30 depicts exemplary experimental results demonstrating that the IFNγ response is mainly CD8 driven. Mice were vaccinated with the triple vaccine and the IFNγ response was generated in response to pooled EBNA1, LMP1 and LMP2A peptides.
Figure 31:
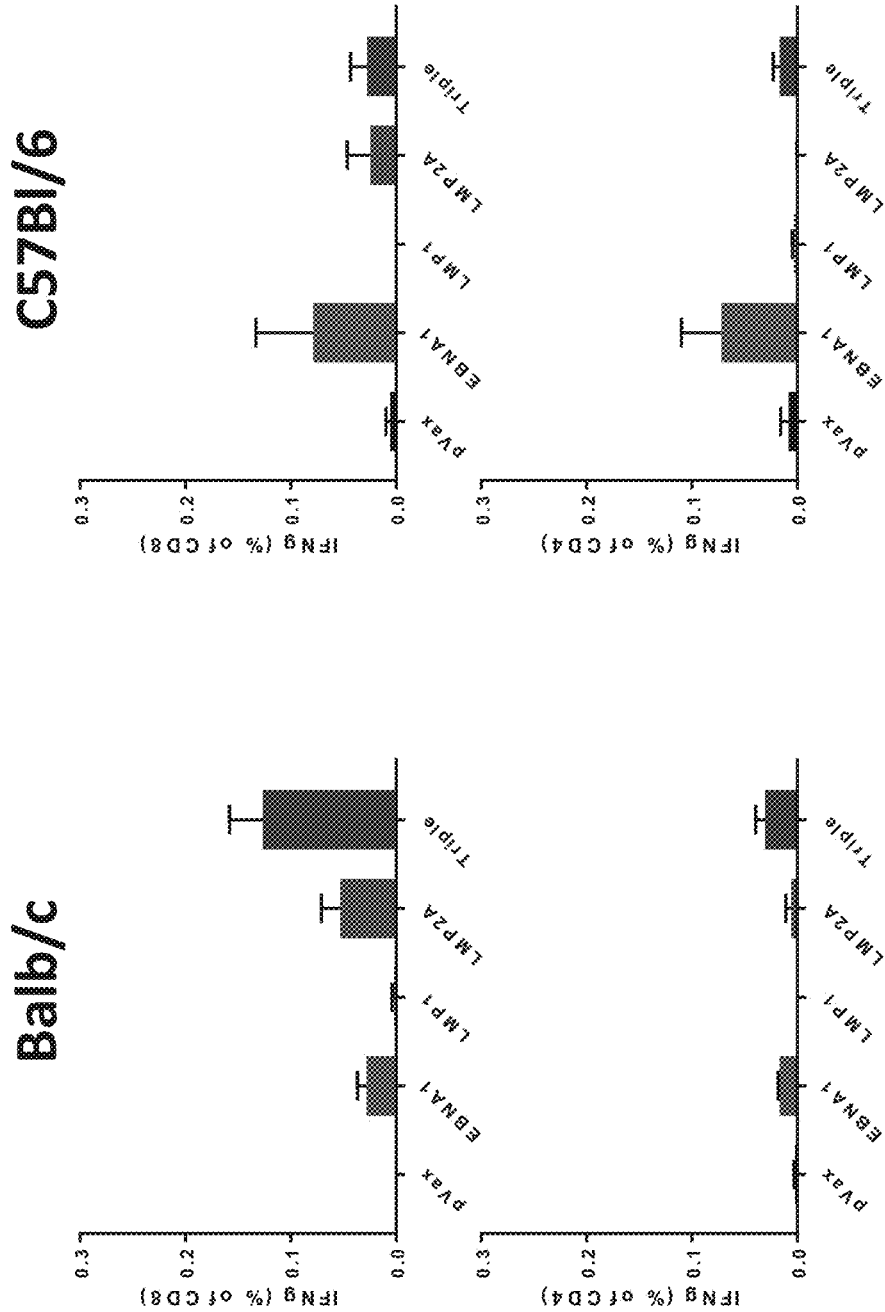
FIG. 31 depicts exemplary experimental results demonstrating the IFNγ response of vaccinated Balb/c and C57Bl/6 mice to pooled EBNA1, EMP1 and LMP2A peptides.
Figure 32:
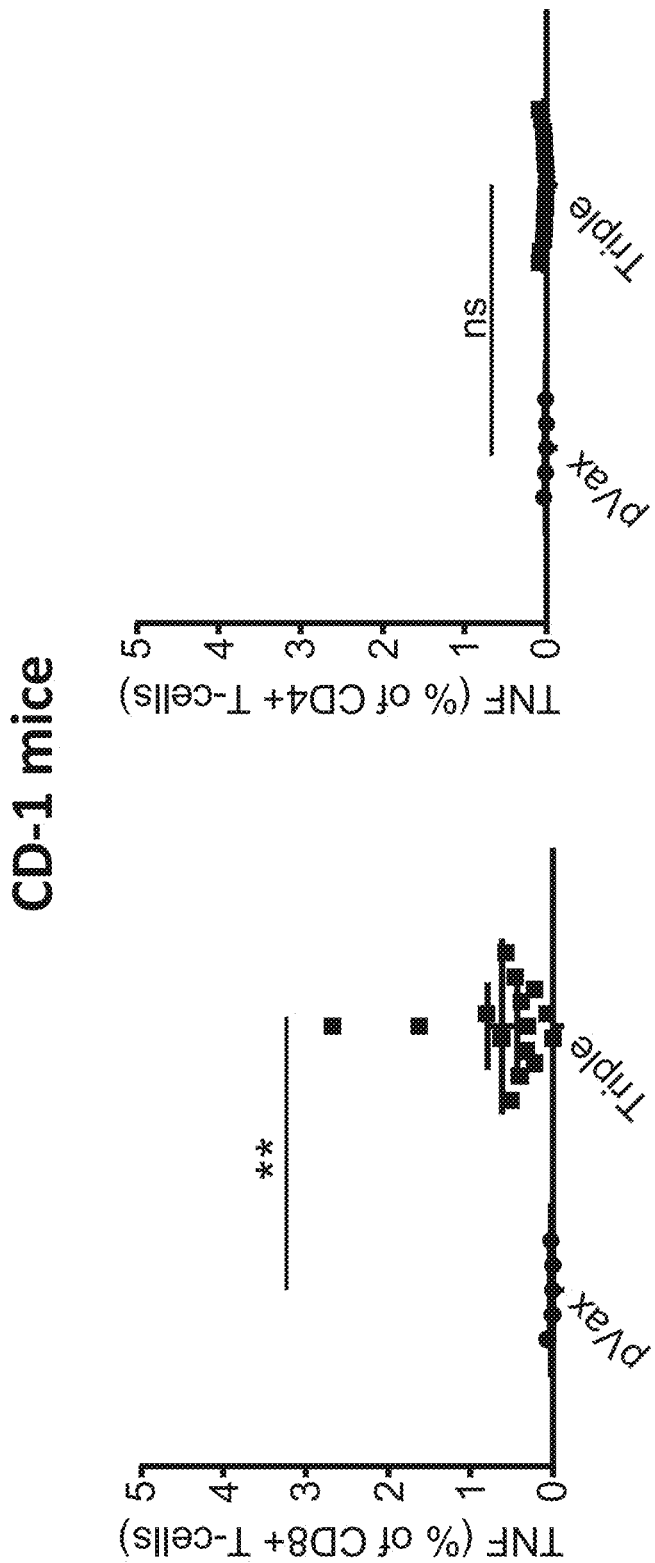
FIG. 32 depicts exemplary experimental results demonstrating the CD8 and CD4 TNF response of CD-1 mice vaccinated with the triple vaccine to pooled EBNA1, LMP1 and LMP2A peptides.
Figure 33:
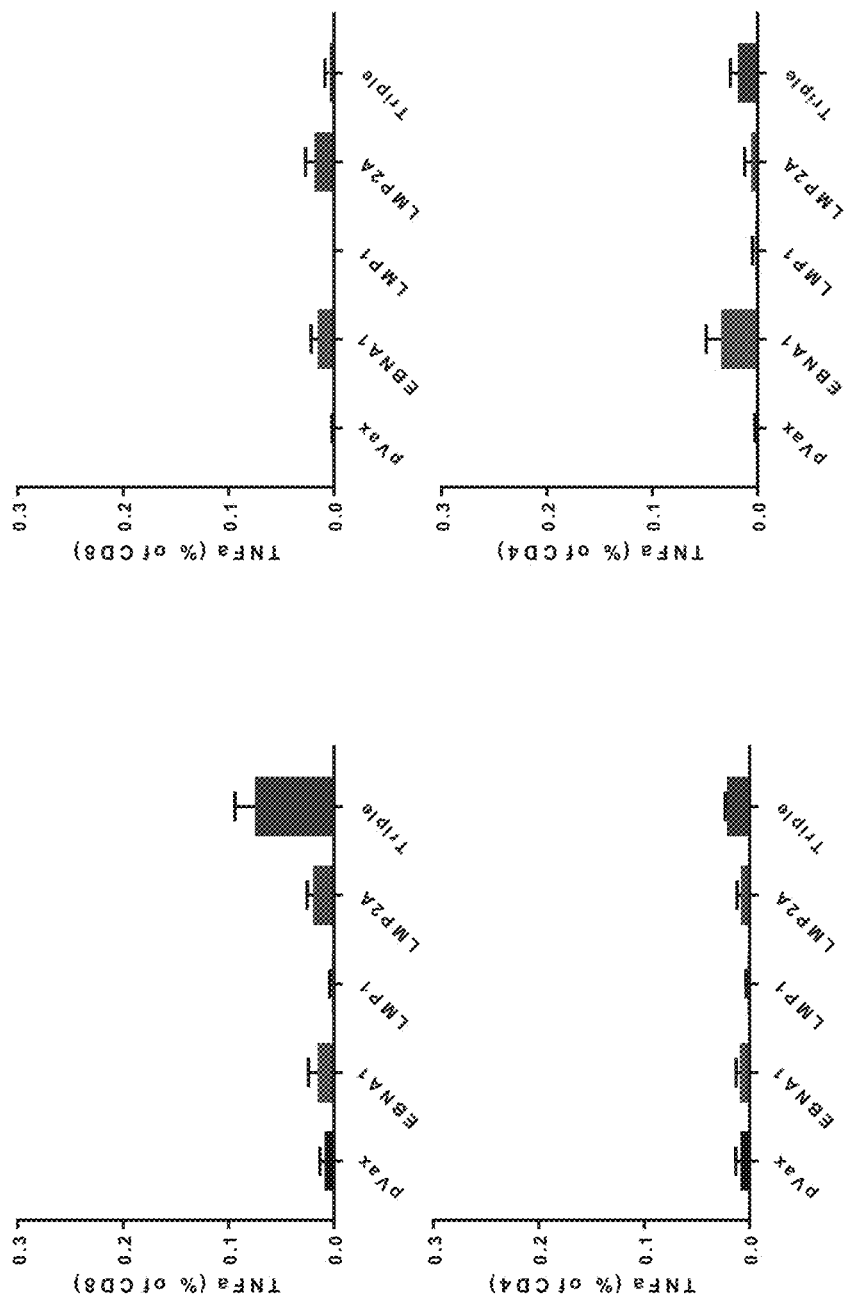
FIG. 33 depicts exemplary experimental results demonstrating that the TNF response is predominantly from CD8 T cells.
Figure 34:
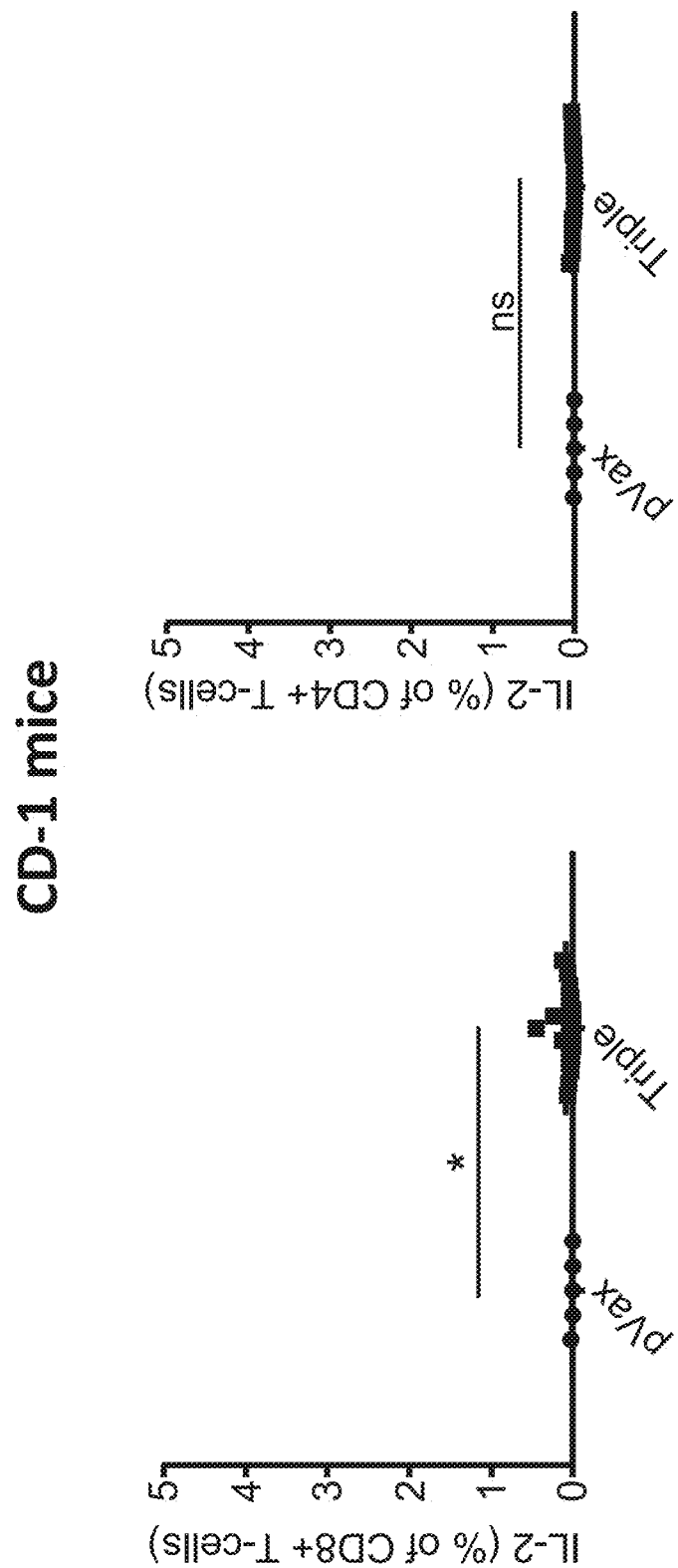
FIG. 34 depicts exemplary experimental results demonstrating the IL-2 response of CD-1 mice vaccinated with the triple vaccine to pooled EBNA1, LMP1 and LMP2A peptides.
Figure 35:
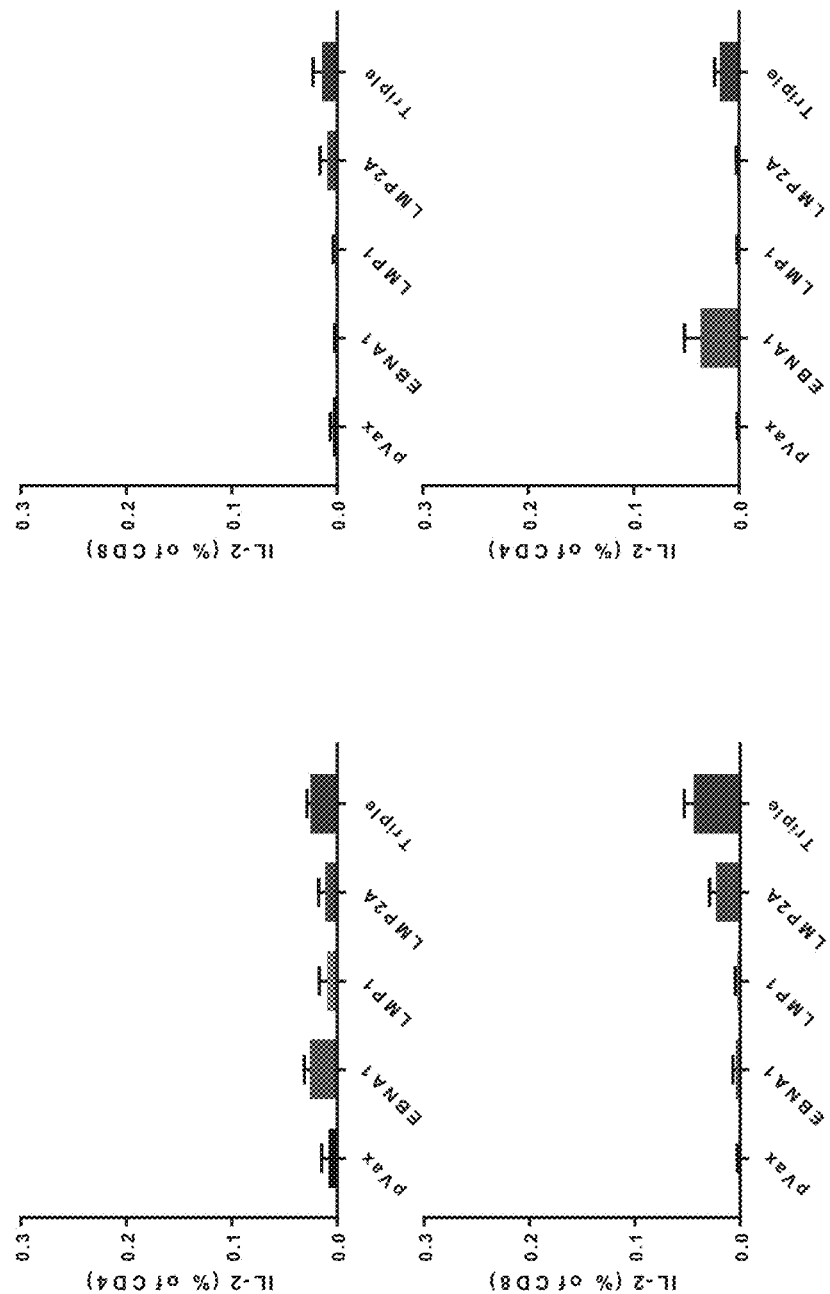
FIG. 35 depicts exemplary experimental results demonstrating that the IL-2 response is predominantly from CD4 T cells.
Figure 36:
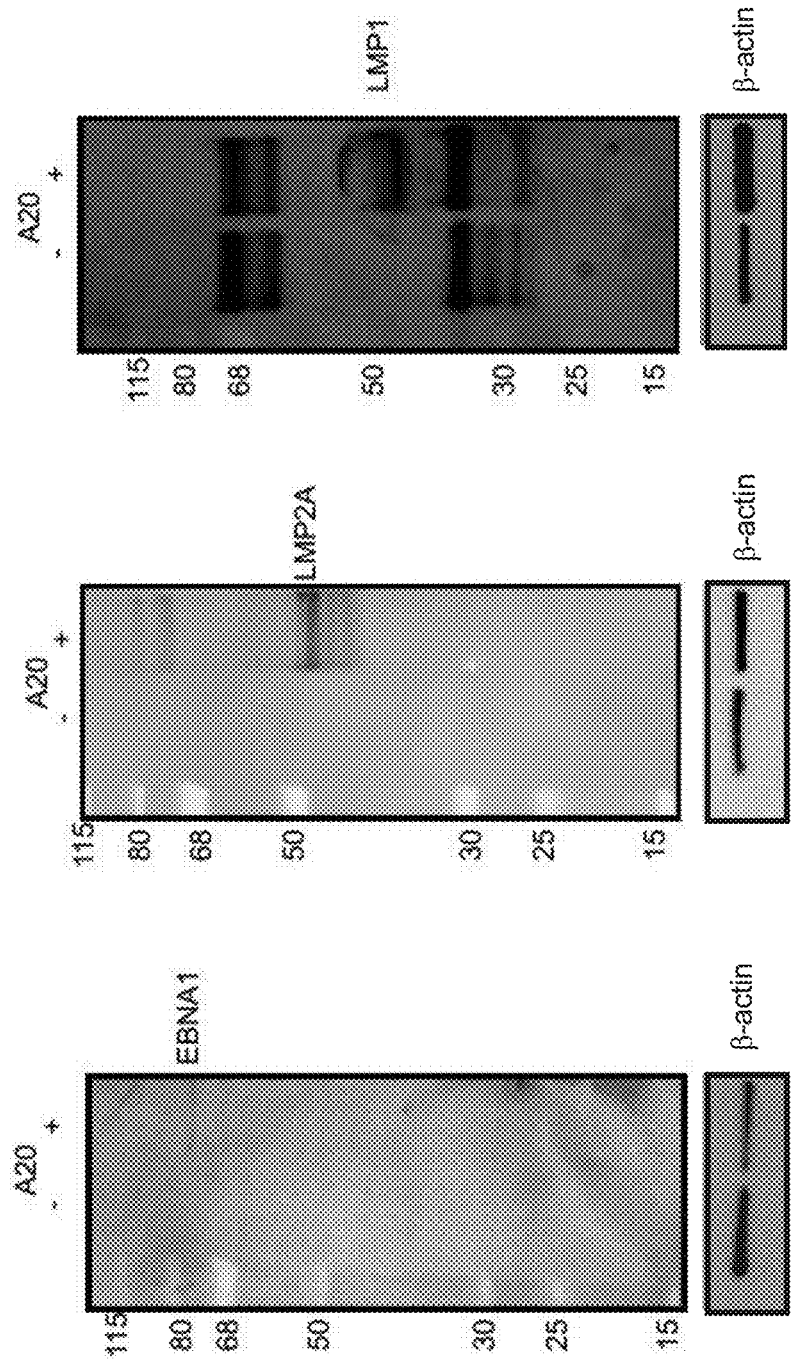
FIG. 36 depicts exemplary experimental results demonstrating the expression of EBV latent antigens in A20 cells, a lymphoma model.

Nucleic acid vaccines targeting Epstein-Barr Virus (EBV) antigens has been developed. Optimized synthetic consensus EBV antigen sequences for glycoproteins or proteins expressed during latent stage infection (FIG. 1-3) were individually cloned into mammalian expression vectors (FIG. 4) and delivered to mice via intramuscular electroporation. Mice were vaccinated 3 times every 3 weeks with the mentioned EBV vaccine or pVax and a week later splenocytes were collected and pulsed with the corresponding vaccine's protein derived peptides. FIGS. 5-16 show the immune responses elicited by the glycoprotein vaccines as measured using IFNg ELISPOT. FIG. 17B through FIG. 17D show the design of the EBV latent-stage antigen vaccine, including mutations that were introduced into the antigens to increase immunogenicity and to prevent adverse effects on the cells that receive the vaccines, more specifically development of cancer due to the presence of those proteins. The vaccination schedules used for latent-stage EBV vaccination are shown in FIG. 17E and FIG. 17F. FIGS. 18-36 show that the EBV latent protein vaccines against EBNA1, LMP1 and LMP2A were able to induce immune responses in mice when administered individually or as a triple vaccine.

Example 2

BARF1 Vaccine

The experiments described in this example demonstrate the therapeutic and prophylactic use of the BARF1 vaccine to reduce tumor growth, delay tumor progression and increase survival of BARF1 expressing tumors.

Figure 37:
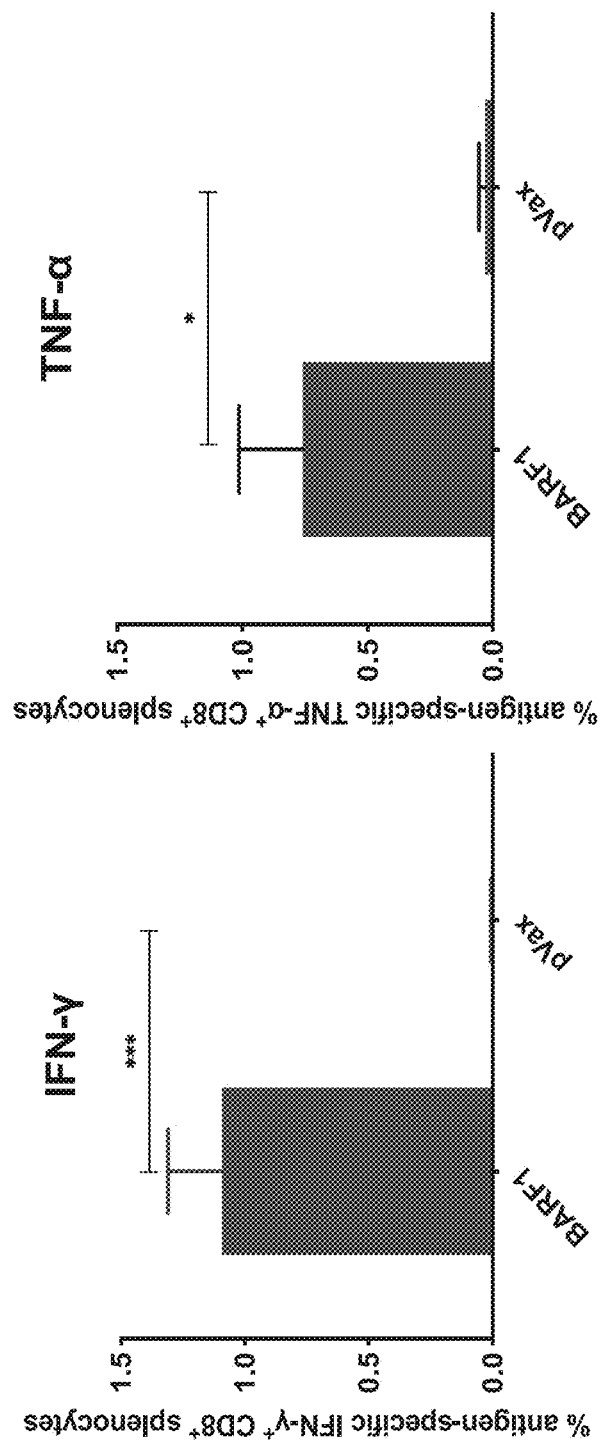
FIG. 37 depicts exemplary experimental results demonstrating that the BARF1 vaccine generates polyfunctional CD8 T cells.

FIG. 37 provides data demonstrating that the BARF1 vaccine generates polyfunctional CD8 T cells. Mice were vaccinated with BARF1 or pVax empty vector every 2 weeks for 3 times and a week later euthanized. Spleens were collected and 2 million spleens were plated with 5 peptides predicted to be immunogenic (through MHCI binding)

derived from BARF1 for 5 hours. Splenocytes were then stained for IFNγ and TNFα. CD8 T cells BARF1 vaccinated mice elicited significantly higher IFNγ and TNFα than the pVax vaccinated mice.

Figure 38:
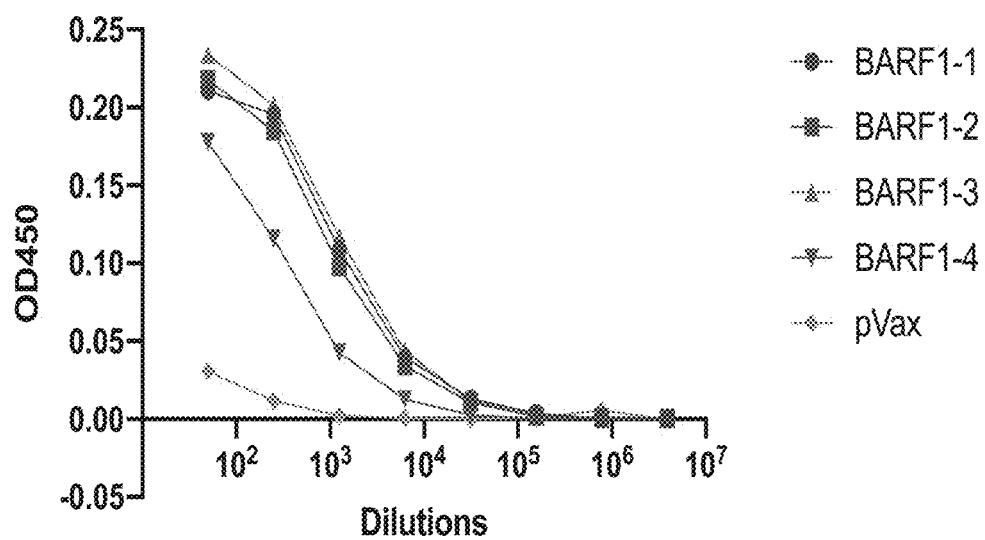
FIG. 38 depicts exemplary experimental results demonstrating that the BARF1 vaccine generates specific antibodies.

FIG. 38 provides data demonstrating that the BARF1 vaccine generates specific antibodies. Mice were vaccinated with BARF1 or pVax empty vector every 2 weeks for 3 times and a week later euthanized. Sera were collected after euthanasia for testing for anti-BARF1 antibodies. A 96 well plate was coated with recombinant BARF1 overnight and sera from the different mice were tested for binding. Sera from BARF1 vaccinated mice showed BARF1 specific antibody binding, unlike pVax immunized mice.

Figure 39:
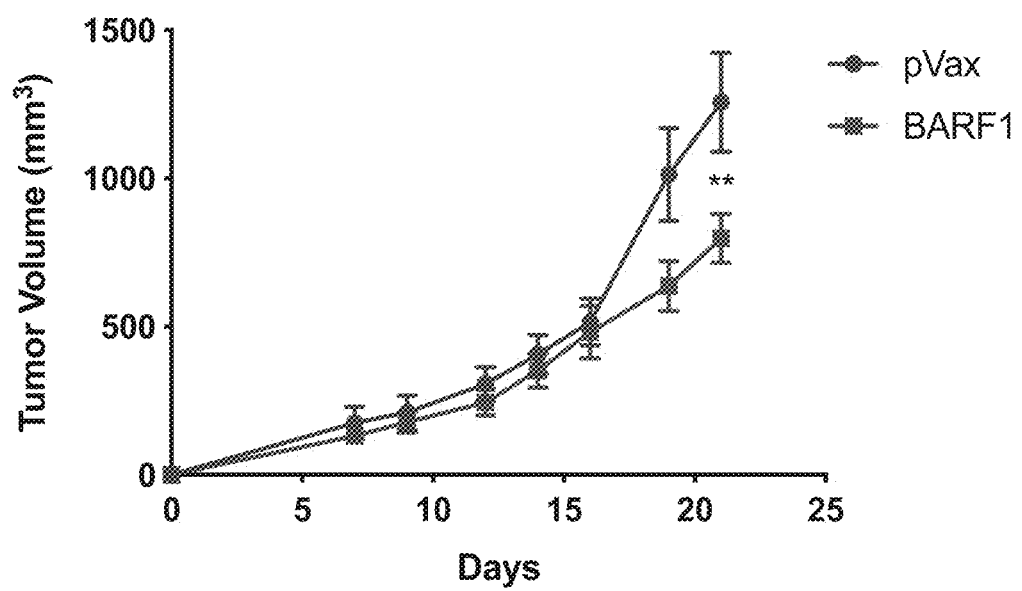
FIG. 39 depicts exemplary experimental results demonstrating the therapeutic use of BARF1 vaccine delays tumor progression of MC38-BARF1 tumors.

FIG. 39 provides data demonstrating the therapeutic use of BARF1 vaccine delays tumor progression of MC38-BARF1 tumors. 2 groups of 5 mice each were implanted with 500,000 MC38-BARF1 cells subcutaneously. A day later they received therapeutic vaccination with BARF1 or pVax empty vector (20 µg DNA in 30 µl H2O) followed by adaptive electroporation with CELLECTRA 3P device, Mice were vaccinated weekly for 4 doses and tumor growth measured with calipers. FIG. 39 shows a significant delay in tumor growth in the mice vaccinated with BARF1 vaccine.

Figure 40:
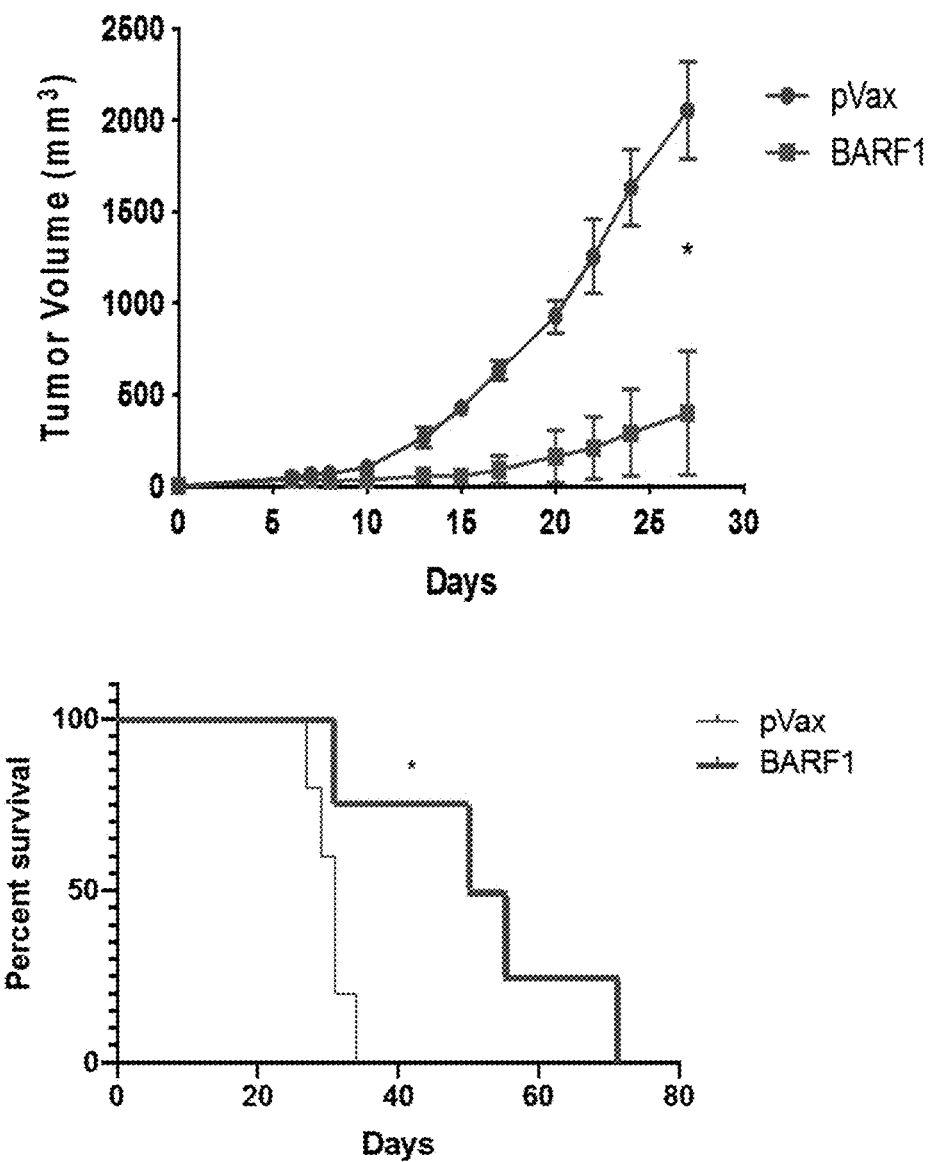
FIG. 40 depicts exemplary experimental results demonstrating the prophylactic use of BARF1 vaccine delays tumor progression of MC38-BARF1 tumors.

FIG. 40 provides data demonstrating the prophylactic use of BARF1 vaccine delays tumor progression of MC38-BARF1 tumors. 2 groups of 5 mice each were vaccinated every 2 weeks for 3 doses (20 µg BARF1 or pVax in 30 µl H₂O followed by adaptive electroporation with CELLECTRA 3P device) and implanted with 500,000 MC38-BARF1 cells subcutaneously a week after the final immunization. Tumor growth was measured with calipers. FIG. 40 shows a significant delay in tumor growth and increase in survival in the mice vaccinated with BARF1 vaccine.

Example 3

EBV Glycoprotein Vaccines Generate Antibodies Against EBV

Figure 41:
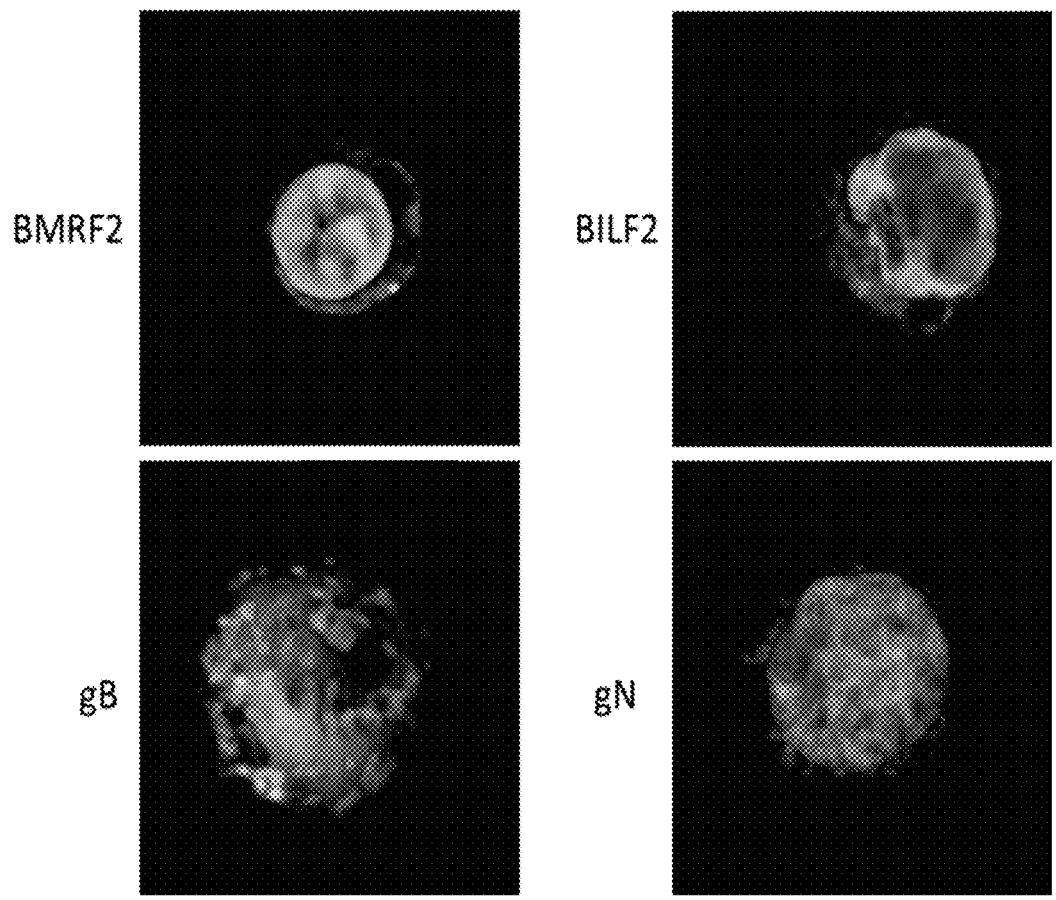
FIG. 41 depicts exemplary experimental results demonstrating that the EBV glycoprotein vaccines generate antibodies against EBV.

This example provides data demonstrating that mice immunized with consensus EBV glycoprotein vaccines generate antibodies against EBV B95.8 (ebv infected B cells) were stained with sera from mice immunized with different EBV vaccines (BMRF2, BILF2, gB, gN, gHgL, and combination of gp350-gp42-gHgLgB) followed by a secondary anti-mouse antibody, were able to bind to the viral particles in the B cells (FIG. 41).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. An immunogenic composition comprising a nucleic acid molecule encoding at least one Epstein-Barr virus (EBV) antigen, wherein the nucleic acid molecule comprises a nucleotide sequence selected from the group consisting of:
   a) a nucleotide sequence having at least about 90% identity over an entire length of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31,
   b) an immunogenic fragment of a nucleotide sequence having at least about 90% identity over at least 60% of the nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31,
   c) a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, and
   d) an immunogenic fragment of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31.

2. The immunogenic composition of claim 1, comprising a nucleic acid molecule encoding at least two EBV antigens selected from the group consisting of an EBV glycoprotein antigen, and a latent-stage EBV antigen.

3. The immunogenic composition of claim 1, wherein the immunogenic composition comprises
   a) at least one nucleotide sequence encoding at least one EBV glycoprotein antigen;
   b) at least one nucleotide sequence encoding at least one latent-stage EBV antigen;
   or a combination thereof.

4. The immunogenic composition of claim 3, wherein
   a) at least one EBV glycoprotein antigen is selected from the group consisting of gp350, gp42, gL, gH, gB, gM, gN, BDLF2, BDLF3, BILF1, BILF2, and BARF1;
   b) at least one latent-stage EBV antigen is selected from the group consisting of EBNA1, LMP1, LMP2A and a combination thereof;
   or any combination thereof.

5. The immunogenic composition of claim 1, wherein the antigen comprises at least one mutation that disrupts at least one function of a native EBV antigen selected from the group consisting of DNA replication, mitotic segregation, transcriptional activation, autoregulation, and suppression of the lytic cycle, wherein the antigen is selected from the group consisting of:
   a) an EBNA1 antigen comprising at least one imitation selected from the group consisting of Δ41-52, Δ90-309, mutation of amino acid E444, and mutation of amino acid S446 relative to the native antigen sequence;
   b) an LMP1 antigen comprising at least one mutation at an amino acid residue selected from the group consisting of P204, Q206, T208 and Y369 relative to the native antigen sequence; and
   c) an LMP2A antigen comprising at least one mutation at an amino acid residue selected from the group consisting of P57, P58, Y74, Y85, P98, P99 and Y112 relative to the native antigen sequence.

6. The immunogenic composition of claim 1, wherein the nucleic acid molecule encodes a peptide comprising an amino acid sequence selected from the group consisting of
   a) an amino acid sequence having at least about 99% identity over an entire length of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32,
   b) an immunogenic fragment comprising at least about 99% identity over at least 60% of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32,
c) an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, and
d) an immunogenic fragment comprising at least 60% of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32;
or any combination thereof.

7. The immunogenic composition of claim 1, wherein
a) the nucleic acid molecule is selected from the group consisting of a DNA molecule and an RNA molecule encoded by said DNA molecule;
b) the nucleic acid molecule comprises a nucleotide sequence encoding a peptide that is operably linked to at least one regulatory sequence selected from the group consisting of a start codon, a leader sequence, an IgE leader sequence, and at least one stop codon;
c) the nucleic acid molecule comprises an expression vector;
d) the nucleic acid molecule is incorporated into a viral particle;
or any combination thereof.

8. The immunogenic composition of claim 1, further comprising a pharmaceutically acceptable excipient, an adjuvant, or a combination thereof.

9. A nucleic acid molecule encoding a peptide comprising an amino acid sequence selected from the group consisting of
a) an amino acid sequence having at least about 99% identity over an entire length of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32,
b) an immunogenic fragment comprising at least about 99% identity over at least 60% of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32,
c) an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, and
d) an immunogenic fragment comprising at least 60% of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32.

10. The nucleic acid molecule of claim 9, wherein
a) the nucleic acid molecule is selected from the group consisting of a DNA molecule and an RNA molecule;
b) the nucleic acid molecule encodes a peptide that is operably linked to at least one regulatory sequence selected from the group consisting of a start codon, a leader sequence, an IgE leader sequence and a stop codon;
c) the nucleic acid molecule comprises an expression vector;
d) the nucleic acid molecule comprises a viral particle;
or any combination thereof.

11. The nucleic acid molecule of claim 9, wherein the nucleic acid molecule comprises a nucleotide sequence selected from the group consisting of
a) a nucleotide sequence having at least about 90% identity over an entire length of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31,
b) an immunogenic fragment of a nucleotide sequence having at least about 90% identity over at least 60% of the nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31,
c) a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, and
d) an immunogenic fragment of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31.

12. The nucleic acid molecule of claim 10, wherein the nucleic acid molecule encodes a peptide comprising an amino acid sequence selected from the group consisting of
a) an amino acid sequence having at least about 99% identity over an entire length of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32,
b) an immunogenic fragment comprising at least about 99% identity over at least 60% of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, c) an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, and d) an immunogenic fragment comprising at least 60% of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, operably linked to an amino acid sequence as set forth in SEQ ID NO:33.

13. The nucleic acid molecule of claim 12, wherein the nucleic acid molecule comprises a nucleotide sequence selected from the group consisting of a) a nucleotide sequence having at least about 90% identity over an entire length of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, b) an immunogenic fragment of a nucleotide sequence having at least about 90% identity over at least 60% of the nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21 SEQ ID NO:23, SEQ ID NO:25, SEQ ID NO:27, SEQ ID NO:29, and SEQ ID NO:31, c) a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, and d) an immunogenic fragment of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, operably linked to an nucleotide sequence encoding SEQ ID NO:33.

14. A peptide comprising an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, b) an immunogenic fragment comprising at least about 99% identity over at least 60% of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, c) an amino acid sequence having at least about 99% identity over an entire length of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, and d) an immunogenic fragment comprising at least 60% of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32.

15. A method of inducing an immune response against an EBV antigen or preventing EBV infection or treating or preventing a disease or disorder associated with EBV latency in a subject in need thereof, the method comprising administering an immunogenic composition of claim 1 to the subject.

16. The method of claim 15, wherein the immunogenic composition comprises a) at least one nucleotide sequence encoding at least one EBV glycoprotein antigen;

b) at least one nucleotide sequence encoding at least one latent-stage EBV antigen;

or any combination thereof.

17. The method of claim 16, wherein a) at least one EBV glycoprotein antigen is selected from the group consisting of gp350, gp42, gL, gH, gB, gM, gN, BDLF2, BDLF3, BILF1, BILF2, and BARF1;

b) at least one latent-stage EBV antigen is selected from the group consisting of EBNA1, LMP1, LMP2A and a combination thereof;

or any combination thereof.

18. The method of claim 15, wherein the disease or disorder associated with EBV latency is at least one of Burkitt's lymphoma, Hodgkin lymphoma, Post-transplant lymphoma, T-cell lymphoma, AIDS-associated B-cell lymphoma, gastric carcinoma, nasopharyngeal carcinoma, infectious mononucleosis, and an autoimmune disease or disorder.

* * * * *